(12) United States Patent
Sun et al.

(10) Patent No.: US 12,336,855 B2
(45) Date of Patent: Jun. 24, 2025

(54) IMAGING SYSTEMS AND METHODS

(71) Applicant: SHANGHAI UNITED IMAGING HEALTHCARE CO., LTD., Shanghai (CN)

(72) Inventors: Biao Sun, Shanghai (CN); Junchao Sun, Shanghai (CN); Xunsan Tao, Shanghai (CN); Weiran Zhuang, Shanghai (CN); Qianqian Yu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 126 days.

(21) Appl. No.: 18/167,817

(22) Filed: Feb. 10, 2023

(65) Prior Publication Data
US 2023/0181144 A1    Jun. 15, 2023

Related U.S. Application Data

(63) Continuation of application No. PCT/CN2020/108275, filed on Aug. 10, 2020.

(51) Int. Cl.
*A61B 6/00* (2024.01)
(52) U.S. Cl.
CPC .................. *A61B 6/547* (2013.01)
(58) Field of Classification Search
CPC ......... A61B 6/102; A61B 6/12; A61B 6/4417; A61B 6/4441; A61B 6/487; A61B 6/5264; A61B 6/545; A61B 6/547
See application file for complete search history.

(56) References Cited

U.S. PATENT DOCUMENTS

| 6,175,614 B1 | 1/2001 | Jensen et al. |
| 6,272,368 B1 | 8/2001 | Alexandrescu |

(Continued)

FOREIGN PATENT DOCUMENTS

| CN | 101308102 A | 11/2008 |
| CN | 103315739 A | 9/2013 |

(Continued)

OTHER PUBLICATIONS

Cao, Guogang et al., Medical Image Registration Based on Differential Evolution, Journal of Applied Sciences, 26 (3): 274-280, 2008.

(Continued)

*Primary Examiner* — Dani Fox
(74) *Attorney, Agent, or Firm* — METIS IP LLC

(57) ABSTRACT

The present disclosure provides systems and methods for automated scan preparation and real-time monitoring/adjustment in medical imaging. The automated scan preparation may include positioning a target subject to be scanned by a medical imaging device, determining a rotation scheme of the medical imaging device, targeting a scan region of the target subject with an imaging isocenter of the medical imaging device, determining target position(s) of component(s) of the medical imaging device, performing a virtual scan, generating a reference subject model representing an internal structure of the target subject, or the like. The real-time monitoring/adjustment operations may include achieving automatic brightness stabilization, monitoring a posture of the target subject, adjusting the position of component(s) of the medical imaging device, estimating a dose distribution, monitoring a treatment of the target subject, performing a motion correction, or the like.

20 Claims, 29 Drawing Sheets

(56) References Cited

U.S. PATENT DOCUMENTS

| | | |
|---|---|---|
| 9,892,233 B2 | 2/2018 | Zeilinger |
| 2001/0025142 A1 | 9/2001 | Wessels et al. |
| 2002/0065461 A1 | 5/2002 | Cosman |
| 2004/0167395 A1 | 8/2004 | Behrenbruch et al. |
| 2005/0053267 A1 | 3/2005 | Mostafavi |
| 2005/0201516 A1 | 9/2005 | Ruchala et al. |
| 2005/0218341 A1 | 10/2005 | Saracen et al. |
| 2005/0281374 A1 | 12/2005 | Cheng et al. |
| 2006/0078195 A1 | 4/2006 | Vaillant et al. |
| 2007/0140427 A1 | 6/2007 | Jensen et al. |
| 2007/0238952 A1 | 10/2007 | Boese et al. |
| 2008/0279333 A1 | 11/2008 | Sattler et al. |
| 2009/0037130 A1 | 2/2009 | Feiweier et al. |
| 2009/0161818 A1 | 6/2009 | Sakurai et al. |
| 2009/0285357 A1 | 11/2009 | Khamene |
| 2010/0027742 A1 | 2/2010 | Movassaghi et al. |
| 2010/0046815 A1 | 2/2010 | Von Berg et al. |
| 2010/0061607 A1 | 3/2010 | Sgouros et al. |
| 2011/0002444 A1 | 1/2011 | Schmitt et al. |
| 2011/0026666 A1 | 2/2011 | Nijhof et al. |
| 2011/0082361 A1 | 4/2011 | Jattke et al. |
| 2011/0092793 A1 | 4/2011 | Thomson et al. |
| 2011/0135053 A1 | 6/2011 | Noordhoek et al. |
| 2011/0135177 A1 | 6/2011 | Ohishi |
| 2011/0224904 A1 | 9/2011 | Feiten et al. |
| 2012/0099778 A1 | 4/2012 | Helm et al. |
| 2012/0121062 A1 | 5/2012 | Sowards-Emmerd et al. |
| 2013/0225958 A1 | 8/2013 | Ichihara et al. |
| 2013/0237811 A1 | 9/2013 | Mihailescu et al. |
| 2013/0267830 A1 | 10/2013 | Ojha et al. |
| 2014/0086390 A1 | 3/2014 | Nakatsugawa et al. |
| 2014/0098934 A1 | 4/2014 | Kondo |
| 2014/0119625 A1 | 5/2014 | Oh et al. |
| 2014/0185780 A1 | 7/2014 | Zhao et al. |
| 2014/0210470 A1 | 7/2014 | Xu |
| 2014/0228678 A1 | 8/2014 | Meyer et al. |
| 2014/0235923 A1 | 8/2014 | Mcnutt et al. |
| 2014/0254900 A1 | 9/2014 | Sturm |
| 2014/0314205 A1 | 10/2014 | Carelsen et al. |
| 2015/0139515 A1 | 5/2015 | Smith et al. |
| 2015/0145987 A1 | 5/2015 | Sugano |
| 2015/0228071 A1 | 8/2015 | Jockel et al. |
| 2015/0302604 A1 | 10/2015 | Lee et al. |
| 2016/0089094 A1 | 3/2016 | Kawamura et al. |
| 2016/0225170 A1 | 8/2016 | Rifu et al. |
| 2016/0331463 A1 | 11/2016 | Nötzli et al. |
| 2017/0000447 A1 | 1/2017 | Profio et al. |
| 2017/0035374 A1 | 2/2017 | Fer et al. |
| 2017/0086758 A1 | 3/2017 | Mc Carthy et al. |
| 2017/0202633 A1 | 7/2017 | Liu |
| 2017/0209220 A1 | 7/2017 | Krugman et al. |
| 2017/0216624 A1 | 8/2017 | Kondziolka et al. |
| 2017/0220709 A1 | 8/2017 | Wan et al. |
| 2017/0311921 A1 | 11/2017 | Feuerlein et al. |
| 2017/0316562 A1 | 11/2017 | Haberland et al. |
| 2017/0360514 A1 | 12/2017 | Eichler et al. |
| 2018/0103930 A1 | 4/2018 | Choi et al. |
| 2018/0193667 A1 | 7/2018 | Kaiser et al. |
| 2018/0225863 A1 | 8/2018 | Grady et al. |
| 2018/0263706 A1 | 9/2018 | Averbuch |
| 2018/0325489 A1 | 11/2018 | De Beni et al. |
| 2018/0350081 A1 | 12/2018 | Hsieh |
| 2018/0353151 A1 | 12/2018 | Tang |
| 2018/0360408 A1 | 12/2018 | Quan |
| 2018/0368785 A1 | 12/2018 | Wiegert et al. |
| 2018/0368791 A1* | 12/2018 | König ................. A61B 6/4085 |
| 2018/0369611 A1 | 12/2018 | Owens et al. |
| 2019/0054315 A1 | 2/2019 | Isola et al. |
| 2019/0059829 A1 | 2/2019 | Han |
| 2019/0066260 A1 | 2/2019 | Suehling et al. |
| 2019/0076102 A1 | 3/2019 | Mistretta et al. |
| 2019/0076103 A1 | 3/2019 | Mistretta et al. |
| 2019/0105010 A1 | 4/2019 | Oishi et al. |
| 2019/0143145 A1 | 5/2019 | Laurence, Jr. et al. |
| 2019/0147648 A1 | 5/2019 | Wolff |
| 2019/0183439 A1 | 6/2019 | Joerger et al. |
| 2019/0206051 A1 | 7/2019 | Cao et al. |
| 2019/0311490 A1 | 10/2019 | Crawford et al. |
| 2019/0328265 A1 | 10/2019 | Zho et al. |
| 2019/0329073 A1 | 10/2019 | Meltsner |
| 2020/0020101 A1 | 1/2020 | Mewes et al. |
| 2020/0090371 A1 | 3/2020 | Hu |
| 2020/0187887 A1 | 6/2020 | Alon Cohen et al. |
| 2020/0203002 A1 | 6/2020 | Amthor et al. |
| 2020/0206536 A1 | 7/2020 | Wang et al. |
| 2020/0218922 A1 | 7/2020 | Chen et al. |
| 2020/0226746 A1 | 7/2020 | Schwartzbard et al. |
| 2020/0234449 A1 | 7/2020 | Regensburger et al. |
| 2020/0245894 A1 | 8/2020 | Shi et al. |
| 2020/0323498 A1 | 10/2020 | Tong et al. |
| 2020/0352524 A1 | 11/2020 | Hu et al. |
| 2021/0093221 A1 | 4/2021 | Harder |
| 2021/0125331 A1 | 4/2021 | Sun et al. |

FOREIGN PATENT DOCUMENTS

| | | |
|---|---|---|
| CN | 104840211 A | 8/2015 |
| CN | 106413236 A | 2/2017 |
| CN | 107292815 A | 10/2017 |
| CN | 107647878 A | 2/2018 |
| CN | 107789001 A | 3/2018 |
| CN | 107811646 A | 3/2018 |
| CN | 108095745 A | 6/2018 |
| CN | 109009202 A | 12/2018 |
| CN | 109758170 A | 5/2019 |
| CN | 110099502 A | 8/2019 |
| CN | 110298794 A | 10/2019 |
| CN | 110575193 A | 12/2019 |
| CN | 110916700 A | 3/2020 |
| CN | 110960241 A | 4/2020 |
| CN | 111134698 A | 5/2020 |
| CN | 111214764 A | 6/2020 |
| CN | 111374690 A | 7/2020 |
| CN | 111493909 A | 8/2020 |
| DE | 102008046348 A1 | 3/2010 |
| DE | 102014219666 A1 | 3/2016 |
| DE | 102018209691 A1 | 12/2019 |
| EP | 2948056 B1 | 5/2020 |
| EP | 2967480 B1 | 4/2022 |
| JP | H11206757 A | 8/1999 |
| JP | 2004275745 A | 10/2004 |
| JP | 2009153579 A | 7/2009 |
| JP | 2015213536 A | 12/2015 |
| JP | 2016154577 A | 9/2016 |
| JP | 2017077457 A | 4/2017 |
| KR | 20170009685 A | 1/2017 |
| KR | 101898575 B1 | 9/2018 |
| WO | 2009052497 A2 | 4/2009 |
| WO | 2015136392 A1 | 9/2015 |
| WO | 2017030276 A1 | 2/2017 |
| WO | 2018224039 A1 | 12/2018 |
| WO | 2019110135 A1 | 6/2019 |
| WO | 2020042943 A1 | 3/2020 |
| WO | 2020044345 A1 | 3/2020 |

OTHER PUBLICATIONS

Xiong, Xin, Face Recognition Technology and Application, Yellow River Water Conservancy Press, 2018, 16 pages.

International Search Report in PCT/CN2020/108275 mailed on May 13, 2021, 6 pages.

Written Opinion in PCT/CN2020/108275 mailed on May 13, 2021, 4 pages.

He, Li et al., Standardized Management and Operation of Medical Equipment in Operating Room, People's Military Medical Press, 2014, 12 pages.

Cao, Huizhi et al., A Medical Segmentation Algorithm Based on Registration and ASM, Chinese Journal of Medical Imaging Technology, 22(7): 1108-1111, 2006.

The Extended European Search Report in European Application No. 20948954.1 mailed on May 8, 2023, 8 pages.

(56) References Cited

OTHER PUBLICATIONS

Ye, Chengwei et al., Clinical Applicability of Optical Surface Imaging System in Thorax Tumor Radiation Therapy, Biomedical Engineering and Clinical Medicine, 22(3): 281-285, 2018.
Booij Ronald et al., "Accuracy of automated patient positioning in CT using a 3D camera for body contour detection", European Radiology, 29(4): 2079-2088, 2018.
The Extended European Search Report in European Application No. 24213805.5 mailed on Feb. 27, 2025, 7 pages.

* cited by examiner

700

```
┌─────────────────────────────────────────────────────┐
│ Obtaining image data indicative of a position of a  │  710
│ target subject relative to one or more components   │
│ of the medical imaging device, the image data being │
│ captured by an image capturing device               │
└─────────────────────────────────────────────────────┘
                          ↓
┌─────────────────────────────────────────────────────┐
│ Obtaining position information relating to the one  │  720
│ or more components of the medical imaging device    │
└─────────────────────────────────────────────────────┘
                          ↓
┌─────────────────────────────────────────────────────┐
│ Determining a plurality of regions of the target    │  730
│ subject based on the image data and the position    │
│ information, different regions of the plurality of  │
│ regions corresponding to different positioning      │
│ procedures of the target subject                    │
└─────────────────────────────────────────────────────┘
                          ↓
┌─────────────────────────────────────────────────────┐
│ Causing a terminal device to display a target image │  740
│ of the target subject with a plurality of           │
│ annotations of the plurality of regions             │
└─────────────────────────────────────────────────────┘
```

FIG. 7

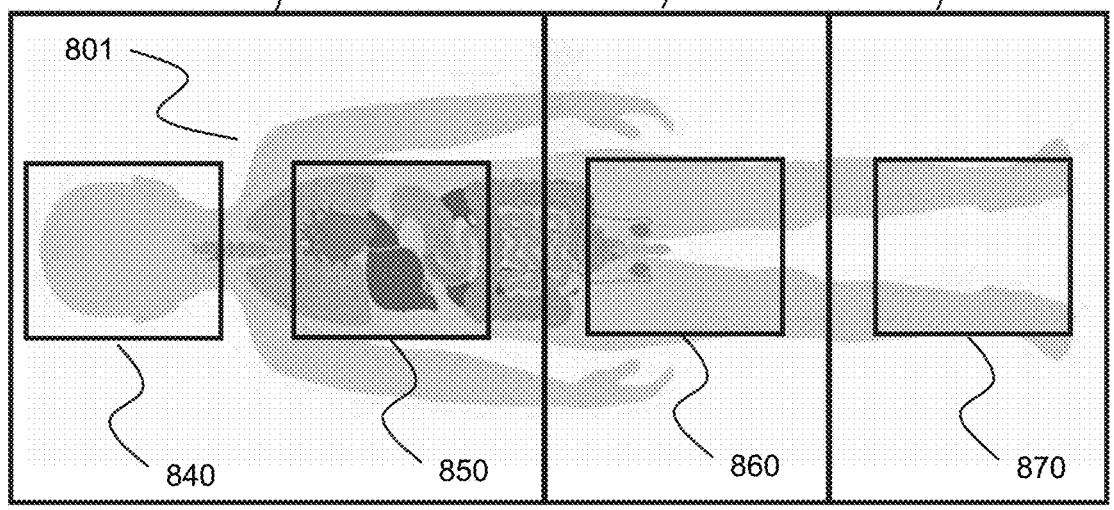

FIG. 8

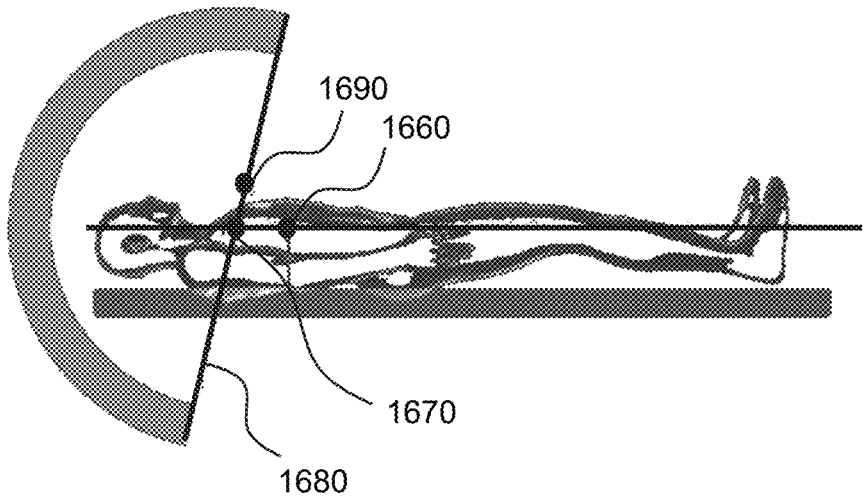

| Obtaining image data of a target subject to be scanned by a medical imaging device, wherein the image data is acquired by at least one image capturing device, and the medical imaging device has an imaging isocenter | 1710 |

| Determining, based on the image data, a scan region of the target subject | 1720 |

| Adjusting one or more components of the medical imaging device such that the scan region is targeted by the imaging isocenter of the medical imaging device | 1730 |

IMAGING SYSTEMS AND METHODS

CROSS-REFERENCE TO RELATED APPLICATIONS

This application is a Continuation of International Application No. PCT/CN2020/108275 filed on Aug. 10, 2020, the contents of which are hereby incorporated by reference.

TECHNICAL FIELD

The present disclosure generally relates to medical imaging, and more particularly, relates to systems and methods for automated scan preparation and real-time monitoring in medical imaging.

BACKGROUND

Medical imaging technique is widely used in clinical examinations and medical diagnoses in recent years. For example, with the development of X-ray imaging technology, a C-shape X-ray imaging system has become more and more important in, such as, breast tomosynthesis, chest examination, or the like.

SUMMARY

An aspect of the present disclosure relates to a method for automatic brightness stabilization implemented on a computing device having one or more processors and one or more storage devices. The method may include obtaining image data of a target subject. The image data may be captured by an image capturing device. The target subject may be scanned by a medical imaging device with one or more first parameter values of one or more scan parameters and located at a first position relative to a detector of the medical imaging device. The method may further include detecting that the position of the target subject relative to the detector changes from the first position to a second position. The method may further include determining, based on the image data, a target equivalent thickness of the target subject with respect to the second position. And the method may also include determining, based on the target equivalent thickness, one or more second parameter values of the one or more scan parameters so as to achieve an automatic brightness stabilization.

In some embodiments, the method may further include causing the medical imaging device to scan the target subject at the second position relative to the detector with the one or more second parameter values of the one or more scan parameters to acquire the second medical image data.

In some embodiments, the determining, based on the image data, the target equivalent thickness of the target subject with respect to the second position may include generating a subject model representing the target subject based on the image data, and determining the target equivalent thickness of the target subject with respect to the second position based on the subject model.

In some embodiments, the subject model may include at least one of a 2-dimensional (2D) skeleton model, a 3-dimensional (3D) skeleton model, and/or a 3D mesh model.

In some embodiments, the determining, based on the target equivalent thickness, one or more second parameter values of the one or more scan parameters may include obtaining feature information of the target subject, and determining, based on the target equivalent thickness and the feature information of the target subject, the one or more second parameter values of the one or more scan parameters.

In some embodiments, the feature information of the target subject may include at least one of an attenuation coefficient, a position, and/or a density of a scan region of the target subject corresponding to the second position.

In some embodiments, the determining, based on the target equivalent thickness, one or more second parameter values of the one or more scan parameters may include determining, based on the target equivalent thickness, the one or more second parameter values of the one or more scan parameters using a scan parameter determination model.

In some embodiments, the scan parameter determination model may be generated according to a model training process. The model training process may include obtaining at least one training sample, each of which may include a sample equivalent thickness of a sample subject and one or more sample parameter values of the one or more scan parameters corresponding to the sample equivalent thickness, obtaining a preliminary model, and generating the scan parameter determination model by training the preliminary model using the at least one training sample.

In some embodiments, the determining, based on the target equivalent thickness, one or more second parameter values of the one or more scan parameters may include obtaining a relationship between an equivalent thickness and the one or more scan parameters, and determining, based on the target equivalent thickness and the relationship, the one or more second parameter values of the one or more scan parameters.

In some embodiments, the one or more scan parameters may include at least one of a voltage of a radiation source, a current of the radiation source, a distance between the radiation source and a detector, a radiation dose, a size of a focal spot, and/or a filtration of radiation rays.

Another aspect of the present disclosure relates to a method for monitoring a target subject during a scan of the target subject implemented on a computing device having at least one processor and at least one storage device. The method may include obtaining a plurality of sets of image data of the target subject. The target subject may be scanned by a medical imaging device. The plurality of sets of image data may be captured by an image capturing device during the scan of the target subject at a series of time points. Each of the plurality of sets of image data may correspond to one of the series of time points. The method may further include determining, based on the plurality of sets of image data, whether the target subject moves over the series of time points. And the method may also include in response to determining that the target subject moves over the series of time points, generating control information for adjusting the scan of the target subject.

In some embodiments, the plurality of sets of image data may include at least one of an RGB image, a depth image, and/or an infrared radiation (IR) image of the target subject.

In some embodiments, the determining, based on the plurality of sets of image data, whether the target subject moves over the series of time points may include for each of the plurality of sets of image data, identifying at least one feature point representing at least one body landmark of the target subject from the set of image data, determining, based on the at least one feature point identified in each of the plurality of sets of image data, a motion of the at least one body landmark over the series of time points, and determining, based on the motion of the at least one body landmark, whether the target subject moves over the series of time points.

In some embodiments, for each of the plurality of sets of image data, the identifying at least one feature point representing at least one body landmark of the target subject from the set of image data may include generating a first subject model representing the target subject based on the set of image data, and identifying, from the first subject model, the at least one feature point representing the at least one body landmark of the target subject.

In some embodiments, the first subject model may include at least one of a 2-dimensional (2D) skeleton model, a 3-dimensional (3D) skeleton model, and/or a 3D mesh model.

In some embodiments, the determining, based on the plurality of sets of image data, whether the target subject moves over the series of time points may include for each of the plurality of sets of image data, determining one or more parameter values of one or more posture parameters of the target subject based on the set of image data, and determining, based on the one or more parameter values of the one or more posture parameters of the target subject corresponding to each of the set of image data, whether the target subject moves over the series of time points.

In some embodiments, for each of the plurality of sets of image data, the determining one or more parameter values of one or more posture parameters of the target subject based on the set of image data may include generating a second subject model representing the target subject based on the set of image data, and determining the one or more parameter values of the one or more posture parameters of the target subject based on the second subject model.

In some embodiments, the second subject model may include at least one of a 2-dimensional (2D) skeleton model, a 3-dimensional (3D) skeleton model, and/or a 3D mesh model.

In some embodiments, the generating control information for adjusting the scan of the target subject may include causing a terminal device to generate a notification.

In some embodiments, the generating control information for adjusting the scan of the target subject may include causing the medical imaging device to terminate the scan of the target subject.

A further aspect of the present disclosure relates to a method for positioning a target subject to be scanned by a medical imaging device implemented on a computing device having one or more processors and one or more storage devices. The method may include obtaining image data indicative of the position of the target subject relative to one or more components of the medical imaging device. The image data may be captured by an image capturing device. The method may further include obtaining position information relating to the one or more components of the medical imaging device. And the method may also include determining a plurality of regions of the target subject based on the image data and the position information. Different regions of the plurality of regions may correspond to different positioning procedures of the target subject.

In some embodiments, the method may further include causing a terminal device to display a target image of the target subject with a plurality of annotations of the plurality of regions.

In some embodiments, the one or more components of the medical imaging device may include a scanning table that supports the target subject, and the plurality of regions may include a first region that can be imaged by the medical imaging device without moving the scanning table.

In some embodiments, the method may further include obtaining, via the terminal device, a first input associated with a first scan region of the target subject. The first scan region may be within the first region. And the method may further include causing the medical imaging device to scan the first scan region based on the first input.

In some embodiments, the one or more components of the medical imaging device may include a scanning table that supports the target subject, and the plurality of regions may include a second region that can be imaged by the medical imaging device by moving the scanning table.

In some embodiments, the method may further include obtaining, via the terminal device, a second input associated with a second scan region of the target subject. At least part of the second scan region may be within the second region. The method may further include determining a target position of the target subject based on the second input, the image data, and the position information, causing the scanning table to move the target subject to the target position, and causing the medical imaging device to scan the target subject when the target subject is at the target position.

In some embodiments, the plurality of regions may include a third region that cannot be imaged by the medical imaging device.

In some embodiments, the method may further include obtaining, via the terminal device, a third input associated with a third scan region of the target subject. At least part of the third scan region may be within the third region. And the method may further include generating a notification indicating that the third scan region cannot be imaged by the medical imaging device.

In some embodiments, the causing a terminal device to display a target image of the target subject with a plurality of annotations of the plurality of regions may include generating a subject model representing the target subject based on the image data, generating the target image by adding the plurality of annotations of the plurality of regions on the subject model, and causing the terminal device to display the target image.

In some embodiments, the plurality of annotations of the plurality of regions may be displayed in the target image in different colors and/or different textures.

In some embodiments, the one or more components of the medical imaging device may include a scanning table that supports the target subject and a supporting device that supports a detector and a radiation source of the medical imaging device. And the determining a plurality of regions of the target subject based on the image data and the position information may include determining feature information of the target subject based on the image data, determining the position of the target subject relative to the scanning table based on the image data, and determining the plurality of regions of the target subject based on the feature information of the target subject, the position of the target subject relative to the scanning table, and the position information of the scanning table and the supporting device.

A still further aspect of the present disclosure relates to a method for scan preparation implemented on a computing device having one or more processors and one or more storage devices. The method may include obtaining image data of a target subject to be scanned by a medical imaging device. The target subject may be supported by a scanning table of the medical imaging device. The image data may be captured by an image capturing device. The method may further include obtaining feature information of an operator of the medical imaging device. The method may further include determining, based on the image data and the feature information, a target position of the scanning table. And the method may also include causing the scanning table to move to the target position.

In some embodiments, the feature information of the operator may include a height of the operator.

In some embodiments, the obtaining feature information of an operator of the medical imaging device may include obtaining second image data of the operator, and determining the feature information of the operator based on the second image data.

In some embodiments, the determining, based on the image data and the feature information, a target position of the scanning table may include determining feature information of the target subject based on the image data, and determining the target position of the scanning table based on the feature information of the target subject and the feature information of the operator.

In some embodiments, the feature information of the target subject may include a thickness of the target subject.

In some embodiments, the determining feature information of the target subject based on the image data may include generating a subject model representing the target subject based on the image data, and determining the feature information of the target subject based on the subject model.

In some embodiments, the method may further include obtaining environment data, and determining, based on the environment data, whether an obstacle exists in a moving trajectory of the scanning table to the target position.

In some embodiments, the method may further include generating a notification in response to determining that an obstacle exists in the moving trajectory of the scanning table to the target position.

A still further aspect of the present disclosure relates to a method for determining a rotation scheme of a medical imaging device implemented on a computing device having one or more processors and one or more storage devices. The method may include obtaining image data of a target subject to be scanned by a medical imaging device. The medical imaging device may have an imaging isocenter located at a first position. The image data may be acquired by an image capturing device. The method may further include determining a second position of a point of interest (POI) of the target subject based on the image data, and determining a rotation scheme for the medical imaging device to adopt during the scan based on the first position of the imaging isocenter and the second position of the POI of the target subject.

In some embodiments, the determining a second position of a point of interest (POI) of the target subject based on the image data may include determining feature information of a scan region of the target subject based on the image data, and determining, based on the feature information, the second position of the POI.

In some embodiments, the determining feature information of a scan region of the target subject based on the image data may include generating a subject model based on the image data, determining, from the subject model, a target region corresponding to the scan region of the target subject, and determining the feature information of the scan region of the target subject based on the target region.

In some embodiments, the feature information of the scan region may include a thickness of the scan region.

In some embodiments, the target subject may be supported by a scanning table. And the determining, based on the feature information, the second position of the POI may include obtaining position information of the scanning table, and determining the second position of the POI based on the position information of the scanning table and the feature information of the scan region of the target subject.

In some embodiments, the determining a rotation scheme for the medical imaging device to adopt during the scan based on the first position of the imaging isocenter and the second position of the POI of the target subject may include determining whether the first position is coincident with the second position.

In some embodiments, the method may further include in response to determining that the first position is not coincident with the second position, causing the medical imaging device to adjust the imaging isocenter from the first position to the second position, and causing the medical imaging device to perform an isocentric rotation around the second position of the POI during the scan.

In some embodiments, the method may further include in response to determining that the first position is not coincident with the second position, causing the medical imaging device to perform a non-isocentric rotation around the second position of the POI during the scan.

In some embodiments, the method may further include in response to determining that the first position is coincident with the second position, causing the medical imaging device to perform an isocentric rotation around the second position of the POI during the scan.

A still further aspect of the present disclosure relates to a method for scan preparation implemented on a computing device having one or more processors and one or more storage devices. The method may include obtaining image data of a target subject to be scanned by a medical imaging device. The image data may be acquired by at least one image capturing device, and the medical imaging device may have an imaging isocenter. The method may further include determining, based on the image data, a scan region of the target subject. And the method may also include adjusting one or more components of the medical imaging device such that the scan region may be targeted by the imaging isocenter of the medical imaging device.

In some embodiments, the determining, based on the image data, a scan region of the target subject may include generating, based on the image data of the target subject, at least one display image of the target subject, causing a terminal device to display the at least one display image, and receiving, via the terminal device, a selection of the scan region of the target subject.

In some embodiments, the generating, based on the image data of the target subject, at least one display image of the target subject may include generating, based on the image data, a subject model representing the target subject, and generating, based on the subject model, the at least one display image of the target subject.

In some embodiments, the at least one display image may include a first image corresponding to a coronal plane of the target subject and a second image corresponding to a sagittal plane of the target subject.

In some embodiments, the generating, based on the subject model, the at least one display image of the target subject may include obtaining reference image data representing an internal structure of the target subject, generating a reference subject model representing the internal structure of the target subject by combining the reference image data and the subject model, and generating, based on the reference subject model, the at least one display image of the target subject.

In some embodiments, the method may further include determining a position of the target subject relative to the one or more components of the medical imaging device based on the image data, obtaining position information relating to the one or more components of the medical imaging device, and determining a plurality of regions of the target subject based on the position of the target subject relative to the one or more components and the position information relating to the one or more components. Different regions of the plurality of regions may correspond to different positioning procedures of the target subject.

In some embodiments, the generating, based on the image data, at least one display image may include for each of the at least one display image, generating the display image with a plurality of annotations of the plurality of regions.

In some embodiments, the one or more components of the medical imaging device may include a scanning table that supports the target subject, and the plurality of regions may include a first region that can be imaged by the medical imaging device without moving the scanning table.

In some embodiments, the scan region may be within the first region. The one or more components of the medical imaging device may include a supporting device that supports a detector and a radiation source of the medical imaging device. And the adjusting one or more components of the medical imaging device such that the scan region may be targeted by the imaging isocenter of the medical imaging device may include determining a target position of the supporting device based on the scan region, the image data, and the position information, and causing the supporting device to move to the target position such that the scan region may be targeted by the imaging isocenter of the medical imaging device.

In some embodiments, the one or more components of the medical imaging device may include a scanning table that supports the target subject, and the plurality of regions may include a second region that can be imaged by the medical imaging device by moving the scanning table.

In some embodiments, the scan region may be within the second region. The one or more components of the medical imaging device may include a supporting device that supports a detector and a radiation source of the medical imaging device. And the adjusting one or more components of the medical imaging device such that the scan region may be targeted by the imaging isocenter of the medical imaging device may include determining a target position of the target subject based on the scan region, the image data, and the position information, causing the scanning table to move to the target subject to the target position, determining a target position of the supporting device based on the target position of the target subject, the scan region, the image data, and the position information, and causing the supporting device to move to the target position such that the scan region may be targeted by the imaging isocenter of the medical imaging device.

In some embodiments, the plurality of regions may include a third region that cannot be imaged by the medical imaging device.

In some embodiments, the scan region may be within the third region. And the adjusting one or more components of the medical imaging device such that the scan region may be targeted by the imaging isocenter of the medical imaging device may include generating a notification indicating that the scan region cannot be imaged by the medical imaging device.

A still further aspect of the present disclosure relates to a method for scan preparation implemented on a computing device having one or more processors and one or more storage devices. The method may include obtaining image data of a target subject to be scanned by a medical imaging device. The image data may be captured by an image capturing device. The method may further include for each of one or more components of the medical imaging device, obtaining a planned trajectory of the component during a scan to be performed on the target subject. The method may further include performing a virtual scan on the target subject based on the image data and the planned trajectories of the one or more components of the medical imaging device. And the method may also include determining whether a collision is likely to occur between the target subject and the one or more components of the medical imaging device during the scan based on the virtual scan.

In some embodiments, the performing a virtual scan on the target subject based on the image data and the planned trajectories of the one or more components of the medical imaging device may include generating, based on the image data, a virtual imaging system that includes a first representation of the target subject and one or more second representations of the one or more components of the medical imaging device, and performing, using the virtual imaging system, the virtual scan on the first representation. During the virtual scan, each of the one or more second representations may move according to the planned trajectory of the corresponding component of the medical imaging device.

In some embodiments, the method may further include causing a terminal device to display the virtual scan performed using the virtual imaging system.

In some embodiments, the generating, based on the image data, a virtual imaging system that includes a first representation of the target subject and one or more second representations of the one or more components of the medical imaging device may include generating the first representation based on the image data, obtaining feature information of the one or more components of the medical imaging device, generating the one or more second representations based on the feature information of the one or more components, and generating the virtual imaging system based on the first representation and the one or more second representations.

In some embodiments, the generating the first representation based on the image data may include generating a subject model based on the image data, and generating the first representation based on the subject model.

In some embodiments, the determining whether a collision is likely to occur between the target subject and the one or more components based on the virtual scan may include for each of the one or more components, determining a distance between the second representation of the component and the first representation of the target subject during the virtual scan, and determining whether a collision is likely to occur between the target subject and the component based on the distance.

In some embodiments, the method may further include generating a notification in response to determining that a collision is likely to occur between the target subject and the one or more components of the medical imaging device.

In some embodiments, the method may further include causing the medical imaging device to perform the scan on the target subject in response to determining that a collision is not likely to occur between the target subject and the one or more components of the medical imaging device.

In some embodiments, the method may further include determining a posture of the target subject based on the image data.

In some embodiments, the method may further include determining at least one scan parameter relating to the scan based on the posture of the target subject and feature information of the target subject.

In some embodiments, the feature information of the target subject may include at least one of a width, a height, a thickness, and/or an attenuation value of the target subject or a portion of the target subject.

A still further aspect of the present disclosure relates to a method for scan preparation implemented on a computing device having one or more processors and one or more storage devices. The method may include obtaining image data of a target subject to be scanned by a medical imaging device. The image data may be acquired by an image capturing device, and the medical imaging device may have an imaging isocenter. The method may further include adjusting one or more components of the medical imaging device such that a scan region of the target subject may be targeted by the imaging isocenter of the medical imaging device. The method may further include for each of the one or more components of the medical imaging device, obtaining a planned trajectory of the component during a scan to be performed on the target subject. And the method may also include determining whether a collision is likely to occur between the target subject and the one or more components of the medical imaging device by performing a virtual scan on the target subject based on the image data and the planned trajectories of the one or more components of the medical imaging device.

In some embodiments, the method may further include generating, based on the image data of the target subject, at least one display image of the target subject, causing a terminal device to display the at least one display image, and receiving, via the terminal device, a selection of the scan region of the target subject.

In some embodiments, the generating, based on the image data of the target subject, at least one display image of the target subject may include generating, based on the image data, a subject model representing the target subject, and generating, based on the subject model, the at least one display image of the target subject.

In some embodiments, the determining whether a collision is likely to occur between the target subject and the one or more components of the medical imaging device by performing a virtual scan on the target subject based on the image data and the planned trajectories of the one or more components of the medical imaging device may include generating, based on the image data, a virtual imaging system that may include a first representation of the target subject and one or more second representations of the one or more components of the medical imaging device, performing, using the virtual imaging system, the virtual scan on the first representation. During the virtual scan, each of the one or more second representations may be moved according to the planned trajectory of the corresponding component of the medical imaging device. And the determining whether a collision is likely to occur between the target subject and the one or more components of the medical imaging device by performing a virtual scan on the target subject based on the image data and the planned trajectories of the one or more components of the medical imaging device may also include determining whether a collision is likely to occur between the target subject and the one or more components of the medical imaging device during the scan based on the virtual scan.

In some embodiments, the generating, based on the image data, a virtual imaging system that include may include a first representation of the target subject and one or more second representations of the one or more components of the medical imaging device may include generating the first representation based on the image data, obtaining feature information of the one or more components of the medical imaging device, generating the one or more second representation based on the feature information of the one or more components, and generating the virtual imaging system based on the first representation and the one or more second representations.

In some embodiments, the generating the first representation based on the image data may include generating a subject model based on the image data, and generating the first representation based on the subject model.

In some embodiments, the determining whether a collision is likely to occur between the target subject and the one or more components based on the virtual scan may include for each of the one or more components, determining a distance between the second representation of the component and the first representation of the target subject during the virtual scan, and determining whether a collision is likely to occur between the target subject and the component based on the distance.

In some embodiments, the method may further include generating a notification in response to determining that a collision is likely to occur between the target subject and the one or more components of the medical imaging device.

In some embodiments, the method may further include causing the medical imaging device to perform the scan on the target subject in response to determining that a collision is not likely to occur between the target subject and the one or more components of the medical imaging device.

In some embodiments, the method may further include determining a posture of the target subject based on the image data.

In some embodiments, the method may further include determining at least one scan parameter relating to the scan based on the posture of the target subject and feature information of the target subject.

In some embodiments, the feature information of the target subject may include at least one of a width, a height, a thickness, and/or an attenuation value of the target subject or a portion of the target subject.

A still further aspect of the present disclosure relates to a method for collision avoidance implemented on a computing device having one or more processors and one or more storage devices. The method may include obtaining image data of a plurality of subjects in an examination room. The image data may be captured by an image capturing device mounted in the examination room. The plurality of subjects may include a first subject and a second subject. And the method may further include determining, based on the image data, whether a collision is likely to occur between the first subject and the second subject.

In some embodiments, the image data may include a plurality of sets of image data corresponding to a plurality of time points.

In some embodiments, the determining, based on the image data, whether a collision is likely to occur between the first subject and the second subject may include determining, based on the plurality of sets of image data, a first trajectory of the first subject, determining, based on the plurality of sets of image data, a second trajectory of the second subject, and determining, based on the first trajectory and the second trajectory, whether a collision is likely to occur between the first subject and the second subject.

In some embodiments, the determining, based on the plurality of sets of image data, a first trajectory of the first subject may include for each of the plurality of sets of image data, determining, based on the set of image data, a position of the first subject at the time point corresponding to the set of image data, and determining, based on the positions of the first subject at the plurality of time points, the first trajectory of the first subject.

In some embodiments, the determining, based on the image data, whether a collision is likely to occur between the first subject and the second subject may include determining, based on the image data, a distance between the first subject and the second subject, determining whether the distance between the first subject and the second subject is less than a first distance threshold, and in response to determining that the distance between the first subject and the second subject is less than the first distance threshold, determining that a collision is likely to occur between the first subject and the second subject.

In some embodiments, the method may further include determining the first distance threshold based on the image data.

In some embodiments, the method may further include determining whether the distance between the first subject and the second subject is less than a second distance threshold. The second distance threshold may be smaller than the first distance threshold. The method may further include in response to determining that the distance between the first subject and the second subject is less than the second distance threshold, generating a control signal to stop a movement of at least one of the first subject or the second subject.

In some embodiments, the method may further include determining the second distance threshold based on the image data.

In some embodiments, the method may further include in response to determining that a collision is likely to occur between the first subject and the second subject, generating a control signal to decelerate at least one of the first subject or the second subject.

In some embodiments, the method may further include causing an instruction to be generated based on the image data. The instruction may be configured for guiding a user to control a movement of at least one of the first subject or the second subject.

In some embodiments, the method may further include identifying, based on the image data, the plurality of subjects, obtaining feature information relating to each of the plurality of subjects, and selecting, from the plurality of subjects, at least two subjects to be monitored based on the feature information. The at least two selected subjects may at least include the first subject and the second subject.

In some embodiments, the plurality of subjects may at least include a target subject to be examined by a medical device and one or more components of the medical device.

A still further aspect of the present disclosure relates to a method for medical imaging implemented on a computing device having one or more processors and one or more storage devices. The method may include obtaining image data of a target subject being scanned by a medical imaging device. The image data may be captured by an image capturing device. The method may further include during the scan of the target subject, detecting that a position of the target subject relative to a detector of the medical imaging device changes from a first subject position to a second subject position, determining, based on the image data of the target subject, feature information of a scan region of the target subject corresponding to the second subject position, determining, based on the feature information of the scan region, one or more movement parameters of the detector, causing the detector to move from a first position to a second position according to the one or more movement parameters, and causing the medical imaging device to scan the scan region when the detector is located at the second position.

In some embodiments, the determining, based on the image data of the target subject, feature information of the scan region of the target subject corresponding to the second subject position may include identifying, in the image data, a target region corresponding to the scan region, and determining, based on the target region, a thickness of the scan region.

In some embodiments, the determining, based on the feature information of the scan region, one or more movement parameters of the detector may include obtaining a target distance between the detector and the target subject, and determining the one or more movement parameters of the detector based on the target distance and the thickness of the scan region.

In some embodiments, the obtaining a target distance between the detector and the target subject may include determining, based on the image data of the target subject, a thickness of the scan region corresponding to the first subject position, and determining, based on the thickness of the scan region corresponding to the first subject position and the first position of the detector, the target distance.

In some embodiments, the one or more movement parameters may include at least one of a moving distance and/or a moving direction.

In some embodiments, the causing the detector to move from the first position to a second position according to the one or more movement parameters of the detector may include determining whether a collision is likely to occur between the target subject and the detector, and in response to determining that a collision is likely to occur, adjusting at least one of the one or more moving parameters.

In some embodiments, the determining whether a collision is likely to occur between the target subject and the detector may include determining an estimated trajectory from the first position to the second position, and determining, based on the second subject position and the estimated trajectory, whether a collision is likely to occur between the target subject and the detector.

In some embodiments, the medical imaging device may be a computed tomography scanner or a digital radiography scanner.

In some embodiments, the method may further include transmitting information associated with the second position to a terminal device, and obtaining a user input regarding the second position from the terminal device.

In some embodiments, the information associated with the second position may be in the form of a display image illustrating the detector located at the second position and the target subject located at the second subject position.

A still further aspect of the present disclosure relates to a method for dose estimation implemented on a computing device having one or more processors and one or more storage devices. The method may include obtaining image data of a plurality of subjects in an examination room. The plurality of subjects may at least include a target subject. The image data may be captured by an image capturing device mounted in the examination room during a scan or a treatment of the target subject performed by a medical device. The target subject may be irradiated by a radiation source of the medical device. The method may further include obtaining one or more parameter values of one or more radiation parameters of the radiation source. And the method may also include estimating a dose distribution in the examination room based on the image data and the one or more parameter values.

In some embodiments, the dose distribution in the examination room may be estimated using at least one of a Monte Carlo algorithm, a greedy algorithm, a dynamic programming algorithm, a divide-and-conquer algorithm, a backtracking algorithm, a branch bound algorithm, a pencil beam algorithm, and/or a cone convolution algorithm.

In some embodiments, the estimating a dose distribution in the examination room may include for each radiation particle of a plurality of radiation particles emitted by the radiation source, simulating, based on the image data and the one or more parameter values, a transport process of the radiation particle in the examination room, and estimating, based on the transport process of each radiation particle, the dose distribution in the examination room.

In some embodiments, the estimating a dose distribution in the examination room based on the image data and the one or more parameter values may include for each of the plurality of subjects, determining, based on the image data, position information of the subject, and obtaining feature information of the subject, and estimating the dose distribution in the examination room based on the position information of each of the plurality of subjects, the feature information of each of the plurality of subjects, and the one or more parameter values.

In some embodiments, for each of the plurality of subjects, the feature information may include at least one of a shape, a height, a width, a thickness, and/or an attenuation coefficient.

In some embodiments, for each of the plurality of subjects, the determining, based on the image data, the position information of the subject may include obtaining a subject model representing the target subject, identifying, in the subject model, one or more regions corresponding to one or more portions of the target subject, and determining, based on the image data and the one or more regions, position information of each of the one or more portions of the target subject.

In some embodiments, the dose distribution in the examination room may include a dose delivered to each of the one or more portions of the target subject. And the estimating the dose distribution in the examination room may include for each of the one or more portions of the target subject, estimating the dose delivered to the portion of the target subject based on the position information related to the portion of the target subject, the feature information of each of the plurality of subjects, and the one or more parameter values.

In some embodiments, the method may further include for each of the one or more portions of the target subject, estimating an absorbed dose that is absorbed by the portion of the target subject based on the dose delivered to the portion of the subject and the feature information of the portion.

In some embodiments, the method may further include determining, based on the dose distribution, whether the scan or the treatment of the target subject needs to be adjusted.

In some embodiments, the dose distribution may include a dose delivered to the target subject. And the determining, based on the dose distribution, whether the scan or the treatment of the target subject needs to be adjusted may include obtaining a dose delivery threshold related to the target subject, determining whether the dose delivered to the target subject exceeds the dose delivery threshold, and in response to determining that the dose delivered to the target subject exceeds the dose delivery threshold, determining that the scan or the treatment of the target subject may need to be adjusted.

In some embodiments, the method may further include causing a notification to be generated. The notification may be configured to notify an operator of the scan or the treatment that the scan or the treatment of the target subject may need to be adjusted.

In some embodiments, the plurality of subjects may include an operator of the scan or the treatment.

In some embodiments, the method may further include determining, based on the dose distribution in the examination room, a recommended operating region for the operator to manipulate the scan or the treatment, and causing a notification regarding the recommended operating region to be generated.

In some embodiments, the method may further include obtaining at least one measured dose each of which may be measured by a dosimeter at a position in the examination room, determining, based on the at least one measured dose, a correction parameter relating to the dose distribution, and correcting the dose distribution using the correction parameter.

In some embodiments, the one or more radiation parameters may include at least one of a voltage of the radiation source, a current of the radiation source, a radiation duration, an irradiation angle, a position of the radiation source, a position of a detector of the medical device, and/or a shape of a radiation beam emitted by the radiation source.

In some embodiments, the method may further include causing a terminal device to display the dose distribution.

In some embodiments, the method may further include generating, based on the dose distribution and the image data, a dose distribution map of the examination room.

A still further aspect of the present disclosure relates to a method for medical imaging implemented on a computing device having one or more processors and one or more storage devices. The method may include obtaining image data of a target subject to be scanned by a medical imaging device. The image data of the target subject may be captured by an image capturing device. The method may further include obtaining reference image data representing an internal structure of the target subject. The method may further include obtaining one or more parameter values of one or more scan parameters of the medical imaging device relating to the scan to be performed on the target subject. And the method may also include generating a target image representing an internal structure of a scan region of the target subject to be scanned by the medical imaging device under the one or more parameter values based on the image data, the reference image data, and the one or more parameter values.

In some embodiments, the reference image data may include a historical anatomical image acquired by a historical scan on the target subject.

In some embodiments, the reference image data may include a reference anatomical image of a reference subject.

In some embodiments, the generating a target image representing an internal structure of a scan region of the target subject may include generating a reference subject model representing the internal structure of the target subject based on the image data and the reference image data, and generating the target image based on the reference subject model and the one or more parameter values.

In some embodiments, the generating a reference subject model representing the internal structure of the target subject based on the image data and the reference image data may include generating a subject model representing the target subject based on the image data, and generating the reference subject model based on the subject model and the reference image data.

In some embodiments, the generating the target image based on the reference subject model and the one or more parameter values of the one or more scan parameters of the medical imaging device may include generating a target subject model by transforming the reference subject model based on the one or more parameter values, determining, in the target subject model, a target region corresponding to a field of view (FOV) of the medical imaging device based on the one or more parameter values. The FOV may cover the scan region of the target subject. And the generating the target image based on the reference subject model and the one or more parameter values of the one or more scan parameters of the medical imaging device may further include generating, based on the target region of the target subject model, the target image.

In some embodiments, the method may further include causing a terminal device to jointly display the target image and the target subject model.

In some embodiments, the method may further include adding an annotation regarding the target region to the target subject model, and causing a terminal device to display the target subject model with the annotation.

In some embodiments, the method may further include detecting that at least one of the one or more parameter values is adjusted, and updating the target image based on the at least one adjusted parameter value.

In some embodiments, the updating the target image based on the at least one adjusted parameter value may include updating the target region by adjusting, based on the at least one adjusted parameter value, at least one of a position of the target region in the target subject model, a size of the target region, and/or a shape of the target region, and updating the target image based on the updated target region.

In some embodiments, the adjustment of the at least one of the one or more parameter values may cause a change in a position of the target subject of the medical imaging device without changing a scanning angle of the medical imaging device. And the updating the target image may include updating the target region by adjusting, based on the at least one adjusted parameter value, a position of the target region in the target subject model, and updating the target image based on the updated target region.

In some embodiments, the adjustment of the at least one of the one or more parameter values may cause a change in a position of a radiation source of the medical imaging device without changing a scanning angle of the medical imaging device. And the updating the target image may include updating the target region by adjusting, based on the at least one adjusted parameter value, a position of the target region in the target subject model, and updating the target image based on the updated target region.

In some embodiments, the adjustment of the at least one of the one or more parameter values may cause a change in a size of the FOV of the medical imaging device. And the updating the target image may include updating the target region by adjusting, based on the at least one adjusted parameter value, a size of the target region, and updating the target image based on the updated target region.

In some embodiments, the adjustment of the at least one of the one or more parameter values may cause a change in a shape of the FOV of the medical imaging device. And the updating the target image may include updating the target region by adjusting, based on the at least one adjusted parameter value, a shape of the target region, and updating the target image based on the updated target region.

In some embodiments, the adjustment of the at least one of the one or more parameter values may cause a change in a scanning angle of the medical imaging device. And the updating the target image may include updating the target subject model based on the changed scanning angle, updating the target region based on the updated target subject model, and updating the target image based on the updated target region.

In some embodiments, the one or more scan parameters of the medical imaging device may include at least one of a scanning angle, a position of a radiation source, a position of a scanning table, an inclination angle of the scanning table, a position of a detector, a gantry angle of a gantry, a size of a field of view (FOV), and/or a shape of a collimator.

A still further aspect of the present disclosure relates to a method for medical imaging implemented on a computing device having one or more processors and one or more storage devices. The method may include obtaining image data of a target subject to be scanned by a first medical imaging device. The image data of the target subject may be captured by an image capturing device. The method may further include obtaining reference image data representing an internal structure of the target subject. And the method may also include generating, based on the reference image data and the image data, a reference subject model representing the internal structure of the target subject.

In some embodiments, the reference image data may include a historical anatomical image acquired by the first medical imaging device or a second medical imaging device during a historical scan of the target subject.

In some embodiments, the second medical imaging device may include at least one of a computed tomography (CT) imaging device, a magnetic resonance (MR) imaging device, a positron emission computed tomography (PET) imaging device, and/or an ultrasound imaging device.

In some embodiments, the reference image data may include a reference anatomical image of a reference subject.

In some embodiments, the generating, based on the reference image data and the image data, the reference subject model representing the internal structure of the target subject may include generating, based on the image data, a subject model representing the subject, and generating the reference subject model based on the subject model and the reference image data.

In some embodiments, the subject model may include at least one of a 2-dimensional (2D) skeleton model, a 3-dimensional (3D) skeleton model, and/or a 3D mesh model.

In some embodiments, the generating the reference subject model based on the subject model and the reference image data may include identifying, in the subject model, one or more first regions each of which corresponds to one of one or more regions of interest (ROIs) of the target subject, identifying, in the reference image data, one or more second regions each of which corresponds to one of the one or more ROIs of the target subject, and generating the reference subject model based on the one or more first regions and the one or more second regions.

In some embodiments, the generating the reference subject model by combining the subject model and the reference image data may include determining, based on the subject model, one or more first values of one or more contour parameters of the target subject, determining, based on the reference image data, one or more second values of the one or more contour parameters of the target subject, and generating the reference subject model based on the one or more first values and the one or more second values.

In some embodiments, the one or more contour parameters may include at least one of a height, a width, and/or a thickness.

In some embodiments, the method may further include causing the first medical imaging device to perform a scan on the target subject based on the reference subject model.

In some embodiments, the causing the first medical imaging device to perform the scan on the target subject based on the reference subject model may include identifying, in the reference subject model, a region corresponding to a scan region of the target subject to be scanned by the first medical imaging device, adjusting one or more components of the first medical imaging device such that the scan region may be targeted by an imaging isocenter of the first medical imaging device, and causing the first medical imaging device to scan the scan region of the target subject.

In some embodiments, the method may further include obtaining one or more parameter values of one or more scan parameters of the first medical imaging device relating to the scan to be performed on the target subject, and generating a target image representing an internal structure of the scan region of the target subject to be scanned by the first medical imaging device under the one or more parameter values based on the reference subject model and the one or more parameter values.

A still further aspect of the present disclosure relates to a method for examining a target subject implemented on a computing device having one or more processors and one or more storage devices. The method may include obtaining image data of the target subject captured by an image capturing device. The method may further include obtaining first medical image data of the target subject. The first medical image data may be acquired with a first imaging modality before the examination of the target subject. The method may further include obtaining second medical image data of the target subject. The second medical image data may be acquired with a second imaging modality during the examination of the target subject. And the method may also include generating a composite image of the target subject by combining the first medical image data and the second medical image data based on the image data.

In some embodiments, the first imaging modality may include at least one of a computed tomography (CT) imaging, a magnetic resonance (MR) imaging, a positron emission computed tomography (PET) imaging, and/or an ultrasound imaging.

In some embodiments, the second imaging modality may include an X-ray imaging.

In some embodiments, the generating a composite image of the target subject by combining the first medical image data and the second medical image data based on the image data may include generating registered first medical image data by registering the first medical image data with the image data, and generating the composite image by combining the registered first medical image data and the second medical image data.

In some embodiments, the method may further include causing a terminal device to display the composite image.

In some embodiments, the examination of target subject may include a treatment of the target subject implemented by an invasive device.

In some embodiments, the invasive device may include a needle, a guide wire, a sheath, an endoscopy, a laparoscopy, an arthroscopy, a sucker, and/or a catheter.

In some embodiments, the first medical image data may include an angiographic image.

In some embodiments, the second medical image data may include a fluoroscopy of the target subject.

A still further aspect of the present disclosure relates to a method for motion correction in medical imaging implemented on a computing device having one or more processors and one or more storage devices. The method may include acquiring a plurality of medical images of a target subject by performing a scan on the target subject using a medical imaging device. The method may further include obtaining a plurality of sets of image data of the target subject. The plurality of sets of image data may be captured by an image capturing device during the scan of the target subject at a series of time points. Each of the plurality of sets of image data may correspond to one of the series of time points. The method may further include detecting, based on the plurality of sets of image data, a motion of the target subject. And the method may also include generating, based on the plurality of medical images, a target image of the target subject. Motion correction may be performed based on the detected motion of the target subject during the generation of the target image.

In some embodiments, the medical imaging device may include an X-ray imaging device.

In some embodiments, the detecting, based on the plurality of sets of image data, the motion of the target subject may include for each of the plurality of sets of image data, identifying at least one feature point representing at least one body landmark of the target subject from the set of image data, determining, based on the at least one feature point identified in each of the plurality of sets of image data, a motion of the at least one body landmark over the series of time points, and determining the motion of the target subject based on the motion of the at least one body landmark over the series of time points.

In some embodiments, the plurality of medical images may include a first medical image acquired before a contrast agent is injected into the target subject and a second medical image acquired after the contrast agent is injected into the target subject.

In some embodiments, the generating, based on the plurality of medical images, a target image of the target subject may include generating a corrected first medical image by correcting the first medical image based on the motion of the target subject, and generating, based on the corrected first medical image and the second medical image, the target image representing blood vessels of the target subject.

In some embodiments, the plurality of medical images may include a third medical image captured before an invasive device is inserted into the target subject and a fourth medical image acquired after the invasive device is inserted into the target subject.

In some embodiments, the generating, based on the plurality of medical images, a target image of the target subject may include generating a corrected third medical image by correcting the third medical image based on the motion of the target subject, and generating, based on the corrected third medical image and the fourth medical image, the target image representing the invasive device within the target subject.

In some embodiments, the method may further include obtaining a reference image representing blood vessels of the target subject, and generating a composite image representing the invasive device within the blood vessels of the target subject based on the reference image and the target image.

In some embodiments, the generating a composite image representing the invasive device within the blood vessels of the target subject based on the reference image, the corrected third medical image, and the fourth medical image may include generating a target reference image by transforming the reference image, and generating the composite image by combining the target reference image and the target image.

In some embodiments, the method may further include obtaining a reference subject model representing an internal structure of the target subject, generating a corrected reference subject model by correcting the reference subject model based on the motion of the target subject, and generating the target image of the target subject by combining the corrected reference subject model and at least one of the plurality of medical images of the target subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 7 is a flowchart illustrating an exemplary process for positioning a target subject to be scanned by a medical imaging device according to some embodiments of the present disclosure;

FIG. 8 is a schematic diagram illustrating an exemplary target image 800 of a patient according to some embodiments of the present disclosure;

FIG. 16C is a schematic diagram illustrating an exemplary process for determining a POI of a target subject according to some embodiments of the present disclosure;

FIG. 17 is a flowchart illustrating an exemplary process for scan preparation according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
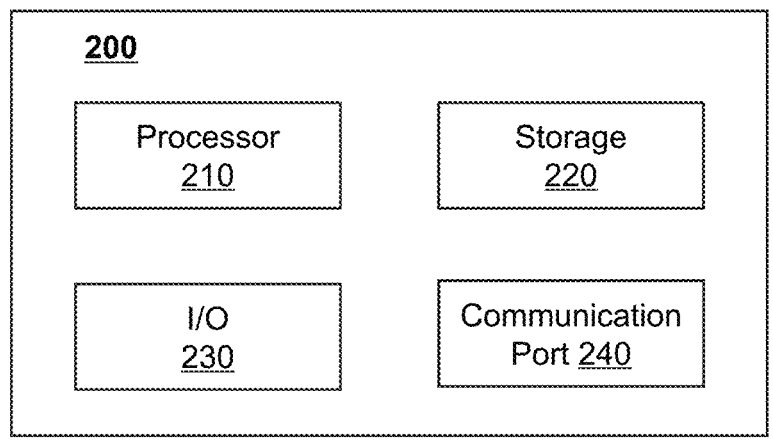
FIG. 2 is a schematic diagram illustrating exemplary hardware and/or software components of a computing device 200 according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., a processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "region," "location," and "area" in the present disclosure may refer to a location of an anatomical structure shown in the image or an actual location of the anatomical structure existing in or on a target subject's body, since the image may indicate the actual location of a certain anatomical structure existing in or on the target subject's body. The term "an image of a subject" may be referred to as the subject for brevity. Segmentation of an image of a subject may be referred to as segmentation of the subject.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

A conventional medical imaging procedure often involves a lot of human intervention. Merely by way of example, a user (e.g., a doctor, an operator, a technician, etc.) may need to manually perform a scan preparation before a scan of a target subject, which involves, for example, selecting and/or checking a scan region, adjusting position(s) of component(s) of a medical imaging device, setting one or more scan parameters, positioning the target subject, checking and/or adjusting a position and/or a posture of the target subject, determining a rotation scheme of the medical imaging device, or the like. In addition, the user may need to monitor and/or adjust the scan by, for example, monitoring whether the target subject moves during the scan, adjusting the position of one or more components of the medical imaging device, or the like, or any combination thereof. Such a medical imaging procedure may be inefficient and/or susceptible to human errors or subjectivity. Thus, it may be desirable to develop systems and methods for automated scan preparation and real-time monitoring and/or adjustment in medical imaging, thereby improving the imaging efficiency and/or accuracy. The terms "automatic" and "automated" are used interchangeably referring to methods and systems that analyze information and generates results with little or no direct human intervention.

The present disclosure may provide systems and methods for automated scan preparation and real-time monitoring/adjustment in medical imaging. According to some embodiments of the present disclosure, a plurality of scan preparation operations and a plurality of real-time monitoring/adjustment operations may be performed automatically or semi-automatically. The plurality of scan preparation operations may include positioning a target subject to be scanned by a medical imaging device, determining a rotation scheme of the medical imaging device, targeting a scan region of the target subject with an imaging isocenter of the medical imaging device, determining target position(s) of component(s) (e.g., a scanning table, a detector, a radiation source) of the medical imaging device, performing a virtual scan, generating a reference subject model representing an internal structure of the target subject, or the like, or any combination thereof. The plurality of real-time monitoring/adjustment operations may include achieving automatic brightness stabilization, monitoring a posture of the target subject, adjusting the position of component(s) of the medical imaging device, estimating a dose distribution, monitoring a treatment of the target subject, performing a motion correction, or the like, or any combination thereof. Compared with a conventional scan preparation and monitoring/adjustment operation during the scan which involve a lot of human intervention, the systems and methods of the present disclosure may be implemented with reduced or minimal or without user intervention, which is more efficient and accurate by, e.g., reducing the workload of a user, cross-user variations, and the time needed for the scan preparation and the monitoring/adjustment during the scan.

Figure 1:
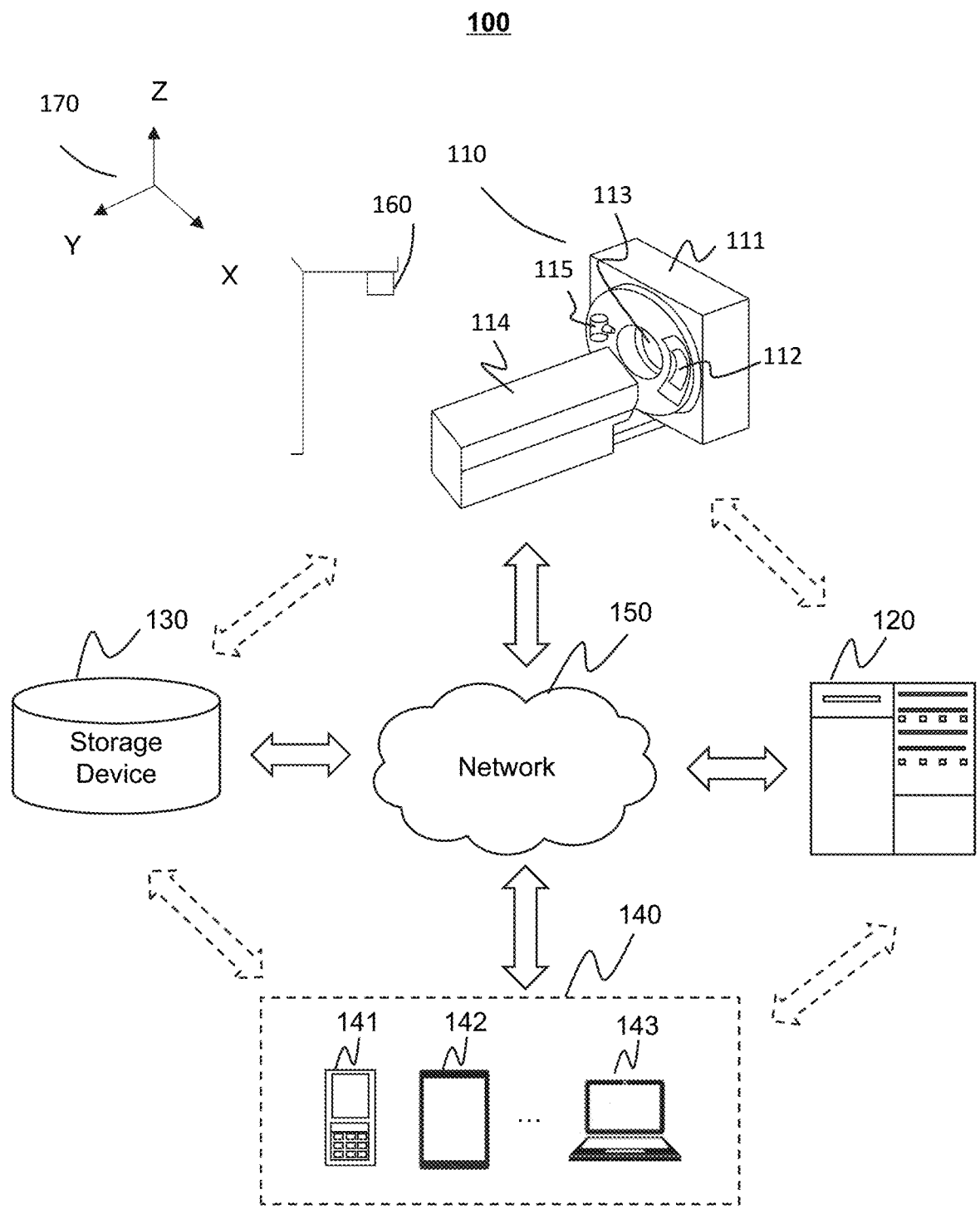
FIG. 1 is a schematic diagram illustrating an exemplary imaging system 100 according to some embodiments of the present disclosure.

FIG. 1 is a schematic diagram illustrating an exemplary imaging system 100 according to some embodiments of the present disclosure. As shown, the imaging system 100 may include a medical imaging device 110, a processing device 120, a storage device 130, one or more terminals 140, a network 150, and an image capturing device 160. In some embodiments, the medical imaging device 110, the processing device 120, the storage device 130, the terminal(s) 140, and/or the image capturing device 160 may be connected to and/or communicate with each other via a wireless connection, a wired connection, or a combination thereof. The connection between the components of the imaging system 100 may be variable. Merely by way of example, the medical imaging device 110 may be connected to the processing device 120 through the network 150 or directly. As a further example, the storage device 130 may be connected to the processing device 120 through the network 150 or directly.

The medical imaging device 110 may generate or provide image data related to a target subject via scanning the target subject. For illustration purposes, image data of a target subject acquired using the medical imaging device 110 is referred to as medical image data, and image data of the target subject acquired using the image capturing device 160 is referred to as image data. In some embodiments, the target subject may include a biological subject and/or a non-biological subject. For example, the target subject may include a specific portion of a body, such as the head, the thorax, the abdomen, or the like, or a combination thereof. As another example, the target subject may be a man-made composition of organic and/or inorganic matters that are with or without life. In some embodiments, the imaging system 100 may include modules and/or components for performing imaging and/or related analysis. In some embodiments, the medical image data relating to the target subject may include projection data, one or more images of the target subject, etc. The projection data may include raw data generated by the medical imaging device 110 by scanning the target subject and/or data generated by a forward projection on an image of the target subject.

In some embodiments, the medical imaging device 110 may be a non-invasive biomedical medical imaging device for disease diagnostic or research purposes. The medical imaging device 110 may include a single modality scanner and/or a multi-modality scanner.

The single modality scanner may include, for example, an ultrasound scanner, an X-ray scanner, an computed tomography (CT) scanner, a magnetic resonance imaging (MRI) scanner, an ultrasonography scanner, a positron emission tomography (PET) scanner, an optical coherence tomography (OCT) scanner, an ultrasound (US) scanner, an intravascular ultrasound (IVUS) scanner, a near infrared spectroscopy (NIRS) scanner, a far infrared (FIR) scanner, or the like, or any combination thereof. The multi-modality scanner may include, for example, an X-ray imaging-magnetic resonance imaging (X-ray-MRI) scanner, a positron emission tomography-X-ray imaging (PET-X-ray) scanner, a single photon emission computed tomography-magnetic resonance imaging (SPECT-MRI) scanner, a positron emission tomography-computed tomography (PET-CT) scanner, a digital subtraction angiography-magnetic resonance imaging (DSA-MRI) scanner, etc. It should be noted that the scanner described above is merely provided for illustration purposes, and not intended to limit the scope of the present disclosure. The term "imaging modality" or "modality" as used herein broadly refers to an imaging method or technology that gathers, generates, processes, and/or analyzes imaging information of a target subject.

For illustration purposes, the present disclosure mainly describes systems and methods relating to an X-ray imaging system. It should be noted that the X-ray imaging system described below is merely provided as an example, and not intended to limit the scope of the present disclosure. The systems and methods disclosed herein may be applied to any other imaging systems.

In some embodiments, the medical imaging device 110 may include a gantry 111, a detector 112, a detection region 113, a scanning table 114, and a radiation source 115. The gantry 111 may support the detector 112 and the radiation source 115. The target subject may be placed on the scanning table 114 and moved into the detection region 113 to be scanned. In some embodiments, the scanning table 114 may be configured to rotate and/or translate along different directions to move the target subject to a desired position. For example, the scanning table 114 may be configured to translate along or rotate about one or more of an X-axis, a Y-axis, and a Z-axis of a coordinate system 170 as shown in FIG. 1. The radiation source 115 may emit radioactive rays to the target subject. The radioactive rays may include a particle ray, a photon ray, or the like, or a combination thereof. In some embodiments, the radioactive rays may include a plurality of radiation particles (e.g., neutrons, protons, electron, p-mesons, heavy ions), a plurality of radiation photons (e.g., X-ray, y-ray, ultraviolet, laser), or the like, or a combination thereof. The detector 112 may detect radiation and/or a radiation event (e.g., gamma photons) emitted from the detection region 113. In some embodiments, the detector 112 may include a plurality of detector units. The detector units may include a scintillation detector (e.g., a cesium iodide detector) or a gas detector. The detector unit may be a single-row detector or a multi-rows detector.

In some embodiments, the medical imaging device 110 may be or include an X-ray imaging device, for example, a computed tomography (CT) scanner, a digital radiography (DR) scanner (e.g., a mobile digital radiography), a digital subtraction angiography (DSA) scanner, a dynamic spatial reconstruction (DSR) scanner, an X-ray microscopy scanner, a multimodality scanner, etc. For example, the X-ray imaging device may include a supporting device, an X-ray source, and a detector. The supporting device may be configured to support the X-ray source and/or the detector. The X-ray source may be configured to emit X-rays toward the target subject to be scanned. The detector may be configured to detect X-rays passing through the target subject. In some embodiments, the X-ray imaging device may be, for example, a C-shape X-ray imaging device, an upright X-ray imaging device, a suspended X-ray imaging device, or the like.

The processing device 120 may process data and/or information obtained from the medical imaging device 110, the storage device 130, the terminal(s) 140, and/or the image capturing device 160. For example, the processing device 120 may implement an automated scan preparation for a scan to be performed on a target subject. As another example, the processing device 120 may implement a real-time monitoring and/or adjustment during the scan of the target subject. More descriptions regarding the automated scan preparation and the real-time monitoring and/or adjustment may be found elsewhere in the present disclosure. See, e.g., FIG. 4 and relevant descriptions thereof.

In some embodiments, the processing device 120 may be a single server or a server group. The server group may be centralized or distributed. In some embodiments, the processing device 120 may be local to or remote from the imaging system 100. For example, the processing device 120 may access information and/or data from the medical imaging device 110, the storage device 130, the terminal(s) 140, and/or the image capturing device 160 via the network 150. As another example, the processing device 120 may be directly connected to the medical imaging device 110, the terminal(s) 140, the storage device 130, and/or the image capturing device 160 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

In some embodiments, the processing device 120 may include one or more processors (e.g., single-core processor(s) or multi-core processor(s)). Merely by way of example, the processing device 120 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 130 may store data, instructions, and/or any other information. In some embodiments, the storage device 130 may store data obtained from the processing device 120, the terminal(s) 140, the medical imaging device 110, and/or the image capturing device 160. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components of the imaging system 100 (e.g., the processing device 120, the terminal(s) 140). One or more components of the imaging system 100 may access the data or instructions stored in the storage device 130 via the network 150. In some embodiments, the storage device 130 may be part of the processing device 120.

The terminal(s) 140 may enable user interaction between a user and the imaging system 100. For example, the terminal(s) 140 may display a target image of the target subject with a plurality of annotations of a plurality of regions of the target subject. As another example, the terminal(s) 140 may display a virtual scan performed using a virtual imaging system. In some embodiments, the terminal(s) 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 140 may include an input device, an output device, etc. In some embodiments, the terminal(s) 140 may be part of the processing device 120.

The network 150 may include any suitable network that can facilitate the exchange of information and/or data for the imaging system 100. In some embodiments, one or more components of the imaging system 100 (e.g., the medical imaging device 110, the processing device 120, the storage device 130, the terminal(s) 140) may communicate information and/or data with one or more other components of the imaging system 100 via the network 150. For example, the processing device 120 may obtain medical image data from the medical imaging device 110 via the network 150. As another example, the processing device 120 may obtain user instruction(s) from the terminal(s) 140 via the network 150.

The network 150 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

The image capturing device 160 may be configured to capture image data of the target subject before, during, and/or after the medical imaging device 110 performs a scan on the target subject. The image capturing device 160 may be and/or include any suitable device that is capable of capturing image data of the target subject. For example, the image capturing device 160 may include a camera (e.g., a digital camera, an analog camera, etc.), a red-green-blue (RGB) sensor, an RGB-depth (RGB-D) sensor, or another device that can capture color image data of the target subject. As another example, the image capturing device 160 may be used to acquire point-cloud data of the target subject. The point-cloud data may include a plurality of data points, each of which may represent a physical point on a body surface of the target subject and can be described using one or more feature values of the physical point (e.g., feature values relating to the position and/or the composition of the physical point). Exemplary image capturing devices 160 capable of acquiring point-cloud data may include a 3D scanner, such as a 3D laser imaging device, a structured light scanner (e.g., a structured light laser scanner). Merely by way of example, a structured light scanner may be used to execute a scan on the target subject to acquire the point cloud data. During the scan, the structured light scanner may project structured light (e.g., a structured light spot, a structured light grid) that has a certain pattern toward the target subject. The point-cloud data may be acquired according to the structure light projected on the target subject. As yet another example, the image capturing device 160 may be used to acquire depth image data of the target subject. The depth image data may refer to image data that includes depth information of each physical point on the body surface of the target subject, such as a distance from each physical point to a specific point (e.g., an optical center of the image capturing device 160). The depth image data may be captured by a range sensing device, e.g., a structured light scanner, a time-of-flight (TOF) device, a stereo triangulation camera, a sheet of light triangulation device, an interferometry device, a coded aperture device, a stereo matching device, or the like, or any combination thereof.

In some embodiments, the image capturing device 160 may be a device independent from the medical imaging device 110 as shown in FIG. 1. For example, the image capturing device 160 may be a camera mounted on the ceiling in an examination room where the medical imaging device 110 is located. Alternatively, the image capturing device 160 may be integrated into or mounted on the medical imaging device 110 (e.g., the gantry 111). In some embodiments, the image data acquired by the image capturing device 160 may be transmitted to the processing device 120 for further analysis. Additionally or alternatively, the image data acquired by the image capturing device 160 may be transmitted to a terminal device (e.g., the terminal(s) 140) for display and/or a storage device (e.g., the storage device 130) for storage.

In some embodiments, the image capturing device 160 may be configured to capture image data of the target subject continuously or intermittently (e.g., periodically) before, during, and/or after a scan of the target subject performed by the medical imaging device 110. In some embodiments, the acquisition of the image data by the image capturing device 160, the transmission of the captured image data to the processing device 120, and the analysis of the image data may be performed substantially in real time so that the image data may provide information indicating a substantially real time status of the target subject.

In some embodiments, a coordinate system may be provided for the imaging system 100 to define a position of a component (e.g., an absolute position, a position relative to another component) and/or a movement of the component.

For illustration purposes, the coordinate system 170 may include the X-axis, the Y-axis, and the Z-axis. The X-axis and the Y-axis shown in FIG. 1 may be horizontal, and the Z-axis may be vertical. As illustrated, a positive X direction along the X-axis may be from the left side to the right side of the scanning table 114 viewed from the direction facing the front of the medical imaging device 110; a positive Y direction along the Y-axis may be the direction in which the scanning table 114 is moved from the imaging system 100 to the outside viewed from the direction facing the front of the medical imaging device 110; and a positive Z direction along the Z-axis may be from the lower part (or from the floor where the imaging system 100 stands) to the upper part of the gantry 111.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the imaging system 100 may include one or more additional components. Additionally or alternatively, one or more components of the imaging system 100, such as the image capturing device 160 or the medical imaging device 110 described above may be omitted. As another example, two or more components of the imaging system 100 may be integrated into a single component. Merely by way of example, the processing device 120 (or a portion thereof) may be integrated into the medical imaging device 110 or the image capturing device 160. In some embodiments, the imaging system 100 may further include a treatment device, such as a radiotherapy device.

FIG. 2 is a schematic diagram illustrating exemplary hardware and/or software components of a computing device 200 according to some embodiments of the present disclosure. The computing device 200 may be used to implement any component of the imaging system 100 as described herein. For example, the processing device 120 and/or the terminal 140 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 120 in accordance with techniques described herein. The computer instructions may include, for example, routines, programs, subjects, components, data structures, procedures, modules, and functions, which perform particular functions described herein. For example, the processor 210 may process image data obtained from the medical imaging device 110, the terminal(s) 140, the storage device 130, the image capturing device 160, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the medical imaging device 110, the terminal(s) 140, the storage device 130, the image capturing device 160, and/or any other component of the imaging system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program for the processing device 120 to execute to perform an automated scan preparation for a scan to be performed on a target subject. As another example, the storage device 220 may store a program for the processing device 120 to execute to perform a real-time monitoring and/or adjustment operation during the scan of the target subject.

The I/O 230 may input and/or output signals, data, information, etc. In some embodiments, the I/O 230 may enable a user interaction with the processing device 120. In some embodiments, the I/O 230 may include an input device and an output device. The input device may include alpha-numeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 150) to facilitate data communications. The communication port 240 may establish connections between the processing device 120 and the medical imaging device 110, the terminal(s) 140, the image capturing device 160, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
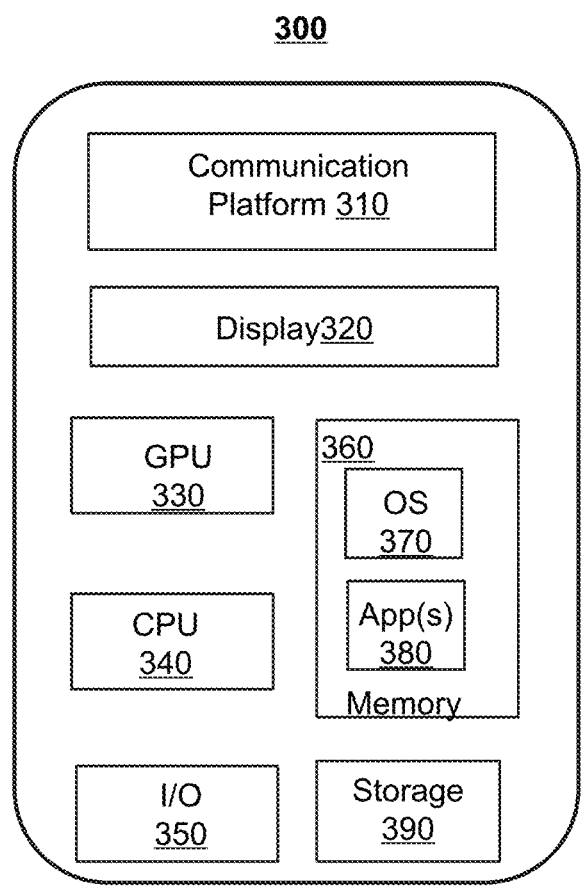
FIG. 3 is a schematic diagram illustrating exemplary hardware and/or software components of a mobile device 300 according to some embodiments of the present disclosure.

FIG. 3 is a schematic diagram illustrating exemplary hardware and/or software components of a mobile device 300 according to some embodiments of the present disclosure. In some embodiments, one or more components (e.g., a terminal 140 and/or the processing device 120) of the imaging system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the imaging system 100. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
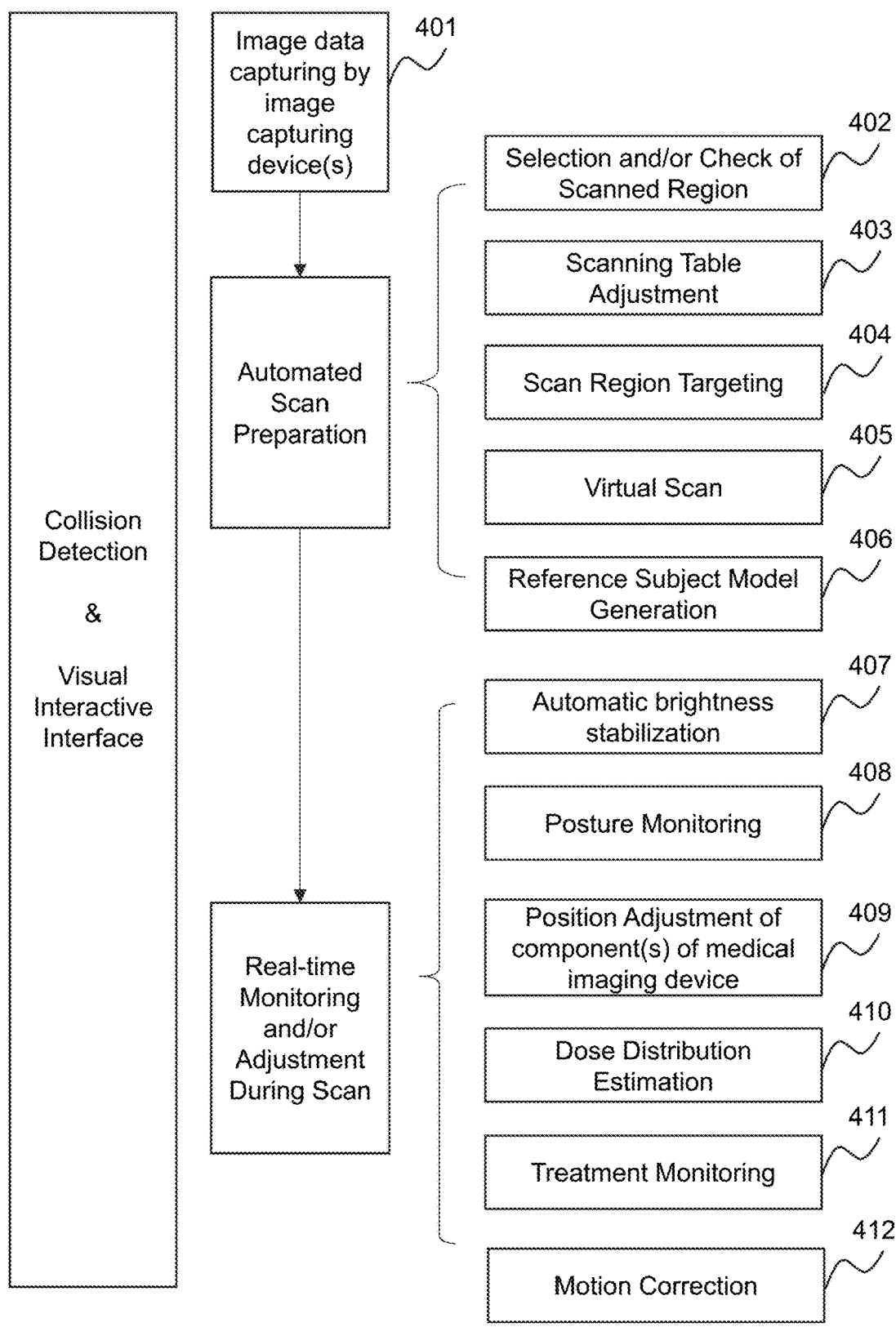
FIG. 4 is a flowchart illustrating an exemplary process for scan preparation and real-time monitoring/adjustment according to some embodiments of the present disclosure.

FIG. 4 is a flowchart illustrating an exemplary process for scan preparation and real-time monitoring/adjustment according to some embodiments of the present disclosure.

In 401, image data may be captured by one or more image capturing devices. The image data may include a 2D image, a 3D image, a 4D image (e.g., a time series of 3D images), and/or any related image data (e.g., scan data, projection data) of the target subject and/or other subject(s) in an examination room where the target subject is located. The image data may include color image data, point-cloud data, depth image data, mesh data, medical image data, or the like, or any combination thereof, of the target subject.

In some embodiments, the image data obtained in 401 may include one or more sets of image data, for example, a plurality of images of the target subject captured at a plurality of time points by an image capturing device (e.g., the image capturing device 160), a plurality of images of the target subject captured by different image capturing devices. For example, the image data may include a first set of image data capture by a specific image capturing device before the target subject is positioned at a scan position (i.e., a specific position for receiving the scan). Additionally or alternatively, the image data may include a second set of image data capture by the specific image capturing device (or another image capturing device) after the target subject is positioned at the scan position before the scan. Additionally or alternatively, the image data may include a third set of image data capture by the specific image capturing device (or another image capturing device) after the target subject is positioned at the scan position during the scan.

The processing device 120 may then perform an automated scan preparation to prepare for a scan to be performed on the target subject by the medical imaging device. The automated scan preparation may include one or more scan preparation operations, such as, one or more of operations 402 to 406 as shown in FIG. 4. Additionally or alternatively, the processing device 120 may perform a real-time monitoring and/or adjustment during the scan of the target subject. The real-time monitoring and/or adjustment may include one or more of operations 407 to 412 as shown in FIG. 4.

In some embodiments, the automated scan preparation may include a plurality of scan preparation operations. Additionally or alternatively, the real-time monitoring and/or adjustment may include a plurality of monitoring/adjustment operations. Different scan preparation operations and/or different monitoring/adjustment operations may be performed based on a same set of image data or different sets of image data of the target subject captured by one or more image capturing devices. For example, operations 402, 403, 404, 405, and 406 may be implemented based on a same set of image data or different sets of image data of the target subject captured after the target subject is positioned at the scan position. As another example, operation 406 may be implemented based on a set of image data of the target subject captured before the target subject is positioned at the scan position. For example, operations 408, 409, 410, and 412 may be implemented on a plurality of sets of image data of the target subject captured when the target subject is scanned by the medical imaging device. As another example, operations 407 and 411 may be implemented based on a set of image data of the target subject captured before the scan.

For the convenience of descriptions, the terms "image data of a target subject" used in detail descriptions regarding different preparation operations (e.g., different processes in FIGS. 6 to 38) refer to a same set of image data or different sets of image data of the target subject unless the context clearly indicates otherwise. In addition, the following descriptions describe the implementation of the automated scan preparation and the real-time monitoring/adjustment based on image data captured by a single image capturing device. It should be noted that is merely for illustration purposes, and the automated scan preparation and the real-time monitoring/adjustment may be performed based on image data captured by a plurality of image capturing devices.

In 402, a scanned region of the target subject may be selected and/or checked.

For example, the processing device 120 may determine a plurality of regions of the target subject based on the image data of the target subject and position information relating to one or more components of the medical imaging device. Different regions of the plurality of regions may correspond to different positioning procedures of the target subject. The processing device 120 may then cause a terminal device to display a target image (denoted as Ti) of the target subject with a plurality of annotations of the plurality of regions. A user (e.g., a doctor) of the imaging system 100 may select a scan region of the target subject based on the target image Ti. More descriptions for the generation of a target image Ti may be found elsewhere in the present disclosure (e.g., FIG. 7, and descriptions thereof).

As another example, the processing device 120 may obtain reference image data representing an internal structure of the target subject. The processing device 120 may then obtain one or more parameter values of one or more scan parameters of the medical imaging device relating to the scan to be performed on the target subject. The processing device 120 may further generate a target image (denoted as Ti') representing an internal structure of the scan region of the target subject under one or more parameter values based on the image data, reference image data, and the one or more parameter values. More descriptions of the generation of the target image Ti' may be found elsewhere in the present disclosure (e.g., FIG. 9, and descriptions thereof).

In 403, a target position of a scanning table of the medical imaging device may be adjusted.

For example, after the target subject lies on the scanning table, the processing device 120 may determine the target position of the scanning table based on feature information (e.g., a width, a thickness) of the target subject and feature information (e.g., a height) of an operator of the medical imaging device. The feature information of the target subject may be determined based on image data obtained in operation 401 or a subject model generated based on the image data. Merely by way of example, the height of the scanning table may be adjusted based on the thickness of the target subject and the height of the operator, which allows for convenient operation of the operator. More descriptions of the determination of the target position of the scanning table of the medical imaging device may be found elsewhere in the present disclosure (e.g., FIG. 14, and descriptions thereof).

In 404, the scan region of the target subject may be targeted.

For example, before the scan, the processing device 120 may determine target position(s) of component(s) of the medical imaging device such that the scan region of the target subject is targeted by an imaging isocenter of the medical imaging device. More descriptions of the targeting of the scan region may be found elsewhere in the present disclosure (e.g., FIG. 17 and descriptions thereof). As another example, the processing device 120 may determine a rotation scheme for the medical imaging device to adopt during the scan of the target subject such that the scan region may be targeted during the scan. More descriptions of the determination of the rotation scheme may be found elsewhere in the present disclosure (e.g., FIG. 15 and descriptions thereof).

In 405, a virtual scan may be performed.

For example, for each of one or more components of the medical imaging device, the processing device 120 may obtain a planned trajectory of the component during the scan to be performed on the target subject. The processing device 120 may then generate a virtual imaging system based on the image data obtained in operation 401. The processing device 120 may further determine whether a collision is likely to occur between the target subject and the one or more components of the medical imaging device by performing the virtual scan on the target subject based on the planned trajectories of the one or more components of the medical imaging device. More descriptions of the virtual scan may be found elsewhere in the present disclosure (e.g., FIG. 19 and descriptions thereof).

In 406, a reference subject model of the target subject may be generated.

For example, the processing device 120 may obtain reference image data representing an internal structure of the target subject. The processing device 120 may generate the reference subject model representing the internal structure of the target subject based on the reference image data and the image data obtained in operation 401. The reference subject model may indicate both the appearance and the internal structure of the target subject. More descriptions of the reference subject model may be found elsewhere in the present disclosure (e.g., FIG. 21 and descriptions thereof). In some embodiments, the reference subject model may be generated before or during the scan of the target subject. Optionally, image data of the target subject may be captured continuously or intermittently (e.g., periodically), and the reference subject model may be updated continuously or intermittently (e.g., periodically) based on the image data of the target subject.

In 407, an automatic brightness stabilization may be achieved.

For example, the processing device 120 may detect that a scanning angle of the medical imaging device changes from the first scanning angle to a second scanning angle. The processing device 120 may determine a target equivalent thickness of the target subject with respect to the second scanning angle based on the image data of the target subject. The processing device 120 may further determine one or more second parameter values of the one or more scan parameters based on the target equivalent thickness, so as to achieve the automatic brightness stabilization. More descriptions for automatic brightness stabilization may be found elsewhere in the present disclosure (e.g., FIG. 24 and descriptions thereof).

In 408, a posture of the target subject may be monitored during the scan.

For example, the processing device 120 may determine whether the target subject moves during the scan based on a plurality of sets of image data obtained in operation 401. In response to determining that the posture of the target subject changes over the series of time points, the processing device 120 may generate control information for adjusting the scan of the target subject. More descriptions for posture monitoring may be found elsewhere in the present disclosure (e.g., FIG. 25 and descriptions thereof).

In 409, the position of one or more component(s) of the medical imaging device may be adjusted automatically during the scan of the target subject.

For example, during the scan of the target subject, the processing device 120 may detect that a scan region of the target subject scanned by the medical imaging device changes from a first scan region to a second scan region. The processing device 120 may further determine feature information of the second scan region of the target subject based on the image data of the target subject obtained in operation 401. For each of one or more components of the medical imaging device, the processing device 120 may determine one or more movement parameters of the component based on the feature information of the second scan region, and cause the component to adjust its position according to the movement parameters to adapt to the change in the scan region. More descriptions for the position adjustment of the component(s) of the medical imaging device may be found elsewhere in the present disclosure (e.g., FIG. 26 and descriptions thereof).

In 410, a dose distribution during the scan may be estimated.

For example, the processing device 120 may obtain one or more parameter values of one or more radiation parameters of a radiation source of the medical imaging device. The processing device 120 may further estimate a dose distribution in an examination room based on the image data and the one or more parameter values of the radiation parameter(s). More descriptions for dose distribution estimation may be found elsewhere in the present disclosure (e.g., FIG. 28 and descriptions thereof).

In 411, a treatment performed by an invasive device (e.g., a needle, a guide wire) on the target subject may be monitored.

In some embodiments, the target subject may be treated by the invasive device, and the scan may be performed during the treatment to monitor the invasive device within the target subject. For example, the processing device 120 may monitor the invasive device by generating a composite image of the target subject indicating the position of the invasive device relative to the internal structure of the target subject based on the image data, first medical image data representing the internal structure of the target subject, and second medical image data indicative of a position of the invasive device relative to the target subject. More descriptions for the monitoring of the invasive device may be found elsewhere in the present disclosure (e.g., FIG. 30 and descriptions thereof).

In 412, a motion correction operation may be performed.

For example, the processing device 120 may detect a motion of the target subject based on a plurality of sets of image data captured by an image capturing device during the scan of the target subject. The processing device 120 may generate, based on a plurality of medical images of the target subject, a target image of the target subject, wherein motion correction may be performed based on the detected motion of the target subject during the generation of the target image. More descriptions for motion correction may be found elsewhere in the present disclosure (e.g., FIG. 31 and descriptions thereof).

In some embodiments, as shown in FIG. 4, a collision detection may be performed during the implementation of the process 400 (or a portion thereof). For example, an image capturing device may be configured to capture image data of a plurality of subjects in an examination room, and the processing device 120 may detect possible collision between different subjects based on the image data. More descriptions for collision detection may be found elsewhere in the present disclosure (e.g., FIG. 36 and descriptions thereof).

Additionally or alternatively, a visual interactive interface may be used to achieve a user interaction between the user and the imaging system and/or between the target subject and the imaging system. The visual interactive interface may be implemented on, for example, a terminal device 140 as described in connection with FIG. 1 or a mobile device 300 as described in connection with FIG. 3. The visual interactive interface may present data obtained and/or generated by the processing device 120 (e.g., an analysis result, an intermediate result) in the implementation of the process 400. For example, a target image Ti of the target subject with a plurality of annotations of a plurality of regions of the target subject as described in connection with FIG. 7 may be displayed by the visual interactive interface. As another example, a virtual scan performed using a virtual imaging system as described in connection with FIG. 19 may be displayed by the visual interactive interface. As still another example, a target image Ti' representing an internal structure of a scan region of the target subject as described in connection with FIG. 9 may be displayed by the visual interactive interface. Additionally or alternatively, the visual interactive interface may receive a user input from the user and/or the target subject.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 400 may be added or omitted. For example, one or more of the operations 402-406 may be omitted. In some embodiments, two or more operations may be performed simultaneously. For example, operation 405 and operation 406 may be performed simultaneously. As yet another example, operation 408 may be performed before operation 407. In some embodiments, an operation performed before the scan may be performed during the scan, and/or an operation performed during the scan may be performed before the scan.

Figure 5:
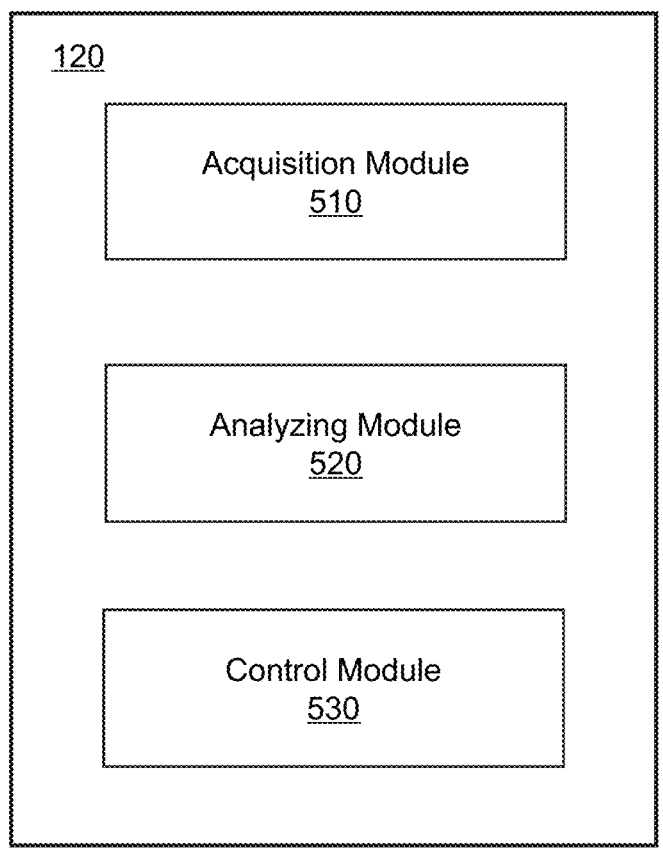
FIG. 5 is a block diagram illustrating an exemplary processing device 120 according to some embodiments of the present disclosure.

FIG. 5 is a block diagram illustrating an exemplary processing device 120 according to some embodiments of the present disclosure. As shown in FIG. 5, the processing device 120 may include an acquisition module 510, an analyzing module 520, and a control module 530.

The acquisition module 510 may be configured to obtain information relating to the imaging system 100. For example, the acquisition module 510 may obtain image data of a target subject before, during, and/or after the target subject is examined (e.g., scanned) by a medical imaging device, wherein the image data may be captured by an image capturing device (e.g., a camera mounted in an examination room where the target subject is located). As another example, the acquisition module 510 may obtain a planned trajectory and/or position information of a component (e.g., a detector, a radiation source) of the medical imaging device. As yet another example, the acquisition module 510 may obtain a reference subject model of the target subject.

The analyzing module 520 may be configured to perform one or more scan preparation operations to prepare for a scan of the target subject by analyzing the information obtained by the acquisition module 510. Additionally or alternatively, the analyzing 520 may be configured to perform one or more monitoring/adjustment operations to monitor and/or adjust the scan of the target subject by analyzing the information obtained by the acquisition module 510. More descriptions regarding the analysis of the information, the scan preparation operation(s), and the monitoring/adjustment operation(s) may be found elsewhere in the present disclosure. See, e.g., FIG. 4 and FIGS. 8-38 and relevant descriptions thereof.

The control module 530 may be configured to control one or more components of the imaging system 100. For example, the control module 530 may cause one or more components of the medical imaging device to move to their respective target position(s). As another example, the control module 530 may be configured to cause a terminal device to display an image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further include a storage module (not shown in FIG. 5). The storage module may be configured to store data generated during any process performed by any component of in the processing device 120. As another example, each of components of the processing device 120 may include a storage device. Additionally or alternatively, the components of the processing device 120 may share a common storage device. As yet another example, a module of the processing device 120 may be divided into a plurality of units.

Figure 6:
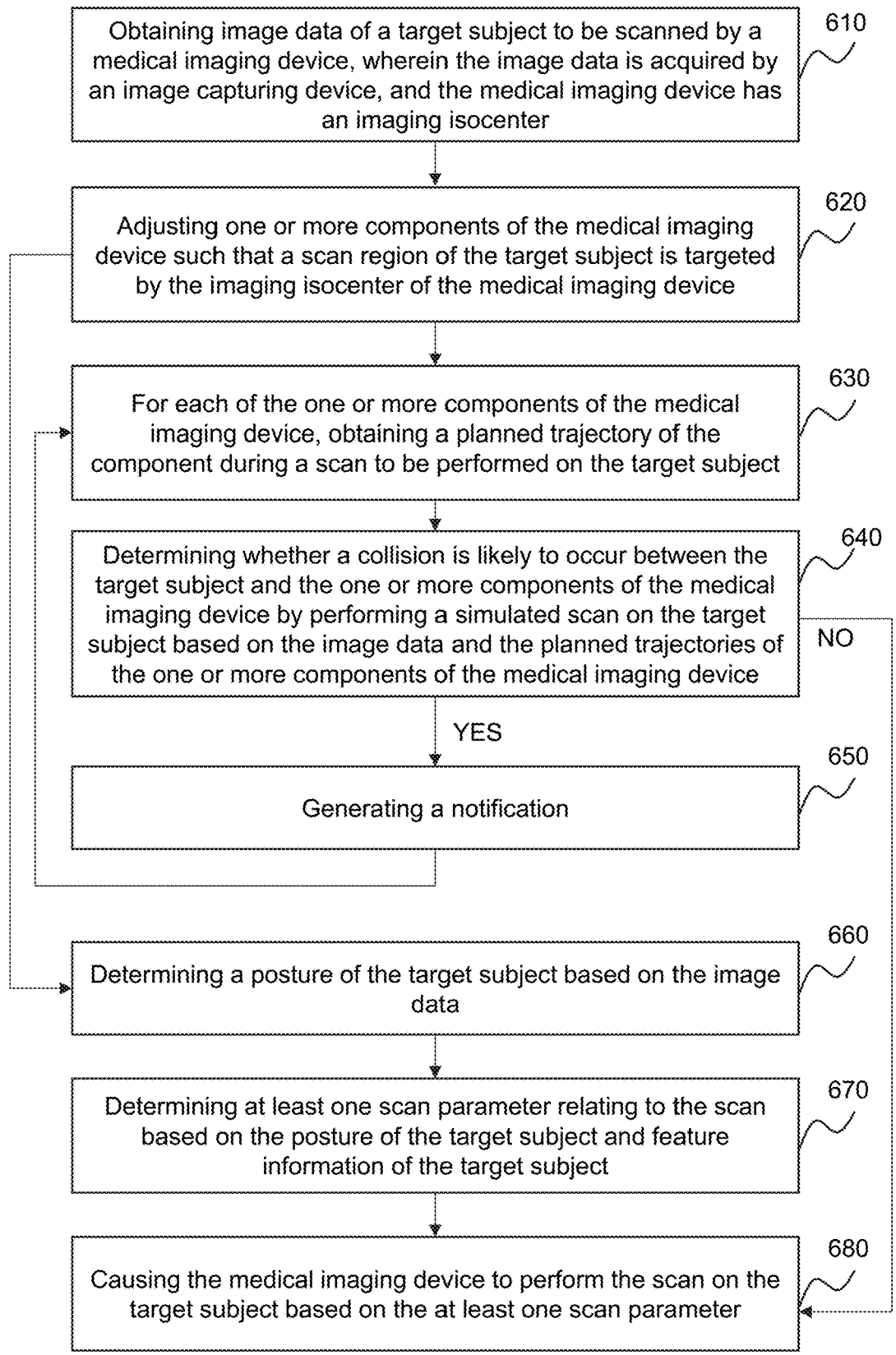
FIG. 6 is a flowchart illustrating an exemplary process for scan preparation according to some embodiments of the present disclosure.

FIG. 6 is a flowchart illustrating an exemplary process for scan preparation according to some embodiments of the present disclosure.

In 610, the processing device 120 (e.g., the acquisition module 510) may obtain image data of a target subject to be scanned by a medical imaging device. The image data may be acquired by an image capturing device. The medical imaging device may have an imaging isocenter.

In some embodiments, the target subject may be a biological subject (e.g., a patient) and/or a non-biological subject to be scanned (e.g., imaged or treated) by the medical imaging device (e.g., the medical imaging device 110). The image data of the target subject refers to image data corresponding to the entire target subject or image data corresponding to a portion of the target subject. In some embodiments, the image data of the target subject may include a two-dimensional (2D) image, a three-dimensional (3D) image, a four-dimensional (4D) image (e.g., a series of images over time), and/or any related image data (e.g., scan data, projection data). In some embodiments, the image data of the target subject may include color image data, point-cloud data, depth image data, mesh data, or the like, or any combination thereof, of the candidate subject(s).

In some embodiments, the image data of the target subject may be captured by the image capturing device, such as the image capturing device 160. The image capturing device may include any type of device that is capable of acquiring image data, such as a 3D camera, an RGB sensor, an RGB-D sensor, a 3D scanner, a 3D laser imaging device, a structured light scanner. In some embodiments, the processing device 120 may obtain the image data from the image capturing device. Alternatively, the image data may be acquired by the image capturing device and stored in a storage device (e.g., the storage device 130, the storage device 220, the storage 390, or an external source). The processing device 120 may retrieve the image data from the storage device.

In some embodiments, the image data may be captured by the image capturing device after the target subject is positioned at a scan position for receiving a scan. For example, after the target subject is placed on a scanning table of the medical imaging device, the imaging capturing device may be directed to capture the image data of the target subject.

The medical imaging device may be used to perform a scan on the target subject. In some embodiments, the medical imaging device (e.g., the medical imaging device 110) may be an X-ray imaging device (e.g., a suspended X-ray imaging device, a C-arm X-ray imaging device), a digital radiography (DR) device (e.g., a mobile digital X-ray imaging device), a CT device (e.g., a CBCT device, an MSCT device), a PET device, an MRI device, or the like, as described elsewhere in the present disclosure.

In some embodiments, the medical imaging device may have an imaging isocenter. As used herein, an imaging isocenter of a medical imaging device refers to a mechanical isocenter of the medical imaging device. For example, for an X-ray imaging device having a gantry (e.g., a cylindrical gantry, a C-shape gantry), the imaging isocenter of the X-ray imaging device may be the center of the gantry. In some embodiments, one or more components (e.g., the radiation source 115, the gantry 111) of the medical imaging device may rotate around the imaging isocenter when the medical imaging device performs an isocentric rotation. The one or more components of the medical imaging device may rotate around a point other than the imaging isocenter when the medical imaging device performs a non-isocentric rotation.

In some embodiments, a position of the imaging isocenter may be determined based on a position of a component (e.g., the C-shape gantry) of the medical imaging device in a coordinate system (e.g., a coordinate of the component of the medical imaging device in the coordinate system 170) and a position of the imaging isocenter relative to the component of the medical imaging device. In some embodiments, the position of the imaging isocenter may be previously determined, for example, when the medical imaging device is mounted, and stored in a storage device (e.g., the storage device 130) of the imaging system 100. In some embodiments, the position of the imaging isocenter may be represented by a coordinate in a coordinate system (e.g., in the coordinate system 170 as shown in FIG. 1).

In 620, the processing device 120 (e.g., the control module 530) may adjust one or more components of the medical imaging device such that a scan region of the target subject is targeted by the imaging isocenter of the medical imaging device.

In some embodiments, the processing device 120 may determine the scan region of the target subject based on the image data of the target subject by performing operation 1720 as described in connection with FIG. 17. The processing device 120 may further adjust the one or more components of the medical imaging device such that the scan region is targeted by the imaging isocenter of the medical imaging device by performing operation 1730 as described in connection with FIG. 17, and the descriptions thereof are not repeated here.

In 630, for each of one or more components of the medical imaging device, the processing device 120 (e.g., the acquisition module 510) may obtain a planned trajectory of the component during a scan to be performed on the target subject.

More descriptions regarding the acquisition of the planned trajectory (trajectories) of the component(s) of the medical imaging device may be found elsewhere in the present disclosure. See, e.g., operation 1920 in FIG. 19 and relevant descriptions thereof.

In 640, the processing device 120 (e.g., the analyzing module 520) may determine whether a collision is likely to occur between the target subject and the one or more components of the medical imaging device by performing a virtual scan on the target subject based on the image data and the planned trajectories of the one or more components of the medical imaging device.

In some embodiments, operation 640 may be performed by performing operations 1930-1950 as described in connection with FIG. 19, and the descriptions thereof are not repeated here.

In response to determining that a collision is not likely to occur between the target subject and the one or more components of the medical imaging device, the process 600 may proceed to operation 680, or alternatively, operation 660 (not shown in FIG. 6). In response to determining that a collision is likely to occur between the target subject and the component(s) during the scan, the process 600 may proceed to operation 650.

In 650, the processing device 120 (e.g., the analyzing module 520) may generate a notification.

The notification may indicate that a collision is likely to occur between the target subject and the one or more components of the medical imaging device. The notification may be in the form of text, voice, an image, a video, a haptic alert, or the like, or any combination thereof. For example, the processing device 120 may transmit the notification to a terminal device (e.g., the terminal device 140) of a user (e.g., a doctor) of the imaging system 100. The terminal device may output the notification to the user. Optionally, the user may input an instruction or information in response to the notification. Merely by way of example, the user may input an instruction for adjusting the position(s) of the target subject and/or the component(s) of the medical imaging device based on the likely occurred collision. As another example, the user may manually move a component that may collide with the target subject.

In some embodiments, after the position(s) of the target subject and/or the component(s) of the medical imaging device are adjusted, the processing device 120 may then obtain updated planned trajectory (trajectories) of the component(s) based on updated position information of the component(s) of the medical imaging device. The processing device 120 may further determine whether a collision is likely to occur between the target subject and the one or more components of the medical imaging device based on updated position information of the target subject and/or the updated planned trajectory (trajectories) of the component(s) of the medical imaging device. In some embodiments, the iteration of 630 to 650 may be repeated until a collision is not likely to occur between the target subject and the one or more components of the medical imaging device.

Alternatively, after the position(s) of the target subject and/or the component(s) of the medical imaging device are adjusted, the processing device 120 may obtain image data of the target subject, and determine updated position information of the target subject based on the image data. The processing device 120 may then obtain an updated planned trajectory (trajectories) of the component(s) based on updated position information of the component(s) of the medical imaging device. The processing device 120 may further determine whether a collision is likely to occur between the target subject and the one or more components of the medical imaging device based on the updated position information of the target subject and/or the updated planned trajectory (trajectories) of the component(s) of the medical imaging device. In some embodiments, the iteration of 610 to 650 may be repeated until a collision is not likely to occur between the target subject and the one or more components of the medical imaging device.

In some embodiments, after the one or more components of the medical imaging device are at their respective positions in operation 620, the process 600 may proceed to operation 660.

Alternatively, if it is determined that a collision is not likely to occur in operation 640, the process 600 may proceed to operation 660. In 660, the processing device 120 (e.g., the analyzing module 520) may determine a posture of the target subject based on the image data.

Exemplary postures may include a head first-supine (HFS) posture, a head first-prone (HFP) posture, a head first-decubitus right (HFDR) posture, a head first-decubitus left (HFDL) posture, a feet first-decubitus right (FFDR) posture, a feet first-decubitus left (FFDL) posture, a feet first-prone (FFP) posture, a feet first-supine (FFS) posture, etc. In some embodiments, the processing device 120 may determine the posture of the target subject based on the image data according to an image analysis algorithm (e.g., an image segmentation algorithm, a feature point extraction algorithm). Additionally or alternatively, the processing device 120 may determine the posture of the target subject by generating a subject model representing the target subject based on the image data. As used herein, a subject model of a target subject determined based on image data of the target subject refers to a model representing an appearance of the target subject. for example, the subject model may indicate the contour and/or the posture of the target subject when the image data is captured. A posture of a target subject may reflect one or more of a position, a pose, a shape, a size, etc., of the target subject (or a portion thereof).

In some embodiments, the subject model may include a 2D skeleton model, a 3D skeleton model, a 3D mesh model, or the like. A 2D skeleton model of a target subject may include an image illustrating one or more anatomical joints and/or bones of the target subject in 2D space. A 3D skeleton model of a target subject may include an image illustrating one or more anatomical joints and/or bones of the target subject in 3D space. A 3D mesh model of a target subject may include a plurality of vertices, edges, and faces that define a 3D shape of the target subject.

In some embodiment, the processing device 120 may generate the subject model (e.g., the 3D mesh model) of the target subject based on the image data according to one or more mesh generation techniques, such as a Triangular/Tetrahedral (Tri/Tet) technique (e.g., an Octree algorithm, an Advancing Front algorithm, a Delaunay algorithm, etc.), a Quadrilateral/Hexahedra (Quad/Hex) technique (e.g., a Trans-finite Interpolation (TFI) algorithm, an Elliptic algorithm, etc.), a hybrid technique, a parametric model based technique, a surface meshing technique, or the like, or any combination thereof.

In 670, the processing device 120 (e.g., the analyzing module 520) may determine at least one scan parameter relating to the scan based on the posture of the target subject and feature information of the target subject.

The feature information of the target subject may include a width, a height, a thickness, an attenuation coefficient (e.g., a CT attenuation value), or the like, of the target subject or a portion of the target subject. The attenuation coefficient of a portion of the target subject may be, for example, an average attenuation coefficient of the portion (e.g., the head, the body, an arm, a leg) of the target subject. Different portions of the target subject may have different attenuation coefficient. In some embodiments, the feature information of the target subject may be previously determined and stored in a storage device (e.g., the storage device 130, the storage device 220, the storage 390, or an external source). The processing device 120 may retrieve the feature information of the target subject from the storage device. Additionally or alternatively, the feature information of the target subject may be determined based on image data of the target subject. More descriptions for determining the feature information of the target subject based on the image data of the target subject may be found elsewhere in the present disclosure (e.g., FIG. 7 and descriptions thereof).

The processing device 120 may determine value(s) of the scan parameter(s) relating to the scan based on the posture of the target subject and the feature information of the target subject. Exemplary scan parameters may include a voltage of a radiation source, a current of the radiation source, a distance between the radiation source and a detector, a radiation dose, a size of a focal spot, a filtration of radiation rays, or the like, or any combination thereof. For example, the processing device 120 may determine initial value(s) of the scan parameter(s) relating to the scan of the target subject according to, for example, an imaging protocol of the target subject. The processing device 120 may determine the values of the scan parameter(s) by adjusting the initial values of the scan parameter(s) based on the posture of the target subject and/or the feature information of the target subject. For illustration purposes, the processing device 120 may determine whether the hands of the target subject are placed on two sides of the target subject's body. In response to determining that the hands of the target subject are not located on the two sides of the target subject's body, the processing device 120 may designate the initial value(s) of the scan parameter(s) as the values of the scan parameter(s). In response to determining that the hands of the target subject are located on the two sides of the target subject's body, the processing device 120 may adjust (e.g., increase) the initial value(s) of the initial scan parameter(s) to determine the values of the scan parameter(s).

In 680, the processing device 120 (e.g., the control module 530) may cause the medical imaging device to perform the scan on the target subject based on the at least one scan parameter.

In some embodiments, before the scan is performed on the target subject, the processing device 120 may perform one or more additional operations to prepare for the scan on the target subject. For example, the processing device 120 may generate a target image Ti with a plurality of annotations of a plurality of regions of the target subject, and cause a terminal device (e.g., the terminal device 140) to display the target image. More descriptions regarding the target image Ti with the plurality of annotations of the plurality of regions of the target subject may be found elsewhere in the present disclosure. See, e.g., FIGS. 7, 8, and relevant descriptions thereof. As another example, the processing device 120 may generate a target image Ti' representing an internal structure of a scan region of the target subject, and cause a terminal device (e.g., the terminal device 140) to display the target image Ti'. More descriptions regarding the target image Ti' representing the internal structure of the scan region of the target subject may be found elsewhere in the present disclosure. See, e.g., FIGS. 9-13, and relevant descriptions thereof. As still another example, the processing device 120 may determine a target position of a scanning table based on the image data of the target subject and feature information of an operator. More descriptions regarding the determination of the target position of the scanning table may be found elsewhere in the present disclosure. See, e.g., FIG. 14, and relevant descriptions thereof. As still another example, the processing device 120 may determine a rotation scheme of the medical imaging device based on the position of the imaging isocenter and a position of a POI of the target subject. More descriptions regarding the rotation scheme determination may be found elsewhere in the present disclosure. See, e.g., FIGS. 15-16, and relevant descriptions thereof. As still another example, the processing device 120 may generate a reference subject model based on the image data of the target subject and reference image data of the target subject. More descriptions regarding the reference subject model generation may be found elsewhere in the present disclosure. See, e.g., FIGS. 21-23 and relevant descriptions thereof.

According to some embodiments of the present disclosure, position(s) of component(s) of the medical imaging device may be adjusted based on a position of the scan region of the target subject. In addition, the virtual scan may be performed on the target subject using the virtual imaging system to determine whether a collision is likely to occur between the target subject and the component(s) of the medical imaging device during the scan. Conventionally, a radiation source of the medical imaging device may need to move to a plurality of positions, and position(s) of the component(s) of the medical imaging device may be adjusted to target the imaging isocenter of the medical imaging device at the scan region. The component(s) of the medical imaging device may need to actually move along their planned trajectory (trajectories) to simulate the scan of the target subject. Compared to the conventional way which involves a lot of human intervention, the systems and methods disclosed herein may be fully or partially automated, more accurate and efficient by, e.g., reducing unnecessary radiation to a target subject and a user, the workload of a user, cross-user variations, and the time needed for the scan preparation.

In some embodiments, one or more operations may be added or omitted. For example, operations 660 and 670 may be omitted. In some embodiments, two or more operations may be performed simultaneously. For example, operation 640 and operation 660 may be performed simultaneously.

FIG. 7 is a flowchart illustrating an exemplary process for positioning a target subject to be scanned by a medical imaging device according to some embodiments of the present disclosure. In some embodiments, process 700 may be performed before a scan to be performed on a target subject by a medical imaging device. For example, one or more operations of the process 700 may be performed before process 900, process 1400, process 1500, process 1700, and/or process 1900.

In 710, the processing device 120 (e.g., the acquisition module 510) may obtain image data indicative of a position of the target subject relative to one or more components of the medical imaging device. The image data may be captured by an image capturing device.

In some embodiments, operation 710 may be performed in a similar manner as operation 610 as described in connection with FIG. 6.

The medical imaging device may be any device that can scan the target subject. Merely by way of example, the medical imaging device may be an X-ray imaging device, and the one or more components of the X-ray imaging device may include a scanning table (e.g., the scanning table 114), a detector (e.g., the detector 112), a radiation source (e.g., the radiation source 115), a supporting device (e.g., a C-arm) supporting the detector and the radiation source, or the like.

In some embodiments, the image data may indicate a position of the target subject relative to the one or more components of the medical imaging device. Specifically, the processing device 120 may identify a representation of the target subject and one or more representations of the one or more components in the image data. For each component of the medical imaging device, the processing device 120 may determine the position of the target subject relative to the component based on the representation of the target subject and the representation of the component in the image data. For illustration purposes, it is assumed that the target subject lies on the scanning table and the entire body of the target subject occupies a specific area of the scanning table. The image data may show the specific area of the scanning table that is occupied by the target subject. This is not intended to be limiting. For example, the medical imaging device may be a suspended X-ray imaging device, and the target subject may stand on the ground to receive the scan.

In 720, the processing device 120 (e.g., the acquisition module 510) may obtain position information relating to the one or more components of the medical imaging device.

The position information relating to a specific component of the medical imaging device may include, for example, a coordinate of the specific component in a coordinate system (e.g., the coordinate system 170 as shown in FIG. 1). In some embodiments, the processing device 120 may obtain the position information of a component based on the image data acquired in 710. For example, the processing device 120 may identify the representation of the component in the image data, and determine the position information relating to the component based on the position of the representation of the component in the image data. Additionally or alternatively, the processing device 120 may obtain the position information of a component from a position encoder of the imaging system 100. For example, a position encoder mounted on the scanning table may be configured to measure a position of the scanning table.

In some embodiments, the position information relating to a component may be determined by one or more components of the imaging system 100, or manually set by a user of the imaging system 100 according to different situations. For example, the user may input position parameter(s) of a component. As another example, the position information of the component may be determined according to an imaging protocol. The imaging protocol may include, for example, value(s) or value range(s) of one or more scan parameters (e.g., an X-ray tube voltage and/or current, an X-ray tube angle, a scan mode, a table moving speed, a gantry rotation speed, a field of view (FOV)), a source image distance (SID), a portion of the target subject to be imaged, feature information of the target subject (e.g., the gender, the body shape), or the like, or any combination thereof. The imaging protocol (or a portion thereof) may be determined manually by a user (e.g., a doctor) or by one or more components (e.g., the processing device 120) of the imaging system 100 according to different situations.

As another example, the user may manually move a component of the medical imaging device to a suitable position. As still another example, a plurality of sets of preset positions of the one or more components may be stored in the imaging system 100. The user may select a set of preset positions of the target subject. Merely by way of example, the plurality of sets of preset positions may include that a rotation angle of the scanning table is 0 degree and a gantry angle is 0 degree (i.e., a radiation source faces the head of the target subject), the rotation angle of the scanning table is 0 degree and the gantry angle is 90 degrees (i.e., a radiation source faces a right side of the target subject), the rotation angle of the scanning table is 0 degree and the gantry angle is 270 degrees (i.e., a radiation source faces a left side of the target subject), the rotation angle of the scanning table is 15 degrees and the gantry angle is 90 degrees, the rotation angle of the scanning table is 15 degrees and the gantry angle is 270 degrees, the rotation angle of the scanning table is 30 degrees and the gantry angle is 90 degrees, the rotation angle of the scanning table is 30 degrees and the gantry angle is 270 degrees, or the like.

In some embodiments, the rotation angle of the scanning table may include a roll rotation angle, a pitch rotation angle, a yaw rotation angle, or the like, or any combination thereof. As used herein, a roll rotation angle refers to a rotation angle of the scanning table about the Y-axis of the coordinate system 170 as shown in FIG. 1; the pitch rotation angle refers to a rotation angle of the scanning table about the X-axis of the coordinate system 170; and the yaw rotation angle refers to a rotation angle of the scanning table about the Z-axis of the coordinate system 170. The gantry angle of the medical imaging device may relate to a position of the radiation source (e.g., the radiation source 115) of the medical imaging device. For example, the gantry angle may be an angle between a vertical direction (i.e., the Z-axis direction of the coordinate system 170 as shown in FIG. 1) and the radiation direction of a radiation beam emitted from the radiation source.

In some embodiments, the position information of a specific component of the medical imaging device may include constrain information relating to the position of the specific component. Merely by way of example, the scanning table of the medical imaging device may only move in a specific moving range, otherwise, it may collide with other component(s), such as the supporting component (e.g., a C-arm), of the medical imaging device. The moving range of the scanning table may be associated with the structure of the scanning table and/or the structure of other component(s) of the medical imaging device, such as a base of the supporting device. In some embodiments, the constrain information of the specific component may be stored in a storage device (e.g., the storage device 130) of the imaging system 100, and the processing device 120 may retrieve the constrain information from the storage device.

In 730, the processing device 120 (e.g., the analyzing module 520) may determine a plurality of regions of the target subject based on the image data and the position information. Different regions of the plurality of regions may correspond to different positioning procedures of the target subject.

As used herein, a positioning procedure corresponding to a region of the target subject refers to a process of positioning the target subject such that the region of the target subject can be imaged by the medical imaging device. For example, the positioning procedure corresponding to a region of the target subject may involve moving the target subject and/or the component(s) of the medical imaging device (or a portion thereof) such that the region is targeted by the medical imaging device. In some embodiments, a region may be regarded as being targeted by the medical imaging device if the region is coincident with an imaging isocenter of the medical imaging device.

In some embodiments, the plurality of regions may include a first region that can be imaged by the medical imaging device without moving the scanning table, a second region that can be imaged by the medical imaging device by moving (e.g., translating, rotating) the scanning table, a third region that cannot be imaged by the medical imaging device, or the like, or any combination thereof. For example, the first region of the target subject may be located within a detection region (e.g., the detection region 113) of the medical imaging device. A size and a position of the detection region may be determined based on a position of the radiation source (e.g., the radiation source 115) and a position of the detector (e.g., the detector 112). The X-ray beams emitted by the radiation source (e.g., the radiation source 115) of the medical imaging device may traverse the first region of the target subject and be detected by the detector (e.g., the detector 112) of the medical imaging device when the target subject is located at its original position. The second region may include a portion of the target subject that is located outside but can be moved into the detection region of the medical imaging device. The third region may include a portion of the target subject that is always out of the detection region of the medical imaging device even if the target subject is moved via the scanning table. As described in connection with operation 720, the movement of the scanning table may be constrained in a specific moving range in order to avoid a collision between the scanning table and other component(s) of the medical imaging device. Because of the limited movement of the scanning table, a portion of the target subject cannot be scanned by the medical imaging device even if the scanning table is moved.

In some embodiments, the division of the first, second, and third regions of the target subject may be associated with, for example, feature information of the target subject, the position of the scanning table and/or one or more other components of the medical imaging device, or the like. The feature information of the target subject may include a height, a width, a thickness, a position, or the like, of the target subject or a portion of the target subject. As used herein, a width of the target subject refers to a length of the target subject (e.g., a length at the center of the target subject, a maximum length of the target subject) along a direction perpendicular to a sagittal plane of the target subject. A height of a target subject refers to a length of the target subject (e.g., a length at the center of the target subject, a maximum length of the target subject) along a direction perpendicular to a transverse plane of the target subject. A thickness of a target subject refers to a length of the target subject (e.g., a length at the center of the target subject, a maximum length of the target subject) along a direction perpendicular to a coronal plane of the target subject. In some embodiments, the target subject may be scanned by radiation rays emitted by a radiation source, and the thickness of the target subject may be an estimated distance that the radiation rays may transverse within the target subject during the scan.

For example, the position of the target subject on the scanning table may affect the division of the first, second, and third regions. The area of the third region may be increased if the target subject lies closer to the end of the scanning table that is out of the detection region. As another example, if a body size of the target subject is relatively large (e.g., the height of the target subject is relatively high), the area of the third region of the target subject may be relatively large.

In some embodiments, the processing device 120 may determine the plurality of regions based on the image data and the position information. For example, the processing device 120 may determine the feature information (or a portion thereof) of the target subject based on the image data according to an image analysis algorithm (e.g., an image segmentation algorithm, a feature point extraction algorithm). Additionally or alternatively, the feature information (or a portion thereof) of the target subject may be previously generated and stored in a storage device (e.g., the storage device 130, the storage device 220, the storage 390, or an external source). The processing device 120 may retrieve the feature information (or a portion thereof) of the target subject from the storage device.

The processing device 120 may then determine the position of the target subject relative to the scanning table based on the image data as described in connection with operation 710. The processing device 120 may further determine the plurality of regions of the target subject based on the feature information of the target subject, the position of the target subject relative to the scanning table, and the position information of the scanning table and the supporting device. For example, the processing device 120 may determine the plurality of regions of the target subject by performing one or more simulation experiments. As another example, the processing device 120 may divide the scanning table into one or more portions, such as a first portion that is within the detection region of the medical imaging device, a second portion that can be moved into the detection region of the medical imaging device, and a third region that cannot be moved into the detection region of the medical imaging device. The processing device 120 may further determine the first, second, and third regions of the target subject based on the feature information of the target subject, the position of the target subject with respect to the scanning table, and the first, second, and third portions of the scanning table. Merely by way of example, a region of the target subject within the first portion may be designated as the first region, a region of the target subject within the second portion may be designated as the second region, and a region of the target subject within the third portion may be designated as the third region.

It should be noted that the above description of the determination of the plurality of regions of the target subject is merely provided for the purposes of illustration, and not intended to limit the scope of the present disclosure. The plurality of regions may be determined according to different rules. For example, the plurality of regions may include a region that can be imaged by the medical imaging device without moving the scanning table, a region that can be imaged by the medical imaging device by translating the scanning table, a region that can be imaged by the medical imaging device by rotating the scanning table, a region that cannot be imaged by the medical imaging device, or the like, or any combination thereof. As another example, for a suspended imaging device (e.g., a suspended X-ray imaging device), the plurality of regions of the target subject may be defined according to the movement of a radiation source or a detector. Merely by way of example, the plurality of regions may include a region that can be imaged by the medical imaging device without moving the radiation source, a region that can be imaged by the medical imaging device by moving the radiation source, a region that cannot be imaged by the medical imaging device, or the like, or any combination thereof.

In 740, the processing device 120 (e.g., the control module 530) may cause a terminal device to display a target image Ti of the target subject with a plurality of annotations of the plurality of regions.

In some embodiments, the plurality of annotations of the plurality of regions may be displayed in the target image Ti in different forms, such as different colors or different textures. For example, a first annotation of the first region may be displayed in the target image Ti in green color, a second annotation of the second region may be displayed in the target image Ti in yellow color, and a third annotation of the third region may be displayed in the target image Ti in red color.

In some embodiments, the processing device 120 may generate the target image Ti by adding the plurality of annotations of the plurality of regions on the image data. Additionally or alternatively, the processing device 120 may generate the target image Ti by adding the plurality of annotations of the plurality of regions on a subject model generated based on the image data. Specifically, the processing device 120 may generate the subject model representing the target subject based on the image data. The processing device 120 may further generate the target image Ti by adding the plurality of annotations of the plurality of regions on the subject model. More descriptions for generating the subject model may be found elsewhere in the present disclosure (e.g., FIG. 6 and descriptions thereof).

In some embodiments, the processing device 120 may generate the target image Ti by adding the plurality of annotations of the plurality of regions on a reference subject model generated based on the image data and reference image data. The reference subject model refers to a model representing an internal structure of the target subject who holds a posture when the image data is captured. Specifically, the processing device 120 may obtain reference image data representing an internal structure of the target subject. The processing device 120 may then generate the reference subject model representing the internal structure of the target subject by combining the reference image data and the subject model. The processing device 120 may further generate the target image Ti by adding the plurality of annotations of the plurality of regions on the reference subject model. More descriptions of the reference subject model may be found elsewhere in the present disclosure (e.g., FIG. 21 and descriptions thereof).

After the annotations of the regions of the target subject are added, the processing device 120 may cause the terminal device to display the target image Ti with the annotations. Optionally, the processing device 120 may further obtain an input associated with a scan region of the target subject. As used herein, a scan region of the target subject refers to a desired portion (e.g., a specific organ or tissue) of the target subject to be imaged (or examined or treated) by the medical imaging device. For example, the terminal device may display the target image Ti, and a user may select the scan region (e.g., by drawing an area corresponding to the scan region, by selecting a plurality of reference points corresponding to the scan region) on the displayed target image Ti via an input component of the terminal device (e.g., a mouse, a touch screen).

For example, the processing device 120 may obtain, via the terminal device, a first input associated with a first scan region of the target subject. The first scan region may be within the first region. The processing device 120 may further cause the medical imaging device to scan the first scan region based on the first input. Optionally, the processing device 120 may determine a target position of the supporting device based on the first scan region, the image data, and the position information. When the supporting device is located at the target position, a center point (e.g., a POI) of the first scan region may be coincident with an imaging isocenter of the medical imaging device. More descriptions for adjusting position(s) of component(s) of the medical imaging device based on a scan region of the target subject and an imaging isocenter of the medical imaging device may be found elsewhere in the present disclosure (e.g., FIGS. 15-18, and descriptions thereof).

As another example, the processing device 120 may obtain, via the terminal device, a second input associated with a second scan region of the target subject. At least part of the second scan region may be within the second region. The processing device 120 may determine a target position of the target subject based on the second input, the image data, and the position information. When the target subject is located at its target position, the second scan region of the target subject can be imaged by the medical imaging device. The processing device 120 may cause the scanning table to move the target subject to its target position. The processing device 120 may further cause the medical imaging device to scan the target subject when the target subject is at its target position. Alternatively, the processing device 120 may determine a target position of the supporting device and a target position of the target subject based on the second input, the image data, and the position information. When the supporting device and the target subject are located at their respective target positions, the second scan region of the target subject can be imaged by the medical imaging device. The processing device 120 may cause the supporting device to move to the target position of the supporting device, and the scanning table to move the target subject to the target position of the target subject. The processing device 120 may cause the medical imaging device to scan the target subject when the supporting device and the target subject are located at their respective target positions.

As still another example, the processing device 120 may obtain, via the terminal device, a third input associated with a third scan region of the target subject. At least part of the third scan region may be within the third region. The processing device 120 may generate a notification. The notification may indicate that the third scan region cannot be imaged by the medical imaging device. The notification may be in the form of text, voice, an image, a video, a haptic alert, or the like, or any combination thereof. For example, the processing device 120 may transmit the notification to the terminal device (e.g., the terminal device 140) of a user (e.g., a doctor) of the imaging system 100. The terminal device may output the notification to the user. Optionally, the user may adjust the position of the target subject and/or the medical imaging device in response to the notification. Merely by way of example, the user may guide the target subject to change his/her position relative to the scanning table.

In some embodiments, the processing device 120 may cause the terminal device to display the image data of the target subject obtained in operation 710 or a model (e.g., a subject model or a reference subject model) representing the target subject generated based on the image data. The processing device 120 may obtain, via the terminal device, an input associated with a scan region of the target subject. The processing device 120 may determine a specific region of the target subject that the scan region belongs to, and determine a positioning procedure corresponding to the specific region of the target subject as the positioning procedure of the target subject. Optionally, the processing device 120 may display an annotation of the scan region in a specific form (e.g., a specific color) based on the specific region of the target subject that the scan region belongs to. For illustration purposes, a user may draw a box on the displayed image data or model to select the scan region. If the scan region is within the first region of the target subject, the box may be displayed in green. If at least part of the scan region is within the second region of the target subject, the box may be displayed in yellow. If at least part of the scan region is within the third region of the target subject, the box may be displayed in red.

According to some embodiments of the present disclosure, a plurality of regions of the target subject corresponding to different positioning procedures may be determined based on the image data of the target subject and the position information relating to the one or more components of the medical imaging device. A target image Ti representing the different regions may be displayed to the user to guide the user to select the scan region of the target subject. In addition, after the user selects the scan region of the target subject, the positioning procedure of the target subject may be generated based on the selected scan region and the plurality of regions of the target subject. Conventionally, a user may need to manually determine and/or check the positioning procedure of the target subject, for example, by determining whether a desired region is within the detection region of the medical imaging device and/or whether the scanning table needs to be moved. Compared to the conventional way, the systems and methods for positioning the target subject disclosed herein may be fully or partially automated, more accurate and efficient by, e.g., reducing the workload of a user, cross-user variations, and the time needed for the system setting.

In some embodiments, one or more operations may be added or omitted. For example, a process for preprocessing (e.g., denoising) the image data of the target subject may be added after operation 710. As another example, operation 740 may be omitted. The scan region of the target subject may be automatically determined by one or more components of the imaging system 100 according to, for example, the imaging protocol of the target subject. The processing device 120 may determine a specific region of the target subject that the scan region belongs to, and determine a positioning procedure corresponding to the specific region of the target subject as the positioning procedure of the target subject.

FIG. 8 is a schematic diagram illustrating an exemplary target image 800 of a patient according to some embodiments of the present disclosure. The target subject 800 may be exemplary embodiment of a target image Ti as described in connection with FIG. 7.

As illustrated in FIG. 8, the target image 800 may include a reference subject model 801 of the patient and a plurality of representations (or referred to as annotations) of a plurality of regions of the patient. Merely by way of example, a representation 810 may correspond to a first region that can be imaged by a medical imaging device without moving a scanning table that supports the target subject, a representation 820 may correspond to a second region that can be imaged by the medical imaging device by moving the scanning table, and a representation 830 may correspond to a third region cannot be imaged by the medical imaging device.

In some embodiments, the plurality of representations of the plurality of regions may be marked using different colors in the target image 800. The target image 800 may be displayed to a user via a terminal device (e.g., the display 320 of the mobile device 300). The user may select a scan region via the terminal device and/or determine whether the position of the target subject needs to be adjusted based on the target image 800. A specific positioning procedure may be implemented based on the selected scan region.

As shown in FIG. 8, four exemplary scan regions (e.g., a first scan region 840, a second scan region 850, a third scan region 860, and a fourth scan region 870) are presented. The first scan region 840 and the second scan region 850 are within the first region, the third scan region 860 is within the second region, and the fourth scan region 870 is within the third region. Merely by way of example, if the user selects the first scan region 840 or the second scan region 850, it may indicate that the position of the target subject does not need to be adjusted, and the medical imaging device may directly scan the first scan region 840 or the second scan region 850. If the user selects the third scan region 860, it may indicate that the position of the target subject needs to be adjusted. A target position of the target subject may be determined, and the medical imaging device may scan the target subject when the target subject is at the target position. If the user selects the fourth scan region 870, a notification indicating that the fourth scan region 870 cannot be imaged by the medical imaging device may be generated.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For instance, the target image 800 may further include other information relating to the target subject, such as an imaging protocol of the target subject. As another example, the representations of different regions of the target subject may be displayed in other recognizable forms.

Figure 9:
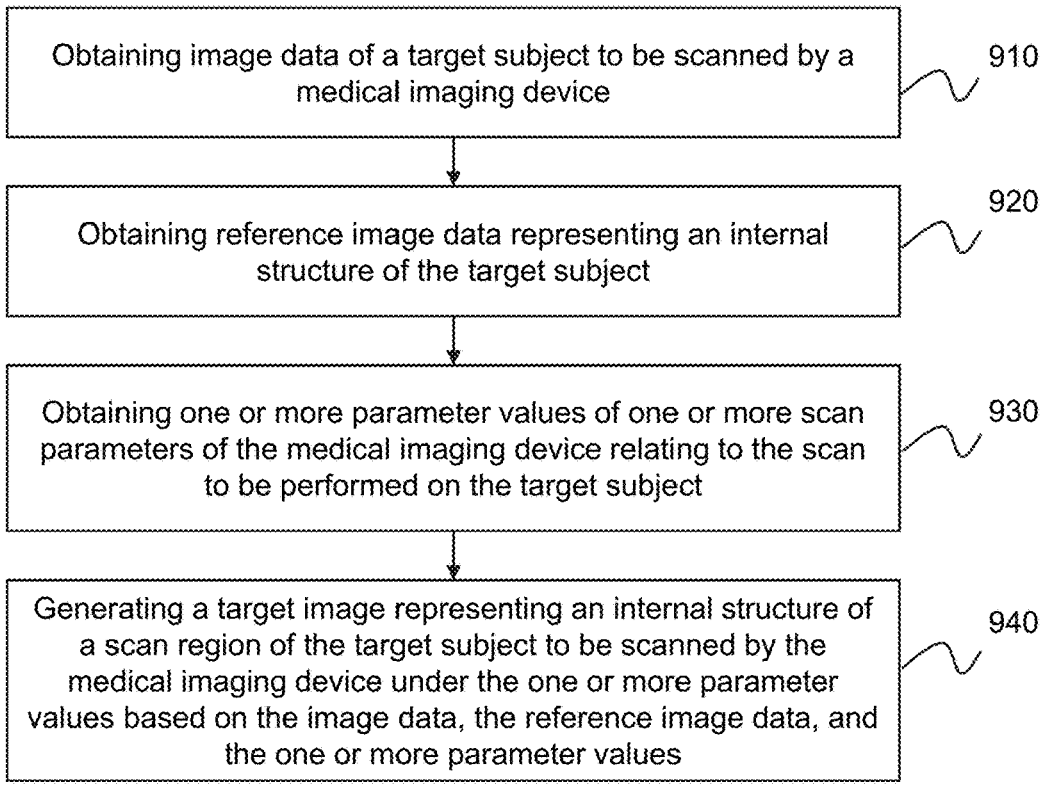
FIG. 9 is a flowchart illustrating an exemplary process for generating a target image Ti' representing an internal structure of a scan region of a target subject according to some embodiments of the present disclosure.

FIG. 9 is a flowchart illustrating an exemplary process for generating a target image Ti' representing an internal structure of a scan region of a target subject according to some embodiments of the present disclosure.

In 910, the processing device 120 (e.g., the acquisition module 510) may obtain image data of the target subject to be scanned by a medical imaging device (or referred to as a first medical imaging device).

The image data may be captured by an imaging capture device. For example, the image data may be captured after the target subject is placed at a scan position (e.g., lies on a scanning table). As another example, the image data may be captured after one or more components of the medical imaging device (e.g., a radiation source, a detector) is located at their respective target position(s). The image data may also illustrate the component(s) of the medical imaging device. In some embodiments, operation 910 may be performed in a similar manner with operation 610 as described in connection with FIG. 6, and the descriptions thereof are not repeated here.

In 920, the processing device 120 (e.g., the acquisition module 510) may obtain reference image data representing an internal structure of the target subject.

As used herein, the "representing an internal structure of the target subject" refers to representing an internal structure of the entire or a portion of the target subject. For example, the target subject may be a patient, and the reference image data may represent an internal structure of the entire patient. As another example, the reference image data may represent the internal structure of a specific region of the patient (e.g., the chest) to be scanned.

In some embodiments, the reference image data may include a historical anatomical image acquired by a second medical imaging device during a historical scan of the target subject. The second medical imaging device may include a CT device, an X-ray imaging device, an MRI device, a PET device, an ultrasound imaging device, a DR device, etc. The type of the second medical imaging device may be the same as or different from that of the medical imaging device. For example, both the medical imaging device and the second medical imaging device may be CT devices. As another example, the medical imaging device may be a DR device and the second medical imaging device may be a CT device.

In some embodiments, the reference image data may include a reference anatomical image of a reference subject. The reference anatomical image of the reference subject may represent an internal structure of the reference subject. The reference subject refers to a biological subject or a non-biological subject that has a similar internal structure to the target subject. For example, the target subject may be a patient, and the reference subject may be another patient or a virtual human body. As another example, if the target subject is the chest of a patient, the reference subject may be the chest of another patient or a virtual human body. Optionally, one or more features of the reference subject (e.g., a gender, a weight, a height, an age, a thickness, etc.) may be the same as or similar to that of the target subject. Because the reference subject and the target subject have similar internal structures, the reference image data may be used to represent the internal structure of the target subject.

In some embodiments, the reference image data may be stored in a storage device (e.g., the storage device 130, the storage device 220, the storage 390, or an external database). The processing device 120 may obtain the reference image data from the storage device. In some embodiments, a reference image library having a plurality of historical anatomical images of the target subject and/or a plurality of reference anatomical images of one or more reference subjects may be previously generated and stored in the storage device. The processing device 120 may select a historical anatomical image or a reference anatomical image from the reference image library, and designate the selected image as the reference image data.

Merely by way of example, the processing device 120 may select a historical CT image of the target subject from the reference image library because CT images may include more anatomical information compared with other images (e.g., a DR image). As another example, the processing device 120 may select the latest historical anatomical image of the target subject from the reference image library. As yet another example, the processing device 120 may select a reference anatomical image of a reference subject from the reference image library based on the appearance (e.g., the body shape, the posture) of the target subject (e.g., the body shape of the target subject, the posture of the target subject). The reference subject corresponding to the selected reference anatomical image may have the same feature information as or similar feature information to the target subject. Exemplary postures of the target subject may include a head first-supine (HFS) posture, a head first-prone (HFP) posture, a head first-decubitus right (HFDR) posture, a head first-decubitus left (HFDL) posture, a feet first-decubitus right (FFDR) posture, a feet first-decubitus left (FFDL) posture, a feet first-prone (FFP) posture, a feet first-supine (FFS) posture, etc. For example, both the target subject and the reference subject corresponding to the selected reference anatomical image may have HFS postures.

In 930, the processing device 120 (e.g., the acquisition module 510) may obtain one or more parameter values of one or more scan parameters of the medical imaging device relating to the scan to be performed on the target subject.

For example, the one or more scan parameters of the medical imaging device may include a scanning angle, a position of a radiation source, a position of a scanning table, an inclination angle of the scanning table, a position of a detector, a gantry angle of a gantry, a size of a field of view (FOV), a shape of a collimator, or the like, or any combination thereof.

In some embodiments, the processing device 120 may obtain a parameter value of a scan parameter based on an imaging protocol relating to the scan to be performed on the target subject. For example, the protocol may be predetermined and stored in a storage (e.g., the storage device 130). As another example, at least a portion of the protocol may be determined manually by a user (e.g., an operator). In some embodiments, the processing device 120 may determine a parameter value of a scan parameter based on the image data acquired in operation 910. For example, as described in connection with operation 910, the image data may illustrate a radiation source and/or a detector of the medical imaging device. The processing device 120 may determine the position of the radiation source and/or the detector based on the image data.

In 940, the processing device 120 (e.g., the analyzing module 520) may generate a target image Ti' representing an internal structure of a scan region of the target subject to be scanned by the medical imaging device.

The target image Ti' may be generated based on the image data, the reference image data, and the one or more parameter values of the one or more scan parameters. The scan region may be a region of the target subject that is estimated to be scanned by the medical imaging device. For example, according to the parameter value(s) of the scan parameter(s) and the image data, it can be speculated that the chest of the target subject may be scanned, and a target image Ti' illustrating an internal structure of the chest may be generated.

In some embodiments, the target image Ti' may be used to check the scan region of the target subject. For example, the target image Ti' may be displayed to a user, and the user may determine whether the scan region needs to be adjusted. In some embodiments, the processing device 120 may generate a reference subject model representing the internal structure of the target subject based on the image data and the reference image data. For example, a subject model may be determined based on the image data of the target subject, and the subject model may be combined with the reference image data to generate the reference subject mode. More descriptions regarding the generation of a reference subject model may be found elsewhere in the present disclosure, for example, operation 2130 in FIG. 22 and relevant descriptions thereof. The processing device 120 may further generate the target image Ti' based on the reference subject model and the one or more parameter value(s). For example, the processing device 120 may estimate a scan region of the target subject based on the parameter value(s) of the scan parameter(s), and segment a portion corresponding to the scan region from the reference subject model. The target image Ti' may display the segmented portion of the reference subject model. In some embodiments, the segmented portion may correspond to a cross-section of the scan region. For example, the segmented portion may correspond to a coronal plane of the scan region, that is, the target image Ti' may display the coronal plane of the scan region.

Figure 10:
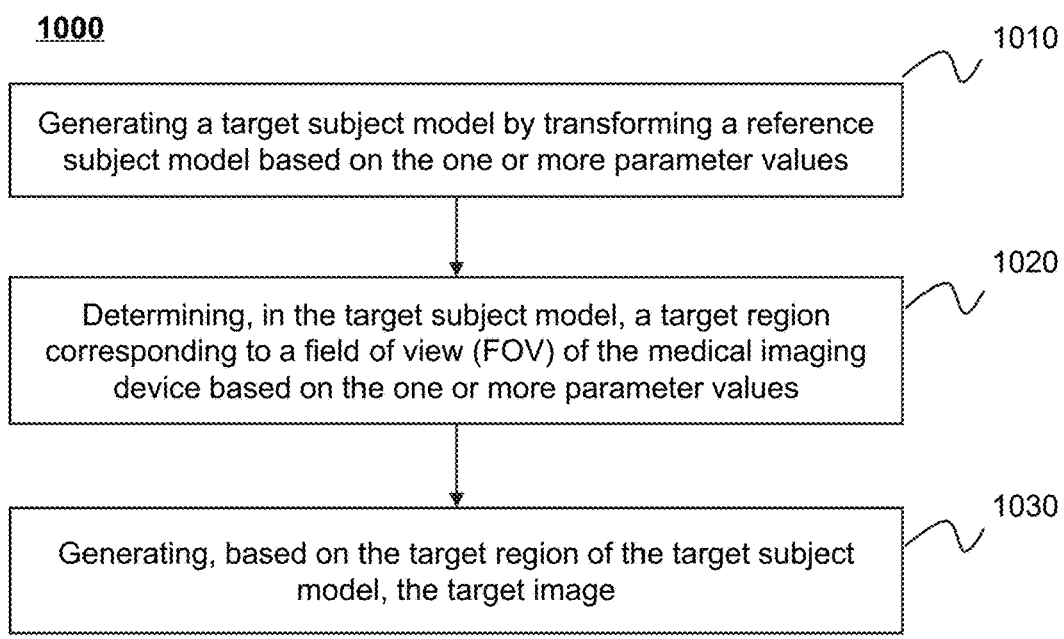
FIG. 10 is a flowchart illustrating an exemplary process for generating a target image Ti' representing an internal structure of a scan region of a target subject according to some embodiments of the present disclosure.

In some embodiments, the processing device 120 may generate the target image Ti' based on the reference subject model and the parameter value(s) by performing one or more operations of process 1000 as shown in FIG. 10.

In 1010, the processing device 120 (e.g., the analyzing module 520) may generate a target subject model by transforming the reference subject model based on the one or more parameter values.

In some embodiments, the processing device 120 may generate the target subject model by transforming the reference subject model based on the one or more parameter values of the one or more scan parameters, such that the target subject model may illustrate the internal structure of the target subject at a scanning angle of the medical imaging device. As used herein, a scanning angle of a medical imaging device refers to an angle at which the target subject is scanned. For example, the scanning angle for a CT device may be also referred to as a projection angle or a gantry angle. As another example, the medical imaging device may include a radiation source and a detector, the scanning angle refers to an angle formed between the target subject (e.g., a coronal plane of the target subject) and a line connecting the radiation source and the detector.

Figure 12A:
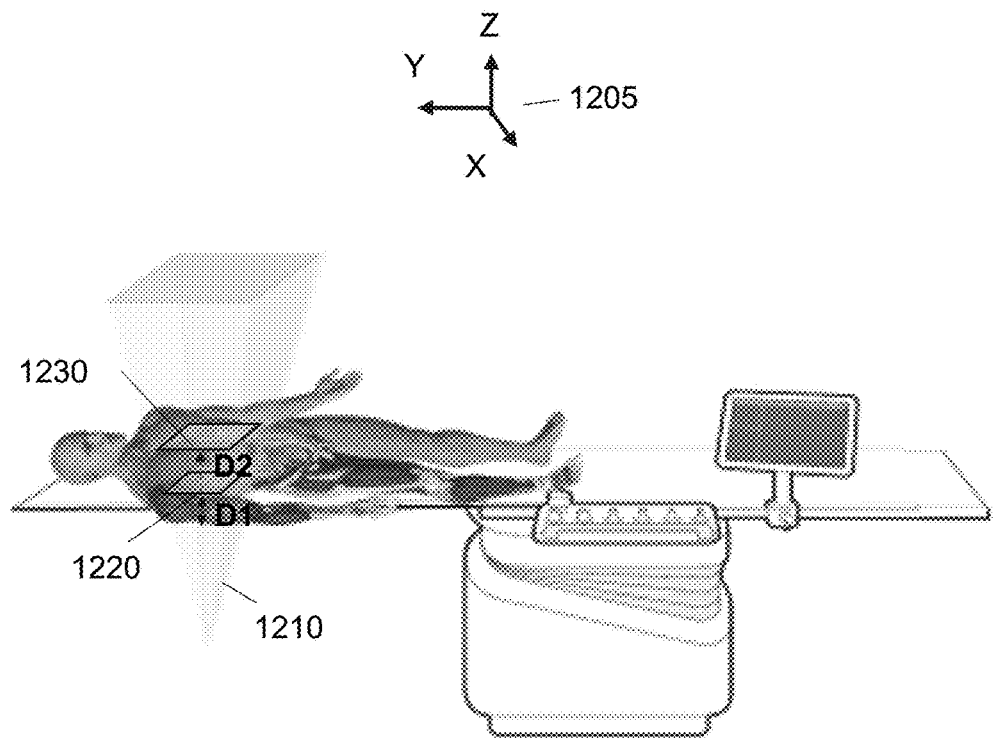
FIG. 12A is a schematic diagram illustrating an exemplary patient to be scanned by a medical imaging device according to some embodiments of the present disclosure.
Figure 12B:
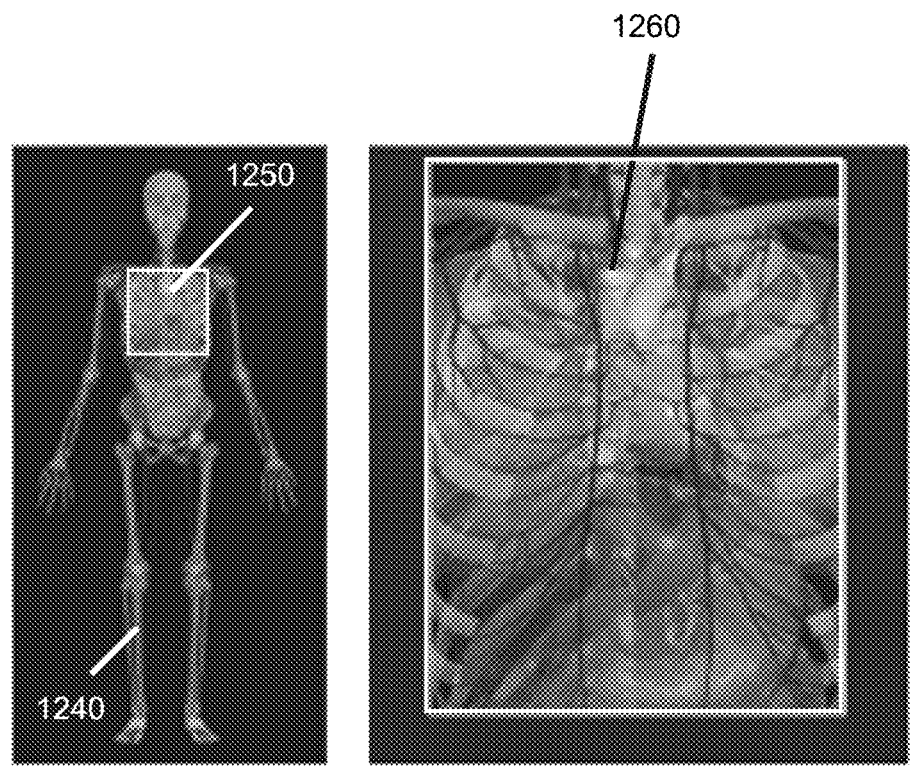
FIG. 12B is a schematic diagram illustrating an exemplary target subject model and an exemplary target image of the patient as shown in FIG. 12A according to some embodiments of the present disclosure.

Merely by way of example, as shown in FIG. 12A, the line connecting the radiation source and the detector may be along a positive Z-axis of a coordinate system 1205, and radiation beams may irradiate on the back of a patient. In such cases, a target subject model 1240 illustrating the internal structure of the patient seen from the back of the patient may be generated as shown in FIG. 12B. As shown in FIG. 13B, the line connecting the radiation source and the detector may be along a negative X-axis of the coordinate system 1205, and radiation beams may irradiate on the side of the patient. A target subject model 1325 illustrating the internal structure of the patient seen from the side of the patient may be generated as shown in FIG. 13B.

In some embodiments, the scanning angle of the medical imaging device may be obtained in operation 930. Alternatively, the scanning angle may be determined based on at least one scan parameter associated with the scanning angle, such as the position of the radiation source, the position of the detector, the gantry angle of the gantry, or the like, or any combination thereof. In some embodiments, the reference subject model may be a 3D model, and the processing device 120 may generate the target subject model by transforming (e.g., rotating) the reference subject model according to the scanning angle. In some embodiments, the processing device 120 may directly generate the target subject model based on the reference image data, the image data, and the scanning angle.

In some embodiments, the target subject model may be represented in a 3D image or a 2D image. For example, the target subject model may be represented in an image that includes pixels or voxels corresponding to the target subject and pixels or voxels corresponding to a background. In some embodiments, the pixel value of each pixel (or the voxel value of each voxel) in the background may be set as a constant value, such as a value selected from a range of 0-255. Merely by way of example, FIG. 12B illustrates an exemplary target subject model 1240 representing a patient. In some embodiments, the target subject model 1240 may be a 3D model or a 2D model. In some embodiments, operation 1010 may be omitted. The target image may be generated directly based on the reference subject model. In some embodiments, the target image may be generated based on the subject model, and the generation of the reference subject model and the target subject model may be omitted.

In 1020, the processing device 120 (e.g., the analyzing module 520) may determine, in the target subject model, a target region corresponding to an FOV of the medical imaging device based on the one or more parameter values.

As used herein, an FOV of a medical imaging device refers to an area that can be covered by radiation rays emitted by the radiation source. The FOV may cover the scan region of the target subject. For example, the scan region may be a portion of the target subject within the FOV of the medical imaging device. Optionally, the FOV may cover an area outside the scan region, such as a region on a scanning table.

In some embodiments, the processing device 120 may determine one or more parameters relating to the FOV based on the parameter value(s) of the one or more scan parameters. For example, the size and/or shape of the FOV may be determined based on the shape of a collimator of the medical imaging device. As another example, the position of the FOV relative to the target subject may be determined based on the position of the target subject and one or more of the scanning angle, the position of the radiation source, the position of the detector, or the like. Additionally or alternatively, the size of the FOV may be associated with on activated detector unit(s) of the detector. For instance, the detector may be a flat panel detector including a plurality of detector units. At least a portion of the detector units may be activated during the scan on the target subject. The size of the FOV may be associated with on an area covered by the activated detector units. The processing device 120 may further determine the target region corresponding to the FOV from the target subject model based on the parameter(s) of the FOV. For example, the size of the target region may be determined based on the size of the FOV. The shape of the target region may be determined based on the shape of the FOV. The position of the target region relative to the target subject model may be determined based on the position of the FOV relative to the position of the target subject.

In some embodiments, the FOV of the medical imaging device may be measured at a certain distance with respect to the scanning table (or another reference object, such as the radiation source). For example, as illustrated in FIG. 12A, the target subject may be a patient positioned on the scanning table of the medical imaging device. A radiation beam 1210 may be emitted toward the target subject. At a first distance D1 away from the scanning table, the medical imaging device may have a first FOV 1220. At a second distance D2 away from the scanning table, the medical imaging device may have a second FOV 1230. The first distance D1 may be shorter than the second distance D2, and the first FOV 1220 may be smaller than the second FOV 1230. In other words, a cross section of the scan region of the patient at the first distance D1 may be smaller than that at the second distance D2. In some embodiments, each of or one of the first FOV 1220 and the second FOV 1230 may be used to determine the target region. In some embodiments, the second FOV 1230 may be used to determine the target region so that the target image Ti' generated based on the target region may illustrate more information regarding the scan region.

In 1030, the processing device 120 (e.g., the analyzing module 520) may generate, based on the target region of the target subject model, the target image Ti'.

The target image Ti' may include the target region corresponding to the FOV of the medical imaging device. For example, the target region may be designated as the target image Ti'. As another example, the target image Ti' may be generated by enlarging the target region. In some embodiments, because the target subject model is displayed at a specific angle according to the scanning angle of the medical imaging device, and the target region is segmented from the target subject model based on the FOV of the medical imaging device, the target region and/or the target image Ti' may be regarded as a simulated image of a resulting image of the scan. The target region and/or the target image Ti' may be used to check the scan region of the target subject.

In some embodiments, the processing device 120 may transmit the target image Ti' to a terminal device (e.g., the terminal device 140) of a user. The terminal device may display the target image Ti' to the user, which may allow the user to observe the internal structure of the scan region (i.e., a portion that is covered by the FOV) and check the scan region. For example, based on the target image Ti', the user may determine whether the scanning table needs to be adjusted to adjust the position of the scan region. As another example, based on the target image Ti', the user may determine whether the scanning angle needs to be adjusted to adjust the angle from which the scan region is scanned.

In some embodiments, the target region may be marked in the target subject model. For example, the processing device 120 may add an annotation regarding the target region (e.g., a box enclosing the target region). The annotation may represent the position of the target region with respect to the target subject model. In some embodiments, the processing device 120 may transmit the target subject model to the terminal device of the user. The terminal device may jointly display the target subject model and the target image Ti'.

For illustration purposes, FIG. 12B illustrates a schematic diagram of an exemplary target subject model 1240 and an exemplary target image Ti' 1260 of the patient as shown in FIG. 12A according to some embodiments of the present disclosure. As shown in FIG. 12B, the target subject model 1240 may represent the internal structure of a patient. A target region 1250 may be marked in the target subject model 1240 using a box. The target image Ti' 1260 may illustrate an enlarged view of the target region 1250.

Figure 11:
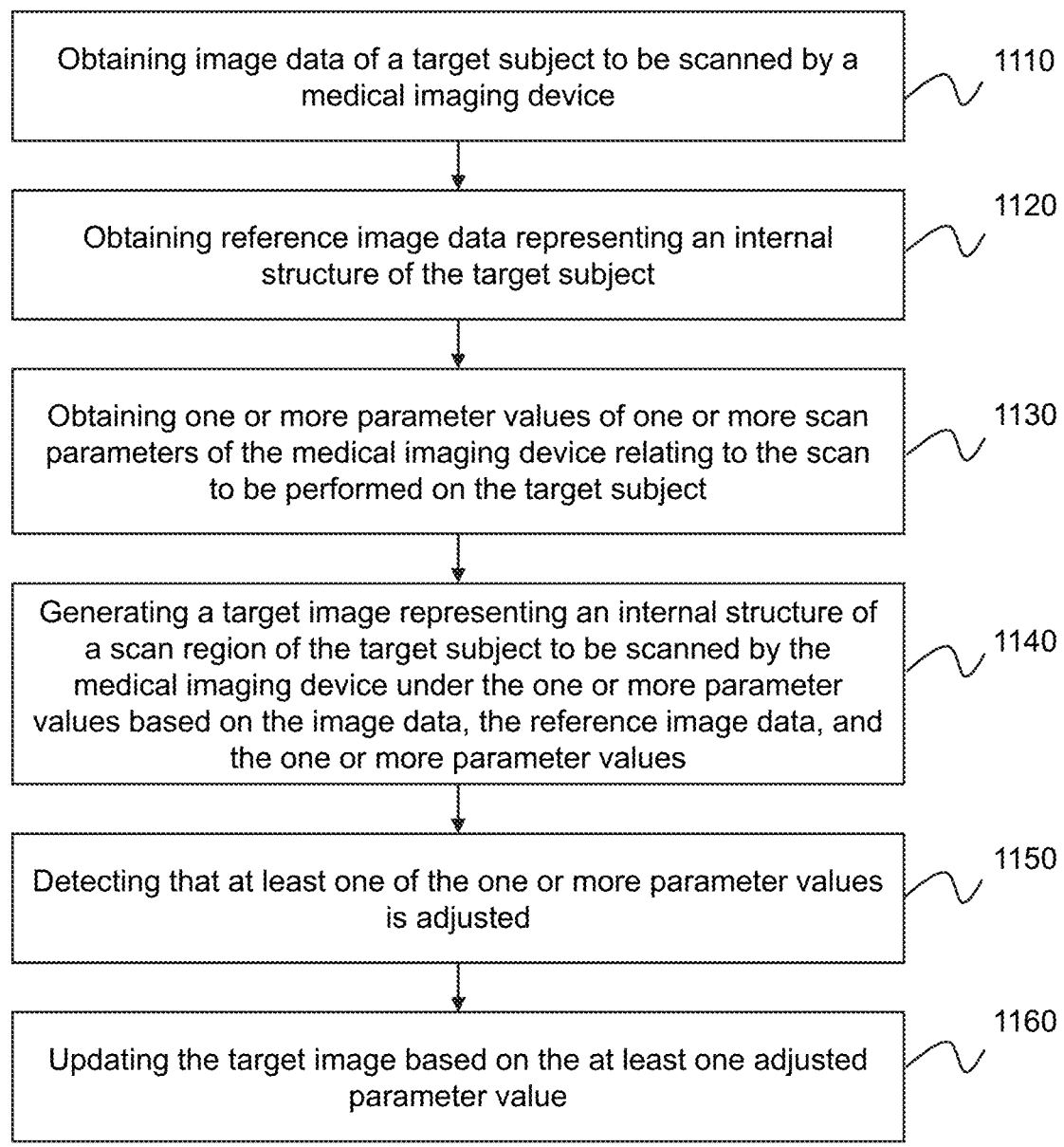
FIG. 11 is a flowchart illustrating an exemplary process for updating the target image Ti' according to some embodiments of the present disclosure.

FIG. 11 is a flowchart illustrating an exemplary process for updating the target image Ti' according to some embodiments of the present disclosure.

Operations 1110 to 1140 may be performed in a similar manner with operations 910 to 940, respectively, as described in connection with FIG. 9, and the descriptions thereof are not repeated here.

In 1150, the processing device 120 (e.g., the analyzing module 520) may detect that at least one of the one or more parameter values is adjusted.

In some embodiments, a user (e.g., an operator) may input an instruction for adjusting the parameter value of a scan parameter via a terminal device (e.g., the terminal device 140). The processing device 120 may detect the adjustment of the parameter value of the scan parameter based on the instruction inputted by the user. For example, the user may input an instruction for adjusting the position of the scanning table. As another example, the user may input an instruction for adjusting the position of the radiation source. Alternatively, the user may manually move the scanning table, and a position encoder may detect the position change of the scanning table and transmit information regarding the position change of the scanning table to the processing device 120.

In some embodiments, the image capturing device may be configured to capture a plurality of sets of image data in the examination room continuously or intermittently (e.g., periodically). The processing device 120 may detect that a parameter value of a scan parameter changes based on the sets of image data. For example, the processing device 120 may detect a position change of the scanning table by analyzing the sets of image data.

In 1160, in response to determining that at least one of the one or more parameter values is adjusted, the processing device 120 (e.g., the analyzing module 520) may update the target image Ti' based on the at least one adjusted parameter value.

In some embodiments, the processing device 120 may update the target region by adjusting at least one of a position of the target region in the target subject model, a size of the target region, a shape of the target region, or the like, or any combination thereof. The processing device 120 may further update the target image Ti' based on the updated target region.

In some embodiments, the adjustment of the at least one of the one or more parameter values may cause a change in a position of the target subject and/or the radiation source without changing the scanning angle. The processing device 120 may update the position of the target region in the target subject model. For example, the adjustment of the at least one of the one or more parameter values may cause a change in a position of the target subject of the medical imaging device on a plane perpendicular to the line connecting the radiation source and the detector of the medical imaging source. As another example, a radiation source of the medical imaging device may be located at a first initial position before the adjustment of the at least one of the one or more parameter values. A detector of the medical imaging device may be located at a second initial position before the adjustment of the at least one of the one or more parameter values. The adjustment of the at least one of the one or more parameter values may cause the radiation source to move from the first initial position to a first target position and cause the detector to move from the second initial position to a second target position. A first line connecting the first initial position and the second initial position may be parallel to a second line connecting the first target position and the second target position, such that the scanning angle may not change with the position change of the radiation source and the detector.

For example, referring to FIG. 12A, the scanning may be along the positive Z-axis of the coordinate system 1205. The movement (e.g., a translation and/or rotation) of the scanning table on the X-Y plane of the coordinate system 1205 (i.e., a plane perpendicular to the scanning angle) may cause the target subject to move on the X-Y plane. The movement of a C-arm for supporting the radiation source on the X-Y plane may cause the radiation source to move on the X-Y plane. When the target subject and/or the radiation source move on the X-Y plane, the first or second FOV may also move on the X-Y plane. Accordingly, the processing device 120 may update the target region by adjusting the position of the target region in the target subject image based on the at least one adjusted parameter value.

In some embodiments, the adjustment of the at least one of the one or more parameter values may cause a change in a size of the FOV of the medical imaging device. For example, referring to FIG. 12A, if the scanning table moves along the Z-axis of the coordinate system 1205 (i.e., a direction parallel to the scanning angle), the patient may also move along the Z-axis and the size of the first and second FOVs may change. Other exemplary scan parameters that may cause the change in the size of the FOV may include a position of a C-arm of the medical imaging device (e.g., a C-arm CT scanner) along the Z-axis, a position of the radiation source along the Z-axis, a position of a detector of the medical imaging device, an SID, a count of activated detector units of the detector, or the like. The processing device 120 may update the target region by adjusting a size of the target region in the target subject image based on the at least one adjusted parameter value. For example, the processing device 120 may enlarge the target region or reduce the target region based on the adjusted parameter value(s). The processing device 120 may further update the target image Ti' based on the updated target region.

In some embodiments, the adjustment of the at least one of the one or more parameter values may cause a change in a shape of the FOV of the medical imaging device. For example, the shape of the FOV may change if the shape of the collimator of the medical imaging device changes. The processing device 120 may update the target region by adjusting a shape of the target region based on the at least one adjusted parameter value. The processing device 120 may then update the target image Ti' based on the updated target region.

In some embodiments, the adjustment of the at least one of the one or more parameter values may cause a change in the scanning angle of the medical imaging device. For example, the scanning angle may change if the inclination angle of the scanning table (e.g., an angle between the X-Y plane of the coordinate system 1205 and an upper surface of the scanning table) changes. As another example, the scanning angle may change if the gantry angle and/or an irradiation angle of the radiation source changes. The processing device 120 may update the target region by updating the target subject model based on the changed scanning angle. For instance, the processing device 120 may update the target subject model (e.g., by rotating the target subject model) based on the changed scanning angle. The processing device 120 may further update the target region based on the updated target subject model and update target image Ti' based on the updated target region.

Figure 13A:
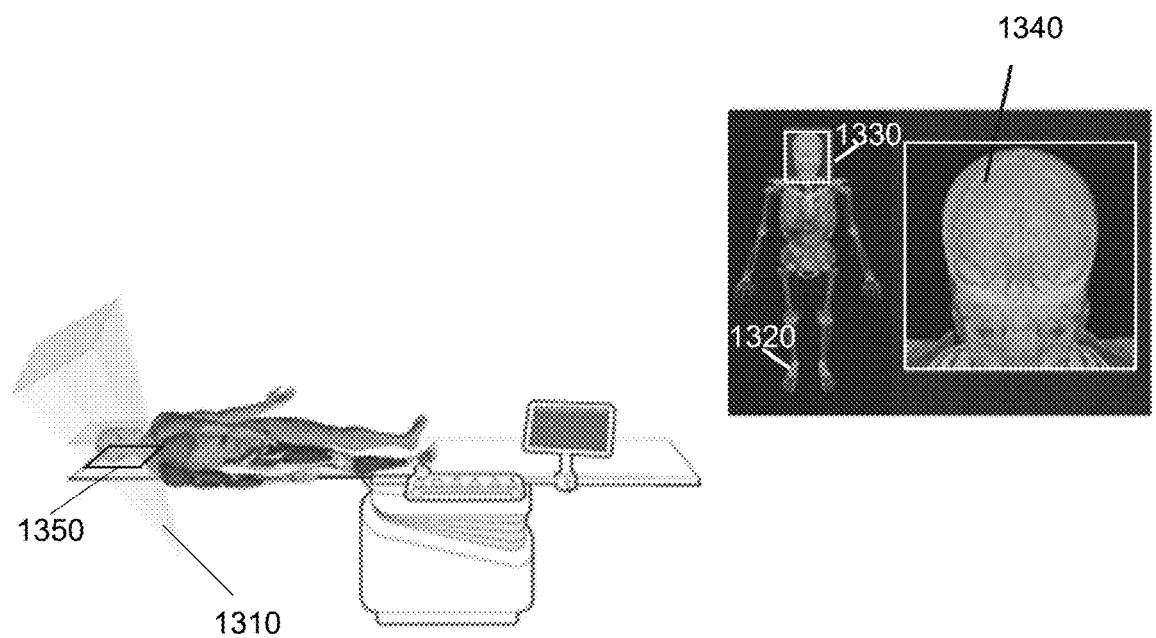
FIG. 13A is a schematic diagram illustrating the update of an exemplary target image Ti' based on an adjusted scanning angle according to some embodiments of the present disclosure.
Figure 13B:
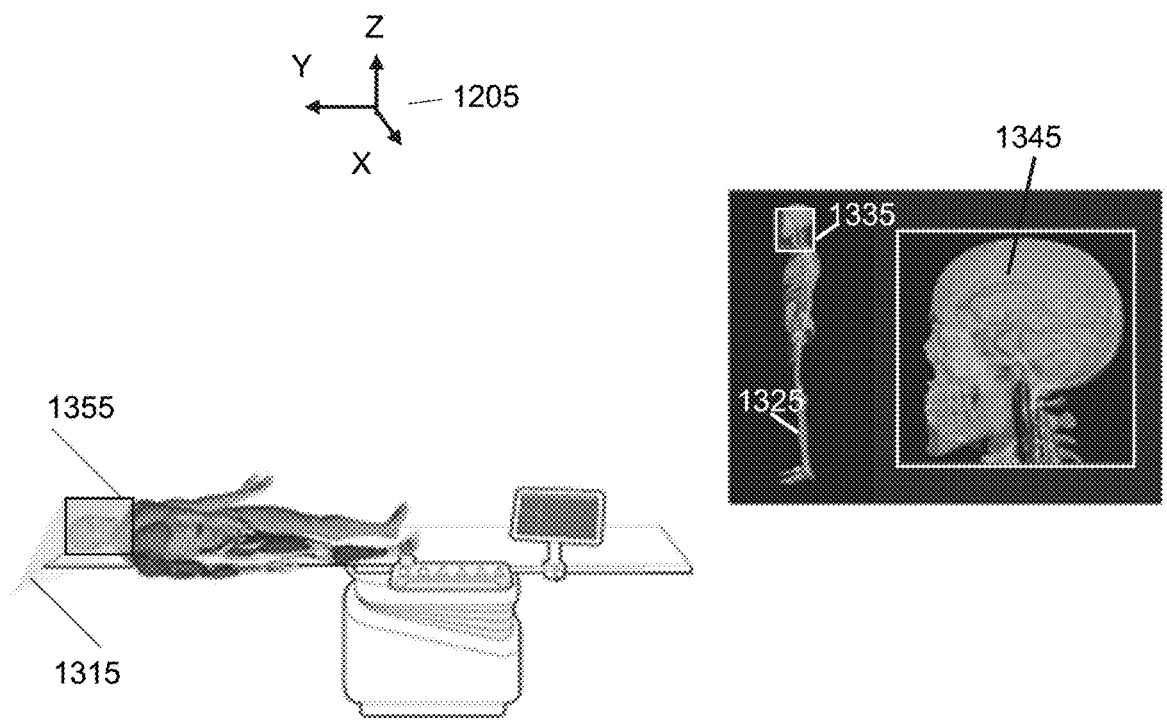
FIG. 13B is a schematic diagram illustrating the update of an exemplary target image Ti' based on an adjusted scanning angle according to some embodiments of the present disclosure.

For example, FIGS. 13A-13B are schematic diagrams illustrating the update of an exemplary target image Ti' based on an adjusted scanning angle. As shown in FIG. 13A, the scanning angle may be different from that as shown in FIG. 12A, and a radiation beam 1310 may be emitted to the head of the patient. An updated target subject model 1320 corresponding to the scanning angle in FIG. 13A may be generated. A target region 1330 corresponding to an FOV 1350 of the medical imaging device may be identified in the updated target subject model 1320. A target image 1340 may represent an enlarged view of the target region 1330.

As shown in FIG. 13B, the scanning angle may be different from that as shown in FIG. 13A. A radiation beam 1315 may be emitted toward the head of the target subject. An updated target subject model 1325 may be generated by updating the target subject model 1320 based on the adjusted scanning angle. An updated target region 1335 may be identified in the updated target subject model 1325. The updated target region 1335 may correspond to an FOV 1355 of the medical imaging device. Accordingly, an updated target image 1345 may be generated based on the updated target region 1335.

According to some embodiments of the present disclosure, before a scan is performed on the target subject, a target image Ti' representing an internal structure of an estimated scan region of the scan may be generated based on the image data, the reference image data, and the one or more parameter values of the scan parameter(s). In addition, the target image Ti' may be updated if the value of one or more scan parameters change, for example, if the scanning table and/or the radiation source is moved by a user. In some conventional imaging methods, before the scan on the target subject, a first pre-scan may be performed on the target subject to acquire an image of the scan region, and a user may determine whether the scan region needs to be adjusted based on the image. If the value of one or more scan parameters changes, the scan region may also change. A second pre-scan may need to be performed on the target subject in order to determine exactly which portion the target subject is the changed scan region. By generating the target image Ti' and updating the target image Ti' using the systems and methods disclosed herein, the user may check the scan region and/or the changed scan region in an intuitive and convenient way without performing pre-scans on the target subject. Thus, the scan on the target subject may be performed more efficiently and the workload of the user may be effectively reduced.

In some embodiments, one or more additional operations not described may be added, and/or one or more of the operations discussed may be omitted. Additionally, the order of the operations illustrated in FIGS. 9-11 and described above is not intended to be limiting. For example, process 1100 may further include an operation of estimating a dose distribution relating to the target subject using the target subject model determined in operation 1140 or operation 1010. The dose distribution may include a dose delivered to one or more portions of the target subject and/or an absorbed dose that is absorbed by the one or more portions of the target subject. In some embodiments, the dose distribution may be estimated during the scan on the target subject. Optionally, the one or more portions of the target subject model may be displayed using different colors in the target subject model to indicate different doses delivered to or absorbed by the one or more portions of the target subject. Additionally or alternatively, the target image Ti' may be displayed to a user (e.g., an operator) via a terminal device. The target image Ti' may include an annotation indicating a dose delivered to or absorbed by each of one or more portions of the scan region of the target subject. The user may know the dose distribution relating to the target subject in a more intuitive and convenient manner. More descriptions regarding the estimation of the dose distribution may be found elsewhere in the present disclosure, for example, in FIGS. 28 and 29 and the descriptions thereof.

Figure 14:
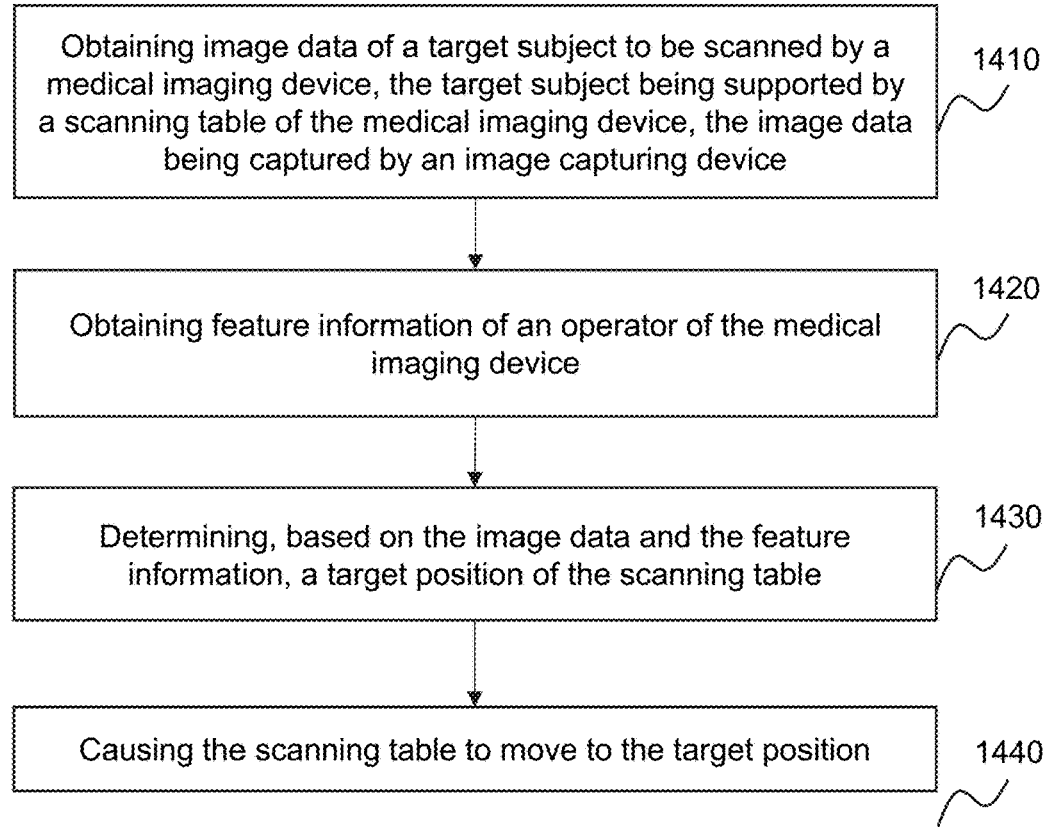
FIG. 14 is a flowchart illustrating an exemplary process for scan preparation according to some embodiments of the present disclosure.

FIG. 14 is a flowchart illustrating an exemplary process for scan preparation according to some embodiments of the present disclosure. In some embodiments, process 1400 may be performed before a scan to be performed on a target subject by a medical imaging device. For example, one or more operations of the process 1400 may be performed after process 700 and/or process 900, and before process 1500, process 1700, and/or process 1900.

In 1410, the processing device 120 (e.g., the acquisition module 510) may obtain image data of a target subject to be scanned by a medical imaging device. The target subject may be supported by a scanning table (e.g., scanning table 114) of the medical imaging device. The image data may be captured by a first image capturing device.

Operation 1410 may be performed in a similar manner as operation 610 as described in connection with FIG. 6, and the descriptions thereof are not repeated here.

In 1420, the processing device 120 (e.g., the acquisition module 510) may obtain feature information of an operator of the medical imaging device.

In some embodiments, the operator may be a doctor, a technician, or another person who can operate the medical imaging device (e.g., the medical imaging device 110) before and/or during the scan of the target subject. The feature information of the operator may include a height, a width, a thickness, or the like, of the operator. In some embodiments, the feature information of the operator may be previously determined and stored in a storage device (e.g., the storage device 130, the storage device 220, the storage 390, or an external source). The processing device 120 may retrieve the feature information of the operator from the storage device. In some embodiments, the term "operator" and "user" may be used interchangeably.

Additionally or alternatively, the feature information of the operator may be determined based on image data captured by, for example, one or more image capturing devices (e.g., the first image capturing device, a second image capturing device, another image capturing device). For example, the processing device 120 may obtain second image data of the operator. The second image data may be captured by the second image capturing device. The first image capturing device and the second image capturing device may be of a same type or different types. The second image capturing device may be the same device as or a different device from the first image capturing device. In some embodiments, the second image data may be of a same set of image data as the image data of the target subject as described in connection with operation 1410. Merely by way of example, the image data of the target subject may also include a representation of the operator and be used as the second image data for determining the feature information of the operator.

The processing device 120 may further determine the feature information of the operator based on the second image data. Taking the determination of the height of the operator as an example, the processing device 120 may identify a representation of the operator in the second image data, and determine a reference height of the representation of the operator in the image domain. Merely for illustration purposes, a first point at the feet of the operator and a second point at the top of the head of the operator may be identified in the second image data. A pixel distance (or voxel distance) between the first point and the second point may be determined as the reference height of the representation of the operator in the image domain. The processing device 120 may then determine the height of the operator in the physical world based on the reference height and one or more parameters (e.g., intrinsic parameters, extrinsic parameters) of the second image capturing device that captures the second image data. Additionally or alternatively, the processing device 120 may determine the feature information of the operator by generating a model representing the operator based on the second image data. The model representing the operator may be generated in a similar manner as that of the subject model as described elsewhere in the present disclosure (e.g., FIG. 6 and descriptions thereof).

In 1430, the processing device 120 (e.g., the analyzing module 520) may determine, based on the image data and the feature information of the operator, a target position of the scanning table.

The target position of the scanning table refers to a suitable position where the scanning table needs to be located during the scan of the target subject according to, for example, feature information of the operator and/or feature information of the target subject.

In some embodiments, the processing device 120 may determine feature information of the target subject based on the image data. The feature information of the target subject may include a height, a width, a thickness, a posture (e.g., a prone posture, a lateral recumbent posture), or the like, of the target subject. The feature information of the target subject may be determined based on the image data in a similar manner as how the feature information of the operator is determined based on the second image data as described in connection with operation 1420. The processing device 120 may further determine the target position (e.g., a height) of the scanning table based on the feature information of the target subject and the feature information of the operator.

For example, if the target subject lies on the scanning table in a supine posture or a prone posture, the processing device 120 may determine the height of the scanning table based on the height of the operator and the thickness of the target subject. As another example, if the target subject lies on the scanning table in a lateral recumbent posture, the processing device 120 may determine the height of the scanning table based on the height of the operator and the width of the target subject. In some embodiments, a sum of the thickness (or the width) of the target subject and the determined height of the scanning table may be equal to a certain percentage (e.g., ⅔, ½, or the like) of the height of the operator. The height of the scanning table may be represented as, for example, a Z-axis coordinate of the surface of the scanning table where the target subject lies on in the coordinate system 170 as shown in FIG. 1.

According to some embodiments of the present disclosure, the height of the scanning table may be determined and adjusted automatically based on the height of the operator and the thickness (or the width) of the target subject, which may be convenient for the operator to perform an operation (e.g., a surgery operation) on the target subject. Conventionally, after the target subject lies on the scanning table, the operator may need to manually determine and/or check the height of the scanning table, for example, by determining whether the height of the scanning table is suitable for the operator to perform an operation on the target subject. For target subjects with different body shapes and operators with different heights, the height of the scanning table may be different. Compared to the conventional way, the automated systems and methods for determining the target position of the scanning table disclosed herein may be more accurate and efficient by, e.g., reducing the workload of a user, cross-user variations, and the time needed for scan preparation.

In 1440, the processing device 120 (e.g., the control module 530) may cause the scanning table to move to the target position.

In some embodiments, the processing device 120 may send an instruction to the scanning table or a driving apparatus of the scanning table to cause the scanning table to move to the target position. The instruction may include various parameters related to the movement of the scanning table. Exemplary parameters related to the movement of the scanning table may include a distance of movement, a direction of movement, a speed of movement, or the like, or any combination thereof.

In some embodiments, before operation 1440, the target position of the scanning table determined in operation 1430 may be further checked and/or adjusted. For example, the target position of the scanning table may be manually checked and/or adjusted by a user of the imaging system 100. As another example, a collision detection may be performed. Specifically, the processing device 120 may obtain environment data. The environment data may include a position, a size, or the like, or any combination thereof, of one or more other components (e.g., a component of the imaging system 100, a floor, a wall, a person) in an examination room where the target subject is located. The environment data may be obtained from one or more components (e.g., the image capturing device 160) of the imaging system 100. For example, the environment data may be obtained based on real-time image data captured by an image capturing device (e.g., the image capturing device 160) in the examination room. The processing device 120 may further determine whether an obstacle exists in a moving trajectory of the scanning table to the target position based on the environment data (or a collision between the scanning table and another component is likely to occur). The moving trajectory of the scanning table may be determined based on an initial position of the scanning table (i.e., the position of the scanning table obtained in operation 1420) and the target position of the scanning table. Merely by way of example, a route between the initial position and the target position with the shortest distance may be determined as the moving trajectory of the scanning table. In some embodiments, the moving trajectory of the scanning table may be automatically determined by one or more components of the imaging system 100, or manually set by a user of the imaging system 100.

In response to determining that an obstacle exists in the moving trajectory of the scanning table to the target position, the processing device 120 may generate a notification. The notification may indicate that an obstacle exists in the moving trajectory of the scanning table to the target position, for example, the notification may include position information of the obstacle. The notification may be in the form of a text, a voice, an image, a video, a haptic alert, or the like, or any combination thereof. For example, the processing device 120 may transmit the notification to a terminal device (e.g., the terminal device 140) of an operator (e.g., a doctor) of the imaging system 100. The terminal device may output the notification to the user. Optionally, the user may input an instruction or information in response to the notification. Merely by way of example, the user may manually adjust the target position of the scanning table or remove the obstacle. In some embodiments, the collision detection may be performed according to process 3600 as described in connection with FIG. 36.

In some embodiments, after the scanning table is moved to the target position, the processing device 120 may perform one or more additional operations to prepare for the scan on the target subject. For example, the processing device 120 may determine a rotation scheme of the medical imaging device during the scan of the target subject based on a position of an imaging isocenter of the medical imaging device and a position of a POI of the target subject. More descriptions for determining the rotation scheme of the medical imaging device may be found elsewhere in the present disclosure (e.g., FIG. 15, and descriptions thereof). As another example, the processing device 120 may adjust position(s) of component(s) of the medical imaging device such that a scan region is targeted by an imaging isocenter of the medical imaging device. More descriptions for adjusting the position(s) of the component(s) of the medical imaging device may be found elsewhere in the present disclosure (e.g., FIG. 17, and descriptions thereof). As still another example, the processing device 120 may generate a reference subject model representing the internal structure of the target subject, and cause a terminal device to display the reference subject model. More descriptions for generating the reference subject model may be found elsewhere in the present disclosure (e.g., FIG. 21, and descriptions thereof).

Figure 15:
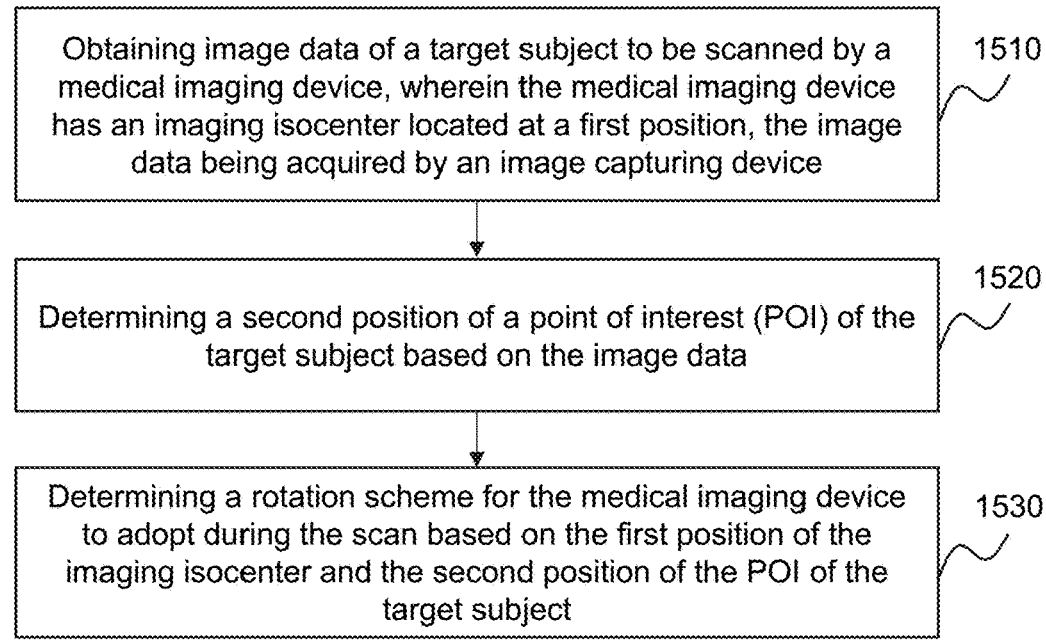
FIG. 15 is a flowchart illustrating an exemplary process for determining a rotation scheme of a medical imaging device according to some embodiments of the present disclosure.

FIG. 15 is a flowchart illustrating an exemplary process for determining a rotation scheme of a medical imaging device according to some embodiments of the present disclosure.

In some embodiments, process 1500 may be performed before a scan to be performed on a target subject by a medical imaging device. In some embodiments, process 1500 may be performed after process 700, process 900, and/or process 1400. In some embodiments, one or more operations of process 1500 may be performed after process 1400 as described in connection with FIG. 14, in which a scanning table of the medical imaging device is automatically adjusted according to feature information (e.g., the width, the thickness) of the target subject and feature information (e.g., the height) of an operator of the medical imaging device.

The medical imaging device may have an imaging isocenter located at a first position. The first position refers to the position of the imaging isocenter before the scan is performed on the target subject. In some embodiments, the first location of the imaging isocenter may be represented by a coordinate of the imaging isocenter in a coordinate system (e.g., the coordinate system 170). In some embodiments, the first position of the imaging isocenter may be determined based on a position of a component (e.g., the C-shape gantry) of the medical imaging device in the coordinate system (e.g., a coordinate of the component of the medical imaging device in the coordinate system 170) and a position of the imaging isocenter relative to the component of the medical imaging device. In some embodiments, the imaging isocenter may be previously determined, for example, when the medical imaging device is mounted, and stored in a storage device (e.g., the storage device 130) of the imaging system 100.

In 1510, the processing device 120 (e.g., the acquisition module 510) may obtain image data of a target subject to be scanned by a medical imaging device. The image data may be acquired by an image capturing device. More descriptions for obtaining the image data of the target subject may be found elsewhere in the present disclosure (e.g., operation 610 in FIG. 6, and descriptions thereof).

In 1520, the processing device 120 (e.g., the analyzing module 520) may determine a second position of a point of interest (POI) of the target subject based on the image data.

The POI of the target subject may be a specific point of a scan region of the target subject. The scan region may include one or more physical portions (e.g., tissue, an organ) of the target subject to be imaged (or examined or treated) by the medical imaging device. For example, the specific point may be a center point of the scan region. As another example, the specific point may be a central point of a certain portion of the scan region. FIG. 16C is a schematic diagram illustrating an exemplary process for determining a POI of a target subject according to some embodiments of the present disclosure. Merely by way of example, as shown in FIG. 16C, the scan region may be the chest of the target subject, and the POI may be a central point 1660 of the heart of the target subject, wherein the distance between the central point 1660 and the scanning table is about 2/3 of the thickness of the chest of the target subject.

Figure 16A:
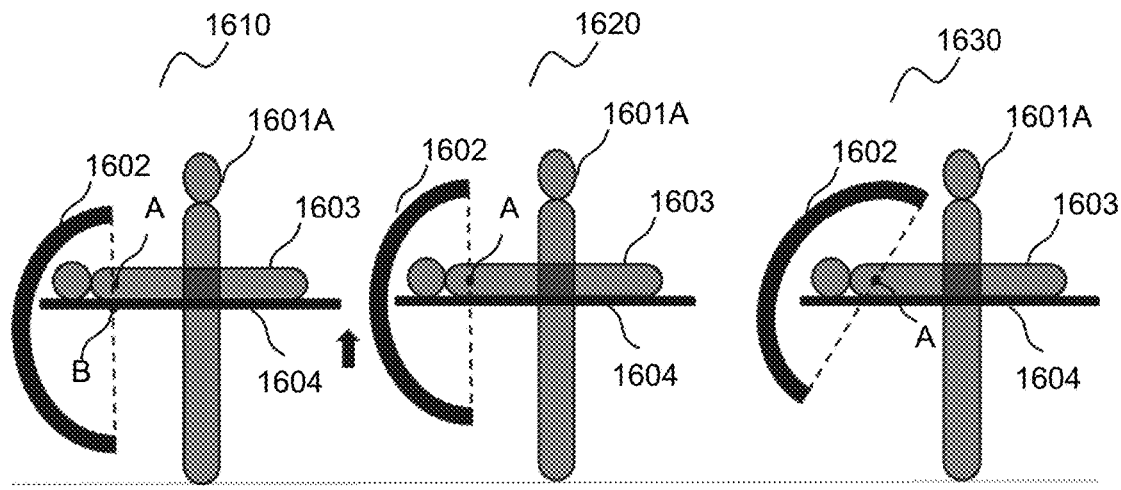
FIG. 16A is a schematic diagram illustrating an exemplary process for determining a rotation scheme of a medical imaging device according to some embodiments of the present disclosure.
Figure 16B:
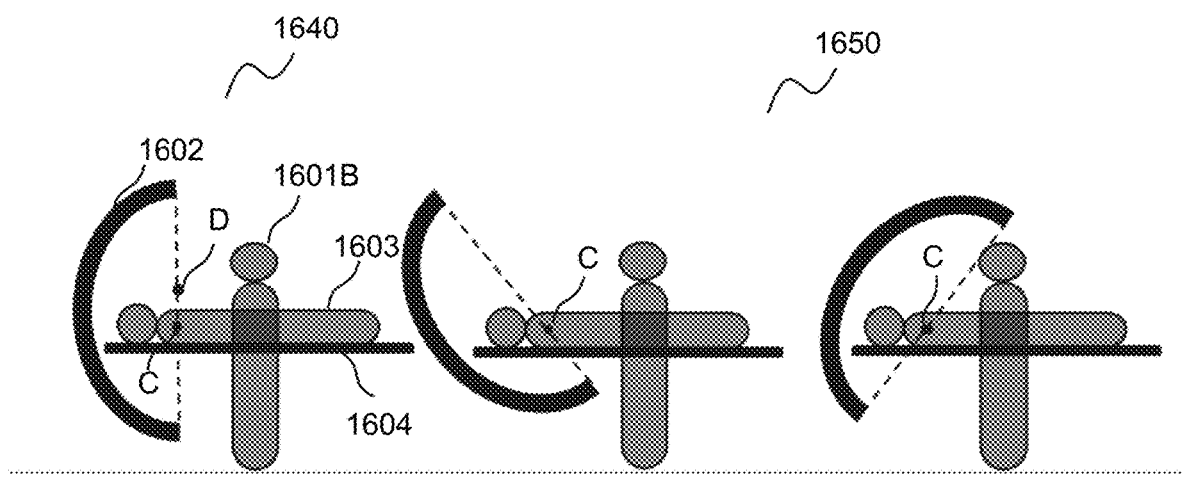
FIG. 16B is a schematic diagram illustrating an exemplary process for determining a rotation scheme of a medical imaging device according to some embodiments of the present disclosure.

Alternatively, the POI of the target subject may be adjusted according to the position of the target subject relative to the medical imaging device. Merely by way of example, the medical imaging device may have a C-arm as shown in FIGS. 16A-16C. It is assumed that an original POI of the target subject may be the central point 1660 of the heart of the target subject. However, the imaging isocenter of the medical imaging device may be located at a point 1690, and a line (e.g., a line 1680 as illustrated in FIG. 16C) connecting a radiation source and a detector of the medical imaging device cannot be adjusted to pass through the original POI, i.e., the central point 1660 of the heart of the target subject. As a result, a central beam emitted by the radiation source cannot pass through the central point 1660 of the heart. In such cases, the processing device 120 may determine a substitute POI to replace the original POI of the target subject. For example, a point 1670 that is on the line 1680 and has an identical height as the central point 1660 may be designated as the substitute POI of the target subject. Then, the subsequent scan on the target subject may be performed with respect to the substitute POI of the target subject. In some embodiments, a position of the C-arm, a position of the scanning table, and/or a position of the target subject relative to the scanning table may be adjusted such that the line connecting the radiation source and the detector of the medical imaging device can pass through the central point 1660. In such cases, the central point 1660 may still be determined as the POI of the target subject.

In some embodiments, the scan region of the target subject may be manually selected by a user of the imaging system 100. For example, the processing device 120 may cause a terminal device to display the image data of the target subject, a subject model generated based on the image data, or a target image (e.g., the target image 800 as illustrated in FIG. 8) of the target subject. The user may select the scan region (e.g., by drawing an area corresponding to the scan region, by selecting a plurality of reference points corresponding to the scan region) on the displayed image data or the subject model via an input component of the terminal device (e.g., a mouse, a touch screen). Alternatively, the scan region may be automatically set by one or more components of the imaging system 100 according to, for example, an imaging protocol of the target subject.

In some embodiments, the processing device 120 may determine the second position of the POI based on feature information (e.g., a width, a length, a thickness) of the scan region of the target subject. As used herein, a width of the scan region refers to a length of the scan region (e.g., a length at the center of the scan region, a maximum length of the scan region) along a direction perpendicular to a sagittal plane of the target subject. A length of a scan region refers to a length of the scan region (e.g., a length at the center of the scan region, a maximum length of the scan region) along a direction perpendicular to a transverse plane of the target subject. The processing device 120 may determine the feature information of the scan region based on the image data according to an image analysis algorithm (e.g., an image segmentation algorithm, a feature point extraction algorithm). Additionally or alternatively, the processing device 120 may determine the feature information of the scan region by generating a subject model representing the target subject based on the image data. For example, the processing device 120 may generate the subject model based on the image data. More descriptions of the generation of the subject model may be found elsewhere in the present disclosure (e.g., FIG. 7 and descriptions thereof). The processing device 120 may then determine, from the subject model, a target region corresponding to a scan region of the target subject.

The target region corresponding to the scan region of the target subject may be determined from the subject model according to various approaches. For example, the processing device 120 may identify one or more feature points corresponding to the scan region of the target subject from the subject model. A feature point corresponding to the scan region may include a pixel or voxel in the subject model corresponding to a representative physical point of the scan region. Different scan regions of the target subject may have their corresponding representative physical or anatomical point(s). Merely by way of example, one or more representative physical points corresponding to the chest of the target subject may include the ninth thoracic vertebra (i.e., the spine T9), the eleventh thoracic vertebra (i.e., the spine T11), and the third lumbar vertebra (i.e., the spine L3). One or more representative physical points corresponding to the right leg of the target subject may include the right knee. Taking the chest of the target subject as an exemplary scan region, a first feature point corresponding to the spine T9, a second feature point corresponding to the spine T11, and a third feature point corresponding to the spine L3 may be identified from the subject model. The processing device 120 may further determine the target region of the subject model based on the one or more identified feature points. For example, the processing device 120 may determine a region in the subject model that encloses the one or more identified feature points as the target region.

The processing device 120 may further determine feature information of the scan region of the target subject based on the target region determined from the subject model. The processing device 120 may also obtain position information of a scanning table supporting the target subject. The position information of the scanning table may include a height of the scanning table, a coordinate of the scanning table in a coordinate system (e.g., the coordinate system 170), or the like. In some embodiments, the image data acquired in operation 1510 may be captured when the target subject lies on the scanning table and indicate a position of the target subject relative to the scanning table. The position information of the scanning table may be determined based on the image data. Alternatively, the position information of the scanning table may be obtained from a position encoder mounted on the scanning table. The processing device 120 may then determine the second position of the POI based on the position information of the scanning table and the feature information of the scan region of the target subject.

For illustration purposes, it is assumed that the position information of the scanning table includes an X-axis coordinate, a Y-axis coordinate, and a Z-axis coordinate of a point (e.g., a central point) of the surface of the scanning table where the target subject lies on in the coordinate system (e.g., the coordinate system 170). The processing device 120 may determine an X-axis coordinate and a Y-axis coordinate of the second position in the coordinate system 170 based on the position information of the scanning table. For example, the processing device 120 may determine the X-axis coordinate and the Y-axis coordinate of the central point of the surface of the scanning table as the X-axis coordinate and the Y-axis coordinate of the second position, respectively. As another example, the processing device 120 may determine a position of the POI relative to the central point of the surface of the scanning table, and determine the X-axis coordinate and the Y-axis coordinate of the second position based on the X-axis coordinate and the Y-axis coordinate of the central point of the surface of the scanning table, and the position of the POI relative to the central point of the surface of the scanning table.

The processing device 120 may determine a Z-axis coordinate of the second position in the coordinate system 170 based on the height of the scanning table and the thickness of the scan region. Merely by way of example, the processing device 120 may determine a sum of the Z-axis coordinate (i.e., the height) of the scanning table and a certain percentage (e.g., a half, $2/3$) of the thickness of the scan region as the Z-axis coordinate of the second position. The certain percentage may be determined according to a default setting of the imaging system 100, manually by a user, or by the processing device 120 according to, for example, the position of an ROI (e.g., a specific organ) within the target subject. For example, a cardiac scan may be performed on the target subject, and the scan region may be the chest of the target subject. The Z-axis coordinate of the second position may be a sum of the Z-axis coordinate of the scanning table and $2/3$ of the thickness of the chest of the target subject. As another example, if the scan region is the head of the target subject, the Z-axis coordinate of the second position may be a sum of the Z-axis coordinate of the scanning table and $1/2$ of the thickness of the head of the target subject.

In 1530, the processing device 120 (e.g., the analyzing module 520) may determine a rotation scheme of the medical imaging device during the scan based on the first position of the imaging isocenter and the second position of the POI of the target subject.

In some embodiments, a rotation scheme of the medical imaging device may be defined by, for example, a rotation center of the medical imaging device, whether the medical imaging device performs an isocentric rotation or a non-isocentric rotation, or the like. As used herein, an isocentric rotation refers to that a central axis of radiation beams (e.g., X-ray beams) emitted from a radiation source (e.g., the radiation source 115) of the medical imaging device passes through the imaging isocenter of the medical imaging device when the radiation source rotates around the target subject during the scan. That is, during the isocentric rotation, the rotation center of the medical imaging device may be coincident with the imaging isocenter of the medical imaging device. As used herein, a non-isocentric rotation refers to that a central axis of radiation beams (e.g., X-ray beams) emitted from the radiation source (e.g., the radiation source 115) does not pass through an imaging isocenter when the radiation source rotates around the target subject during the scan. That is, during the isocentric rotation, the rotation center of the medical imaging device may be not coincident with the imaging isocenter of the medical imaging device.

In some embodiments, the processing device 120 may determine whether the first position of the imaging isocenter is coincident with the second position of the POI of the target subject. For example, the processing device 120 may determine whether the coordinate of the first position is the same (or substantially same) as the coordinate of the second position. In response to determining that the first position is coincident with the second position (e.g., the coordinate of the first position is the same (or substantially same) as the coordinate of the second position), the processing device 120 may perform an isocentric rotation around the second position of the POI during the scan.

In response to determining that the first position is not coincident with the second position (e.g., the coordinate of the first position is different from the coordinate of the second position), the processing device 120 may cause the medical imaging device to adjust the imaging isocenter from the first position to the second position. For example, the processing device 120 may determine a target position of a supporting device (e.g., a C-arm) of the medical imaging device based on the second position. The processing device 120 may then cause the supporting device to move to its target position. When the supporting device is located at its target position, the imaging isocenter may be at the second position. The processing device 120 may further cause the medical imaging device to perform the isocentric rotation around the second position of the POI during the scan.

Alternatively, in response to determining that the first position is not coincident with the second position, the processing device 120 may cause the medical imaging device to adjust the POI from the second position to the first position. For example, the processing device 120 may determine a target position of the target subject based on the first position. The processing device 120 may then cause the scanning table to move the target subject to the target position of the target subject. When the target subject is located at its target position, the POI may be at the first position. The processing device 120 may further cause the medical imaging device to perform the isocentric rotation around the first position during the scan.

In some embodiments, in response to determining that the first position is not coincident with the second position (e.g., the coordinate of the first position is different from the coordinate of the second position), the processing device 120 may cause the medical imaging device to perform the non-isocentric rotation around the second position of the POI during the scan. For example, a flexible arm may be connected to the supporting device (e.g., a C-arm) to drive the supporting device to rotate around the second position of the POI during the scan.

In some embodiments, in response to determining that the first position is not coincident with the second position (e.g., the coordinate of the first position is different from the coordinate of the second position), the processing device 120 may determine whether a height of the first position is greater than a height of the second position. For example, the processing device 120 may determine whether the Z-axis coordinate of the first position is greater than the Z-axis coordinate of the second position. In response to determining that the height of the first position is greater than the height of the second position (e.g., the Z-axis coordinate of the first position is greater than the Z-axis coordinate of the second position), the processing device 120 may cause the medical imaging device to perform a non-isocentric rotation around the second position of the POI during the scan. In response to determining that the height of the first position is lower than the height of the second position (e.g., the Z-axis coordinate of the first position is smaller than the Z-axis coordinate of the second position), the processing device 120 may cause the medical imaging device to adjust the imaging isocenter from the first position to the second position. The processing device 120 may further cause the medical imaging device to perform the isocentric rotation around the second position of the POI during the scan. In other words, if the POI of the target subject is above the imaging isocenter of the medical imaging device, the medical imaging device may be caused to lift its imaging isocenter to match the POI and perform an isocentric rotation around the POI; if the POI of the target subject is below the imaging isocenter, the medical imaging device may be caused to perform a non-isocentric rotation around the POI instead of moving the imaging isocenter of the medical imaging device. When the POI of the target subject is below the imaging isocenter, it may be close to the ground. If the medical imaging device is caused to reduce the height of the imaging isocenter to match the POI, the supporting device of the medical imaging device may hit the ground. Adopting different rotation schemes according to the heights of the POI and the imaging isocenter may avoid a collision between the supporting component of the medical imaging device and the ground.

According to some embodiments of the present disclosure, the rotation scheme of the medical imaging device may be determined based on the first position of the imaging isocenter of the medical imaging device and the second position of the POI of the target subject. The second position the POI of the target subject may be determined according to the image data of the target subject. For example, in the determination of the second position of the POI, feature information (e.g., the thickness, the width, and/or the length) of the scan region of the target subject may be determined based on the image data and taken into consideration. Conventionally, a user may need to manually determine and/or check the rotation scheme of a medical imaging device, for example, by visually inspecting whether the position of the imaging isocenter is coincident with the position of the POI of the target subject, and/or whether component(s) of the medical imaging device or the target subject needs to be moved. Compared to the conventional way, the systems and methods for determining the rotation scheme of the medical imaging device disclosed herein may be fully or partially automated, more accurate and efficient by, e.g., reducing the workload of a user, cross-user variations, and the time needed for the system setting.

FIG. 16A is a schematic diagram illustrating an exemplary process for determining a rotation scheme of a medical imaging device according to some embodiments of the present disclosure. As illustrated in FIG. 16A, in 1610, a target subject 1603 placed on a scanning table 1604 has a POI located at a position A. The height of the scanning table 1604 may be determined based on feature information (e.g., a height) of an operator 1601A and feature information (e.g., a thickness) of the target subject 1603. For example, the height of the scanning table 1604 may be determined by performing the process 1400 as described in connection with FIG. 14. A medical imaging device used to scan the target subject 1603 has a C-arm 1602, a radiation source (not shown in FIG. 16A), and a detector (not shown in FIG. 16A). The imaging isocenter of the medical imaging device is located at a position B. The height of the position A is greater than the height of the position B.

In 1620, the processing device 120 may cause the medical imaging device to adjust the imaging isocenter from the position B to the position A. For example, the processing device 120 may adjust the imaging isocenter by adjusting a position (e.g., increasing a height) of the C-arm 1602 of the medical imaging device. In 1630, the processing device 120 may cause the medical imaging device to perform an isocentric rotation around the position A of the POI during a first scan of the target subject 1603.

FIG. 16B is a schematic diagram illustrating an exemplary process for determining a rotation scheme of a medical imaging device according to some embodiments of the present disclosure. As illustrated in FIG. 16B, in 1640, the target subject 1603 placed on the scanning table 1604 has a POI located at a position C. The height of the scanning table 1604 may be determined based on feature information (e.g., a height) of an operator 1601B and feature information (e.g., a thickness) of the target subject 1603. For example, the height of the scanning table 1604 may be determined by performing the process 1400 as described in connection with FIG. 14. A medical imaging device used to scan the target subject 1603 has a C-arm 1602, a radiation source (not shown in FIG. 16B), and a detector (not shown in FIG. 16B). The height of the operator 1601A illustrated in FIG. 16A is higher than the height of the operator 1601B, and thus height of the scanning table 1604 illustrated in FIG. 16B is lower than the height of the scanning table 1604 illustrated in FIG. 16A. The imaging isocenter of a medical imaging device is located at a position D. The height of the position C is lower than the height of the position D. In 1650, the processing device 120 may cause the medical imaging device 1602 to perform a non-isocentric rotation around the position C of the POI during a second scan of the target subject 1603.

In some embodiments, after the first scan is performed on the target subject 1603 by the operator 1601A using the medical imaging device as described in FIG. 16A, the second scan may be performed on the target subject 1603 by the operator 1601B using the medical imaging device as described in FIG. 16B. The height of the operator 1601A is higher than the height of the operator 1601B, and accordingly the height of the scanning table 1604 may need to be adjusted (e.g., decreased) so that it is convenient for the operator 1601B to perform an operation (e.g., a surgery operation) on the target subject 1603. After the height of the scanning table 1604 is decreased based on the height of the operator 1601B, the position C of the POI of the target subject 1603 may be close to the ground. The medical imaging device may then be caused to perform the non-isocentric rotation around the position C of the POI instead of moving the imaging isocenter from the position D to the position C, in order to avoid a collision between the C-arm 1602 of the medical imaging device and the ground.

FIG. 17 is a flowchart illustrating an exemplary process for scan preparation according to some embodiments of the present disclosure.

In some embodiments, process 1700 may be performed before a scan to be performed on a target subject by a medical imaging device. In some embodiments, process 1700 may be performed after process 700, process 900, and/or process 1400. In some embodiments, one or more operations of process 1500 may be performed after process 1400 as described in connection with FIG. 14, in which a scanning table of the medical imaging device is automatically adjusted according to feature information (e.g., the width, the thickness) of the target subject and feature information (e.g., the height) of an operator of the medical imaging device.

In 1710, the processing device 120 (e.g., the acquisition module 510) may obtain image data of a target subject to be scanned by a medical imaging device. The image data may be acquired by at least one image capturing device.

Operation 1710 may be performed in a similar manner as operation 1510 as described in connection with FIG. 15, and the descriptions thereof are not repeated here.

In some embodiments, the medical imaging device may have an imaging isocenter. The position of the imaging isocenter may be determined based on a position of a component (e.g., a C-shape gantry) of the medical imaging device in the coordinate system (e.g., a coordinate of the component of the medical imaging device in the coordinate system 170) and a position of the imaging isocenter relative to the component of the medical imaging device. In some embodiments, the position of the imaging isocenter may be previously determined, for example, when the medical imaging device is mounted, and stored in a storage device (e.g., the storage device 130) of the imaging system 100. In some embodiments, the position of the imaging isocenter may be represented by a coordinate in a coordinate system, such as a first coordinate in the coordinate system 170 as shown in FIG. 1.

In 1720, the processing device 120 (e.g., the analyzing module 520) may determine, based on the image data, a scan region of the target subject.

In some embodiments, the determination of the scan region may be performed without user intervention. For example, the processing device 120 may automatically determine the scan region according to an imaging protocol of the target subject. Alternatively, the determination of the scan region may be performed semi-automatically by the processing device 120 with user intervention. For example, a user may provide information, and the processing device 120 may determine the scan region according to the information provided by the user. Exemplary information provided by the user may include a position parameter relating to a scan region, an adjustment to, or rejection or confirmation of a preliminary scan region generated by the processing device 120, etc. Alternatively, the determination of the scan region may be performed manually by a user.

In some embodiments, the processing device 120 may generate at least one display image of the target subject based on the image data of the target subject. For example, the display image may be the image data of the target subject obtained in operation 1710. As another example, the processing device 120 may generate a subject model (e.g., a 3D subject model) representing the target subject based on the image data. More descriptions for generating the subject model based on the image data may be found elsewhere in the present disclosure (e.g., FIG. 6 and descriptions thereof). The processing device 120 may further generate the at least one display image of the target subject based on the subject model. As still another example, the processing device 120 may generate a reference subject model representing an internal structure of the target subject by combining reference image data and the subject model. The reference image data may represent an internal structure of the target subject. The processing device 120 may further generate the at least one display image of the target subject based on the reference subject model. More descriptions for generating the reference subject model may be found elsewhere in the present disclosure (e.g., FIG. 21 and descriptions thereof).

Figure 18A:
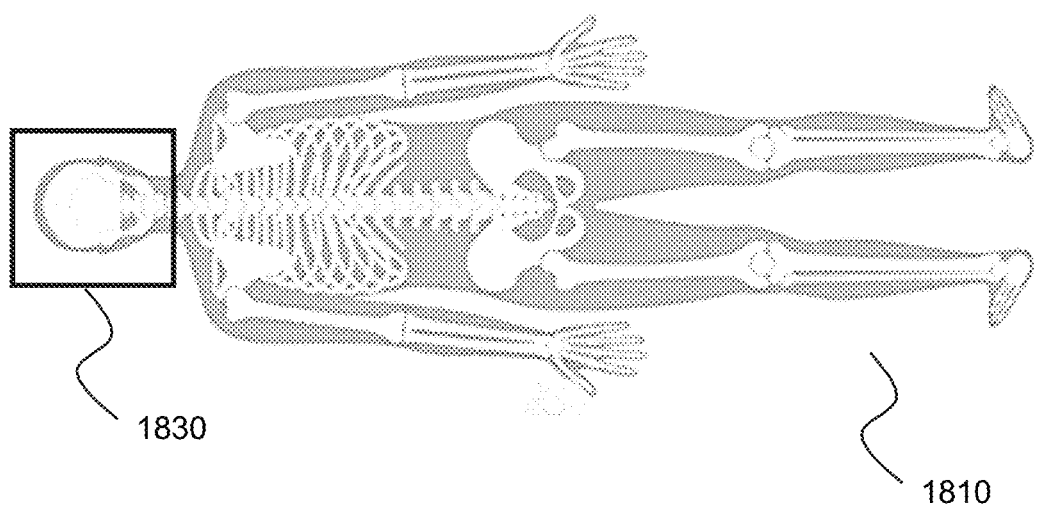
FIG. 18A illustrates an exemplary first image 1800A corresponding to a coronal plane of a patient extracted from a reference subject model of the patient.
Figure 18B:
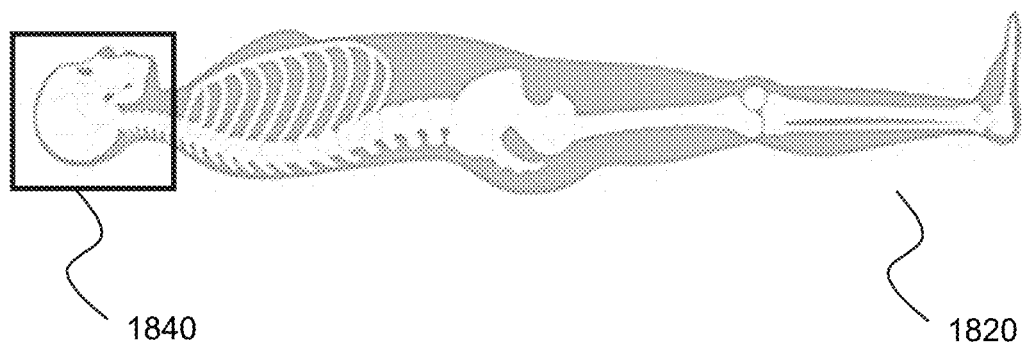
FIG. 18B illustrates an exemplary second image 1800B corresponding to a sagittal plane of a patient extracted from the reference subject model of the patient.

In some embodiments, the at least one display image may include a plurality of images corresponding to a plurality of views of the target subject generated based on one or more of the image data, the subject model, and the reference subject model of the target subject. For example, the processing device 120 may generate a first image corresponding to a coronal plane of the target subject and a second image corresponding to a sagittal plane of the target subject based on one or more of the image data, the subject model, and the reference subject model of the target subject. Merely by way of example, the reference subject model may be a 3D model, and the processing device 120 may extract the first image and the second image of the target subject from the reference subject model. For illustration purposes, FIG. 18A illustrates an exemplary first image 1800A corresponding to a coronal plane of a patient extracted from a reference subject model of the patient, and FIG. 18B illustrates an exemplary second image 1800B corresponding to a sagittal plane of a patient extracted from the reference subject model of the patient. By generating the plurality of display images, a plurality of views of the target subject, and the internal structure of the target subject may be presented to the user of the imaging system 100, and accordingly, the user may select the scan region of the target subject based on the plurality of display images easily.

In some embodiments, the processing device 120 may determine a plurality of regions of the target subject. Different regions of the plurality of regions may correspond to different positioning procedures of the target subject. Merely by way of example, the target subject is supported on a scanning table of the medical imaging device to receive a scan. The plurality of regions may include a first region that can be imaged by the medical imaging device without moving the scanning table, a second region that can be imaged by the medical imaging device by moving (e.g., translating, rotating) the scanning table, a third region that cannot be imaged by the medical imaging device, or the like, or any combination thereof. For example, the processing device 120 may determine a position of the target subject relative to the one or more components of the medical imaging device based on the image data. The processing device 120 may obtain position information relating to the one or more components of the medical imaging device. The processing device 120 may determine the plurality of regions of the target subject based on the position of the target subject relative to the one or more components and the position information relating to the one or more components. More descriptions for determining the plurality of regions may be found elsewhere in the present disclosure (e.g., FIGS. 7 and 8 and descriptions thereof). In some embodiments, for each of the at least one display image, the processing device 120 may generate the display image with a plurality of annotations of the plurality of regions. For example, the plurality of annotations of the plurality of regions may be displayed in the display image in different forms, such as different colors or different textures. By displaying the plurality of annotations of the plurality of regions in different colors or different textures, the user may distinguish the plurality of regions of the target subject easily, which may improve the user experience.

The processing device 120 may then cause a terminal device to display the at least one display image. The processing device 120 may further receive, via the terminal device, a selection of the scan region of the target subject. Merely by way of example, the terminal device may display the first image (e.g., the first image 1800A as illustrated in FIG. 18A) and the second image (e.g., the second image 1800B as illustrated in FIG. 18B). The user may select the scan region by drawing an area (e.g., a first region 1830 as illustrated in FIG. 18A and/or a second region 1840 as illustrated in FIG. 18B) corresponding to the scan region and/or selecting a plurality of reference points corresponding to the scan region on the first image and/or the second image, via an input component of the terminal device (e.g., a mouse, a touch screen). In some embodiments, the user may only need to select the scan region by annotating one of the first image and the second image. For example, if the user selects a region corresponding to a specific organ (e.g., the head) of the target subject on the first image, an annotation may be automatically added to the second image to annotate a region of the second image corresponding to the specific organ.

In 1730, the processing device 120 (e.g., the control module 530) may adjusting one or more components of the medical imaging device such that the scan region is targeted by the imaging isocenter of the medical imaging device. As used herein, a scan region may be regarded as being targeted by an imaging isocenter of the medical imaging device if a specific point (e.g., a POI) of the scan region is coincident with the imaging isocenter of the medical imaging device.

In some embodiments, the processing device 120 may determine the position of the POI by generating a subject model based on the image data of the target subject. More descriptions of the generation of the subject model may be found elsewhere in the present disclosure (e.g., FIG. 6 and descriptions thereof). The processing device 120 may then determine, from the subject model, a target region corresponding to the scan region of the target subject. The processing device 120 may further determine the position of the POI based on the target region. More descriptions for determining the position of the POI of the target subject may be found elsewhere in the present disclosure (e.g., operation 1520 in FIG. 15, and descriptions thereof). In some embodiments, the position of the POI may be represented by a coordinate in a coordinate system, such as a second coordinate in the coordinate system 170 as shown in FIG. 1.

After the position of the POI of the target subject is determined, the processing device 120 may determine a target position and/or moving parameter(s) of each of one or more components of the medical imaging device such that the imaging isocenter of the medical imaging device is coincident with the POI of the target subject. Merely by way of example, the processing device 120 may determine a position deviation between the position of the POI and the position of the imaging isocenter. The deviation may be represented by, for example, a difference between the first and second coordinates in the coordinate system 170. If the target subject lies on a scanning table of the medical imaging device, the processing device 120 may determine one or more moving parameters of the scanning table based on the position deviation to move the POI of the target subject to the position of the imaging isocenter. Alternatively, the processing device 120 may determine one or more moving parameters of a gantry of the medical imaging device based on the position deviation to move the imaging isocenter to the position of the POI. Alternatively, both of the scanning table and the gantry of the medical imaging device may be moved so that the POI of the target subject and the imaging isocenter may move to a same position.

In some embodiments, as described in connection with operation 1720, the processing device 120 may determine a plurality of regions of the target subject corresponding to different positioning procedures. For example, the plurality of regions may include the first region that can be imaged by the medical imaging device without moving the scanning table, the second region that can be imaged by the medical imaging device by moving (e.g., translating, rotating) the scanning table, the third region that cannot be imaged by the medical imaging device, or the like, or any combination thereof. If the scan region is within the first region, the scanning table may not need to be moved. For example, the processing device 120 may determine a target position of a supporting device based on the scan region, the image data, and the position information of the one or more components of the medical imaging device. The supporting device may support a radiation source and a detector of the medical imaging device, and the imaging isocenter may move when the supporting device moves. When the supporting device is at its target position, the scan region of the target subject can be targeted by the imaging isocenter of the medical imaging device. The processing device 120 may then cause the supporting device to move to the target position of the supporting device. The processing device 120 may further cause the medical imaging device to scan the target subject when the supporting device is at the target position of the supporting device.

If the scan region is within the second region, the scanning table may need to be moved. For example, the processing device 120 may determine a target position of the target subject based on the scan region, the image data, and the position information of the one or more components of the medical imaging device. When the target subject is located at its target position, the scan region of the target subject can be imaged by the medical imaging device (e.g., the scan region may be moved into a detection region of the medical imaging device). The processing device 120 may cause the scanning table to move the target subject to the target position of the target subject. The processing device 120 may also determine a target position of the supporting device based on the target position of the target subject, the scan region, the image data, and the position information of the one or more components of the medical imaging device. When the supporting device is at its target position, the scan region can be targeted by the imaging isocenter of the medical imaging device. The processing device 120 may cause the supporting device to move to the target position of the supporting device. The processing device 120 may further cause the medical imaging device to scan the target subject when the supporting device is at the target position of the supporting device.

If the scan region is within the third region, the processing device 120 may generate a notification. The notification may indicate that the scan region cannot be imaged by the medical imaging device. The notification may be in the form of text, voice, an image, a video, a haptic alert, or the like, or any combination thereof. For example, the processing device 120 may transmit the notification to a terminal device (e.g., the terminal device 140) of a user (e.g., a doctor) of the imaging system 100. The terminal device may output the notification to the user. Optionally, the user may adjust the position of the target subject and/or the medical imaging device in response to the notification. Merely by way of example, the user may guide the target subject to change his/her position relative to the scanning table.

According to some embodiments of the present disclosure, position(s) of component(s) of the medical imaging device may be adjusted based on a position of the scan region of the target subject, such that the scan region is targeted by the imaging isocenter of the medical imaging device. In addition, one or more display images of the target subject generated based on the image data of the target subject may be displayed to a user of the imaging system 100 to guide the user to select the scan region of the target subject. Conventionally, a user may need to move a radiation source of the medical imaging device to a position above the target subject to image the target subject. A scanning table supporting the target subject may be moved such that the scan region is targeted by the imaging isocenter of the medical imaging device in an X-Y plane as illustrated in FIG. 1. The user may then rotate the radiation source by 90 degrees so that the radiation source is turned to a left side or a right side of the target subject, to image the target subject. The height of the scanning table may be adjusted such that the scan region is targeted by the imaging isocenter of the medical imaging device along a Z-axis direction as illustrated in FIG. 1. Compared to the conventional way, the systems and methods disclosed herein may be fully or partially automated, more accurate and efficient by, e.g., reducing unnecessary radiation to a target subject and a user, the workload of a user, cross-user variations, and the time needed for the system setting.

Figure 19:
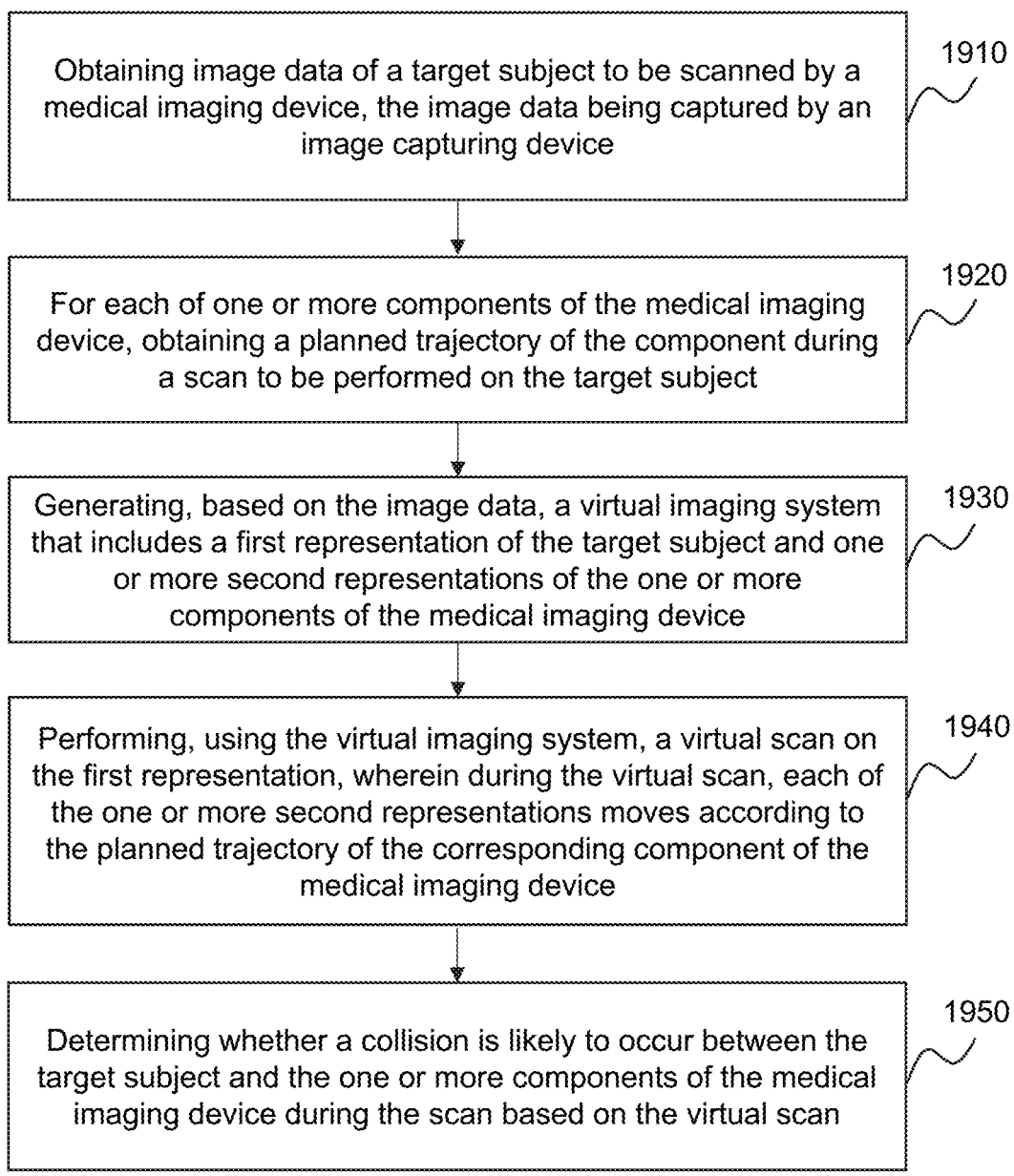
FIG. 19 is a flowchart illustrating an exemplary process for scan preparation according to some embodiments of the present disclosure.

FIG. 19 is a flowchart illustrating an exemplary process for scan preparation according to some embodiments of the present disclosure. In some embodiments, process 1900 may be performed before a scan to be performed on a target subject by a medical imaging device. In some embodiments, one or more operations of the process 1900 may be performed after process 700, process 900, process 1400, process 1500, and/or the process 1700.

In 1910, the processing device 120 (e.g., the acquisition module 510) may obtain image data of a target subject (e.g., a patient) to be scanned by a medical imaging device.

Operation 1910 may be performed in a similar manner as operation 610 as described in connection with FIG. 6, and the descriptions thereof are not repeated here.

In 1920, for each of one or more components of the medical imaging device, the processing device 120 (e.g., the acquisition module 510) may obtain a planned trajectory of the component during the scan to be performed on the target subject.

The one or more components of the medical imaging device may include one or more component(s) of the medical imaging device which can move during the scan to be performed on the target subject. For example, the one or more components may include a gantry (e.g., the gantry 111), a radiation source (e.g., the radiation source 115), a detector (e.g., the detector 112), etc. of the medical imaging device.

The planned trajectory of a component may be defined by one or more parameters, such as a position, a moving velocity, a moving direction of the component at each of a plurality of time points during the scan, a moving distance of the component during a time interval, or the like. In some embodiments, the planned trajectory of the component may be stored in a storage device (e.g., the storage device 130, the storage device 220, the storage 390, or an external source). The processing device 120 may retrieve the planned trajectory of the component from the storage device. Alternatively, the processing device 120 may determine the planned trajectory based on an imaging protocol of the target subject.

In 1930, the processing device 120 (e.g., the analyzing module 520) may generate, based on the image data, a virtual imaging system that includes a first representation of the target subject and one or more second representations of the one or more components of the medical imaging device.

Figure 20:
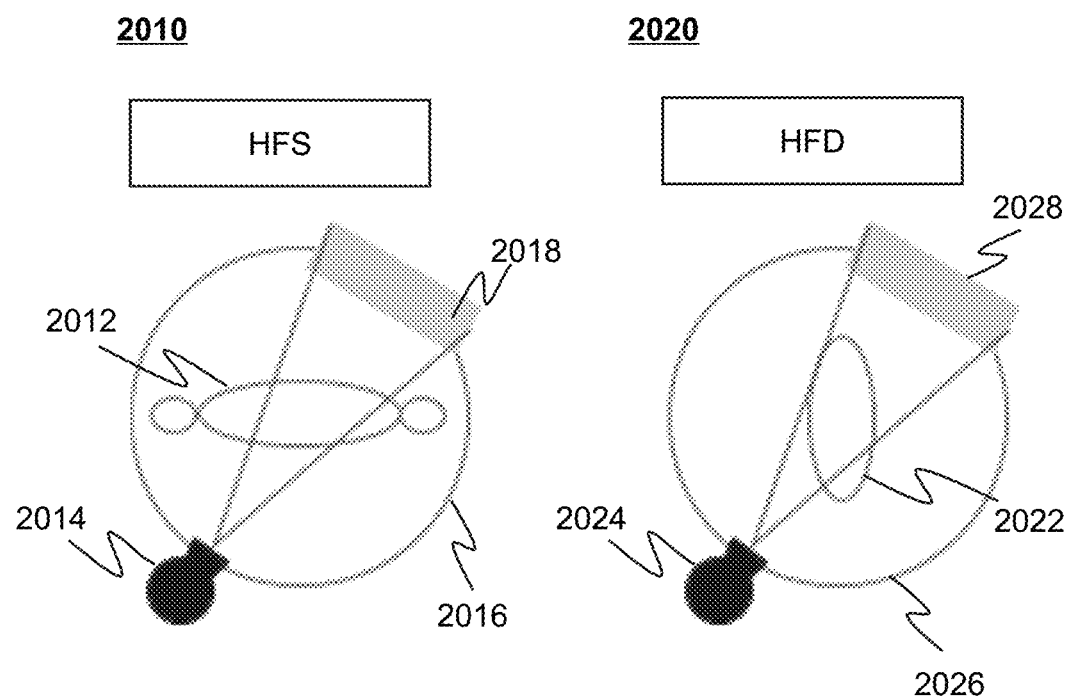
FIG. 20 is a schematic diagram illustrating exemplary virtual imaging systems according to some embodiments of the present disclosure.

The first representation of the target subject may indicate feature information (e.g., a height, a width, a thickness, a shape, a size, a position, a pose) of the target subject. For example, the first representation may be a virtual model or an image of the target subject. In some embodiments, the processing device 120 may generate the first representation based on the image data. For example, the processing device 120 may segment a portion corresponding to the target subject from the image data, and designate the segmented portion as the first representation. As another example, the processing device 120 may determine the feature information of the target subject based on the image data according to an image analysis algorithm (e.g., an image segmentation algorithm, a feature point extraction algorithm). The processing device 120 may further generate the first representation based on the feature information of the target subject. Merely by way of example, the position of the first representation in the virtual imaging system may be determined based on the position of the target subject. Additionally or alternatively, the shape and/or size of the first representation may be determined based on the shape and/or size of the target subject. Additionally or alternatively, the first representation may be determined based on the posture of the target subject. If the target subject holds a head first-supine (HFS) posture, a first representation 2012 as shown in FIG. 20, which indicates the body and two hands of the target subject, may be generated. If the target subject holds a head first-decubitus (HFD) posture, a first representation 2022 as shown in FIG. 20, which indicates the body of the target subject, may be generated.

In some embodiments, the processing device 120 may generate the first representation by generating a subject model representing the target subject based on the image data. The processing device 120 may further generate the first representation based on the subject model. Merely by way of example, the processing device 120 may designate the subject model as the first representation. As another example, the processing device 120 may determine the feature information of the target subject based on the subject model, and generate the first representation based on the feature information.

The second representation of a component of the medical imaging device may indicate feature information (e.g., a shape, a size, a position) of the component. For example, the second representation may be an image of the component. In some embodiments, the processing device 120 may obtain feature information of a component of the medical imaging device. Exemplary feature information of the component may include a shape, a size, a position of the component before the scan starts (e.g., a position of the component relative to the target subject before the scan starts), or the like, or any combination thereof. The feature information (or a portion thereof) of the component, such as the shape and/or size of a radiation source, may be stored in a storage device, and the processing device 120 may obtain the feature information (or a portion thereof) from the storage device. Additionally or alternatively, the feature information (or a portion thereof) of the component may be determined by the processing device 120. For example, the processing device 120 may determine the position of the component before the scan starts based on the image data (e.g., by identifying the component in the image data). As another example, the processing device 120 may determine the position of the component based on information received from a position encoder of the component. Further, the processing device 120 may generate the one or more second representations based on the feature information of the component. Merely by way of example, the position of the second representation of the component in the virtual imaging system may be determined based on the position of the component. Additionally or alternatively, the shape and/or size of the second representation of the component may be determined based on the shape and/or size of the component.

The virtual imaging system may be a simulated system that can visualize and simulate the scan to be performed on the target subject. In some embodiments, the processing device 120 may generate the virtual imaging system based on the first representation and the one or more second representations. The first representation may have a fixed position in the virtual imaging system. The second representation(s) may be movable in the virtual imaging system. In some embodiments, a preset virtual imaging system corresponding to the medical imaging device may be stored in a storage device (e.g., the storage device 130, the storage device 220, the storage 390, or an external source). The preset virtual imaging system may include a first preset representation and second preset representation(s) of the component(s) of the medical imaging device. For example, the processing device 120 may update the first preset representation in the preset virtual imaging system based on image data of the target subject and feature information of the component(s). The updated preset virtual imaging system with the updated first preset representation (i.e., the first representation) and the updated second preset representation(s) (i.e., the second representation(s)) may be designated as the virtual imaging system. As another example, only the first preset representation may be updated, and the second preset representations of the component(s) may be directly used as the second representation(s).

In 1940, the processing device 120 (e.g., the control module 640) may perform, using the virtual imaging system, a virtual scan on the first representation.

The virtual scan may be used to perform a collision detection before an actual scan is performed on the target subject by the medical imaging device. The virtual scan on the first representation may simulate the actual scan to be performed on the target subject. During the virtual scan, each of the one or more second representations may move according to the planned trajectory of the corresponding component of the medical imaging device. In some embodiments, the processing device 120 may cause a terminal device (e.g., the terminal device 140) to display the virtual imaging system and the virtual scan performed using the virtual imaging system.

In 1950, the processing device 120 (e.g., the analyzing module 520) may determine whether a collision is likely to occur between the target subject and the one or more components of the medical imaging device during the scan based on the virtual scan.

In some embodiments, for a component of the medical imaging device, the processing device 120 may determine a distance between the second representation of the component and the first representation of the target subject during the virtual scan. The processing device 120 may further determine whether a collision is likely to occur between the target subject and the component based on the distance. For example, the processing device 120 may determine whether the distance is less than a threshold (e.g., 1 mm, 5 mm, 1 cm). The threshold may be manually set by a user of the imaging system 100 or determined by one or more components (e.g., the processing device 120) of the imaging system 100. In response to determining that the distance is less than the threshold, the processing device 120 may determine that a collision is likely to occur between the target subject and the component during the scan. In response to determining that the distance is greater than the threshold, the processing device 120 may determine that no collision is likely to occur between the target subject and the component during the scan. In some embodiments, the second representation may move to different positions according to the planned trajectory of the component of the medical imaging device corresponding to the second representation. A plurality of distances between the first representation of the target subject and the second representation at different positions may be determined. The processing device 120 may determine whether a collision is likely to occur between the target subject and the component based on each of the plurality of distances.

In some embodiments, in response to determining that a collision is not likely to occur between the target subject and the one or more components of the medical imaging device, the processing device 120 may cause the medical imaging device to perform the scan on the target subject. In response to determining that a collision is likely to occur between the target subject and the component(s) during the scan, the processing device 120 may generate a notification. The notification may indicate the possible collision. The processing device 120 may further cause the terminal device to output the notification regarding the collision to a user (e.g., an operator or a doctor) of the imaging system 100. Optionally, the user may adjust the position(s) of the target subject and/or the component(s) of the medical imaging device based on the likely occurred collision.

In some embodiments, after the position(s) of the target subject and/or the component(s) of the medical imaging device are adjusted, the processing device 120 may then obtain image data of the target subject to determine updated position information of the target subject, and/or updated planned trajectory (trajectories) of the component(s) based on updated position information of the component(s) of the medical imaging device. The processing device 120 may further determine whether a collision is likely to occur between the target subject and the one or more components of the medical imaging device based on the updated position information of the target subject and/or the updated planned trajectory (trajectories) of the component(s) of the medical imaging device. In some embodiments, the iteration of 1910 (or 1920) to 1950 may be repeated until a collision is not likely to occur between the target subject and the one or more components of the medical imaging device.

According to some embodiments of the present disclosure, a virtual imaging system may be generated based on the image data of the target subject and the planned trajectory (trajectories) of the component(s) of the medical imaging device, and a virtual scan may be performed using the virtual imaging system to determine whether a collision is likely to occur between the target subject and the component(s) of the medical imaging device during the scan. In addition, the virtual scan may be displayed to a user of the imaging system 100. Conventionally, the component(s) of the medical imaging device needs to actually move along their planned trajectory (trajectories) to simulate the scan of the target subject, which is time-consuming. Compared to the conventional way, the systems and methods for virtual collision detection disclosed herein may be fully or partially automated, more accurate and efficient by, e.g., reducing the workload of a user and the time needed for the collision detection.

In some embodiments, one or more operations may be added or omitted. For example, a process for storing the virtual imaging system in the storage device may be added after operation 1930. The processing device 120 may retrieve the virtual imaging system from the storage device for scan preparation of subsequent subjects to be scanned. As another example, operation 1930 and operation 1940 may be omitted. After the planned trajectory of each component of the one or more components of the medical imaging device is obtained as described in connection with operation 1920, the processing device 120 may perform the virtual scan on the target subject based on the image data and the planned trajectories of the one or more components of the medical imaging device. For example, the processing device 120 may perform the virtual scan based on the image data of the target subject and the planned trajectory of the each component of the one or more components, and further determine whether a collision is likely to occur between the target subject and the component based on the virtual scan. Merely by way of example, the processing device 120 may perform the virtual scan by estimating a distance between the target subject and each component during the scan, and determine whether a collision is likely to occur based on the distance.

In some embodiments, two or more operations may be performed simultaneously. For example, operation 1910 and operation 1920 may be performed simultaneously.

FIG. 20 is a schematic diagram illustrating exemplary virtual imaging systems according to some embodiments of the present disclosure. As shown in FIG. 20, a virtual imaging system 2010 includes a first representation 2012 of a target subject with a posture of HFS, a second representation 2014 of a radiation source of a medical imaging device, and a second representation 2018 of a detector of the medical imaging device. The virtual imaging system 2010 may be used to perform a first virtual scan on the first representation 2012 for scan preparation. During the first virtual scan, the second representation 2014 and the second representation 2018 may be moved according to a planned trajectory 2016 of the radiation source and the detector. A virtual imaging system 2020 includes a first representation 2022 of a target subject with a posture of HFD, a second representation 2024 of a radiation source of a medical imaging device, and a second representation 2028 of a detector of the medical imaging device. The virtual imaging system 2020 may be used to perform a second virtual scan on the first representation 2022 for scan preparation. During the second virtual scan, the second representation 2024 and the second representation 2028 may be moved according to a planned trajectory 2026 of the radiation source and the detector.

Figure 21:
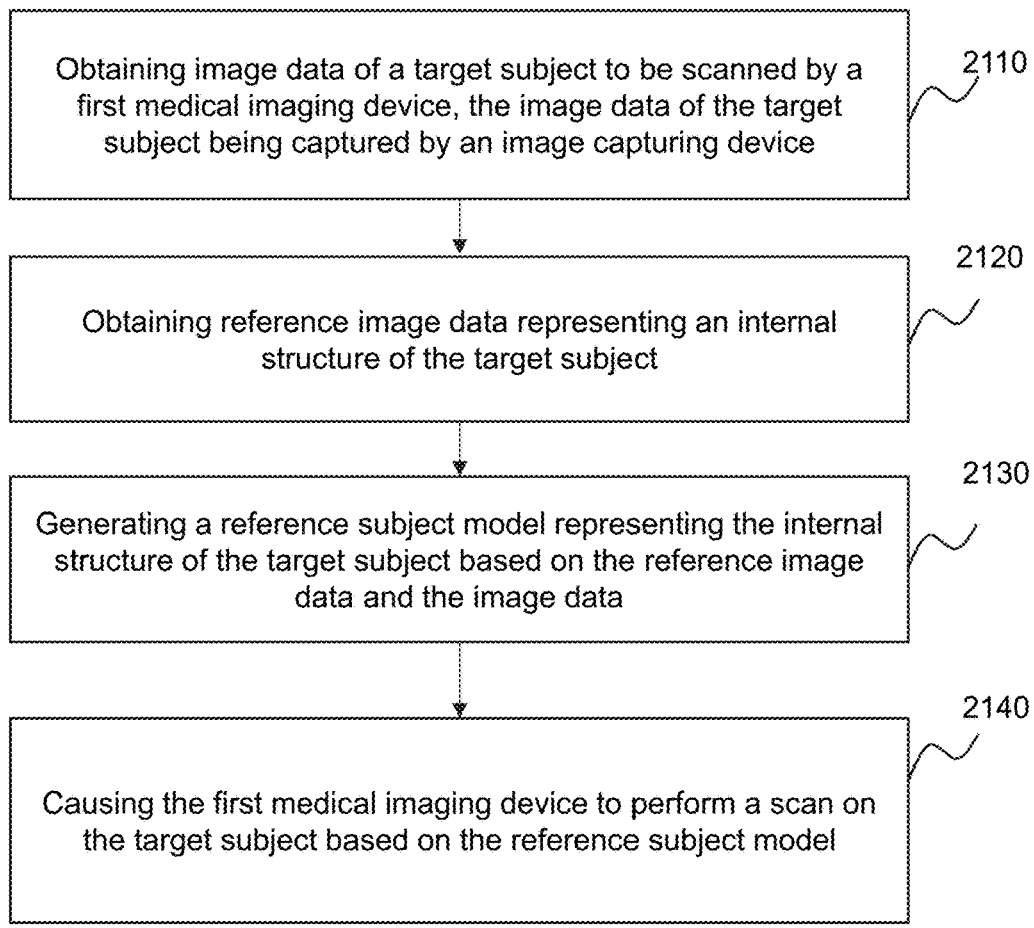
FIG. 21 is a flowchart illustrating an exemplary process for medical imaging according to some embodiments of the present disclosure.

FIG. 21 is a flowchart illustrating an exemplary process for medical imaging according to some embodiments of the present disclosure.

In some embodiments, one or more operations (e.g., operations 2110-2130) of the process 2100 may be implemented for scan preparation before a scan is performed on a target subject (e.g., a patient or a portion thereof). For example, operation(s) of the process 2100 may be performed for adjusting positions of one or more components of a first medical imaging device. The scan of the target subject may be performed by the first medical imaging device. As another example, operation(s) of the process 2100 may be performed for determining whether a collision is likely to occur between the target subject and component(s) of the first medical imaging device. As still another example, operation(s) of the process 2100 may be performed for positioning the target subject.

In 2110, the processing device 120 (e.g., the acquisition module 510) may obtain image data of the target subject to be scanned by the first medical imaging device.

Operation 2110 may be performed in a similar manner as operation 610 as described in connection with FIG. 6, and the descriptions thereof are not repeated here.

In 2120, the processing device 120 (e.g., the acquisition module 510) may obtain reference image data representing an internal structure (e.g., organs and/or tissues) of the target subject.

Operation 2120 may be performed in a similar manner as operation 920 as described in connection with FIG. 9, and the descriptions thereof are not repeated here.

In 2130, the processing device 120 (e.g., the analyzing module 520) may generate, based on the reference image data and the image data, a reference subject model representing the internal structure of the target subject.

Figure 23:
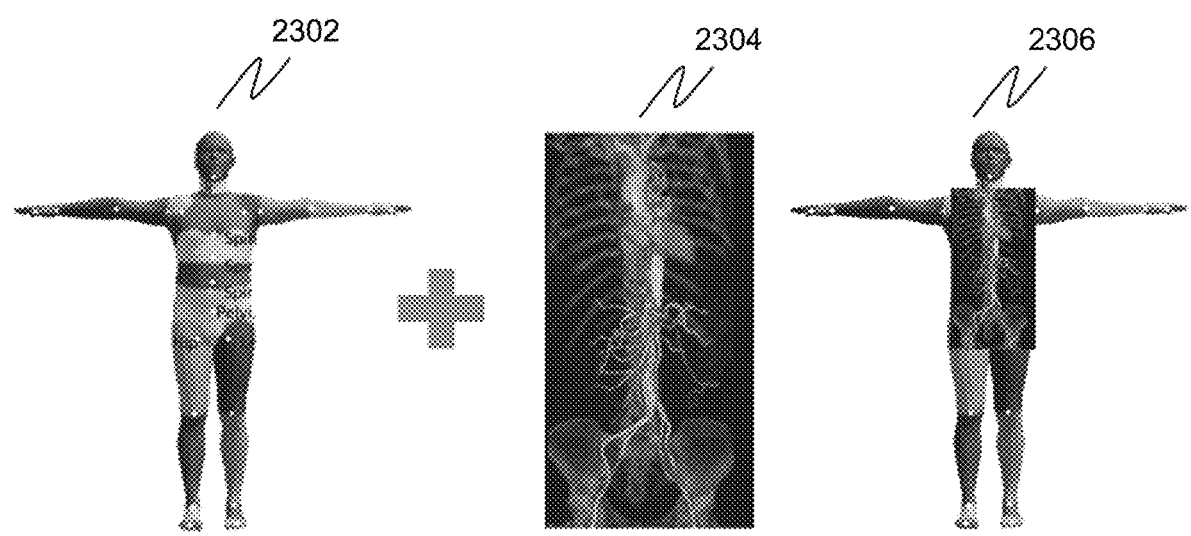
FIG. 23 illustrates a schematic diagram of an exemplary process for generating a reference subject model according to some embodiments of the present disclosure.

The reference subject model of the target subject (e.g., a reference subject model 2306 as illustrated in FIG. 23) may indicate both the appearance (e.g., the contour and the posture) and the internal structure of the target subject.

In some embodiments, the processing device 120 may generate a subject model of the target subject based on the image data of the target subject. The subject model (e.g., a subject model 2302 as illustrated in FIG. 23) may represent an appearance of the target subject holding the posture when the image data is captured. The subject model may include a 2D skeleton model, a 3D skeleton model, a 3D mesh model, or the like. Further, the processing device 120 may generate the reference subject model of the target subject based on the subject model and the reference image data (e.g., by combining the subject model and the reference image data). The type of the generated reference subject model may be the same as or different from that of the subject model. For example, the subject model may be a 3D mesh model indicating the appearance of the target subject, and the reference subject model may be a 3D mesh model representing the internal structure of the target subject. More descriptions regarding the generation of the subject model and the reference subject model may be found elsewhere in the present disclosure (e.g., FIG. 22 and the description thereof).

For illustration purposes, FIG. 23 illustrates a schematic diagram of an exemplary process for generating a reference subject model according to some embodiments of the present disclosure. As shown in FIG. 23, the subject model 2302 was generated based on image data of a patient. Reference image data 2304, which is a historical anatomical image of a portion of the patient, was acquired. The reference subject model 2306 was generated by combining the subject model 2302 and the reference image data 2304. The reference subject model 2306 may represent not only an appearance (e.g., the shape, the size, or the posture) of the patient but also an internal structure of the portion of the patient.

In 2140, the processing device 120 (e.g., the control module 640) may cause the first medical imaging device to perform a scan on the target subject based on the reference subject model.

In some embodiments, the processing device 120 may identify, in the reference subject model, a region corresponding to a scan region of the target subject to be scanned by the first medical imaging device. For example, the scan region of the target subject may include the chest, the abdomen, the vertebral, the elbow, an organ (e.g., the head, the heat, etc.), a tissue (e.g., blood vessels), or the like, or any combination thereof, of the target subject. The region corresponding to the scan region may be determined manually by a user. For example, the processing device 120 may cause a terminal device (e.g., the terminal device 140) to display the reference subject model. The region corresponding to the scan region may be annotated by the user via the terminal device, for example, by drawing the region corresponding to the scan region on the displayed reference subject model. Alternatively, the region corresponding to the scan region may be determined by the processing device 120 by analyzing the internal structure of the target subject based on the reference subject model. Merely by way of example, the processing device 120 may determine the scan region according to the imaging protocol of the target subject, and segment the region corresponding to the scan region from the reference subject model according to an image segmentation algorithm. Alternatively, the region corresponding to the scan region may be determined by the processing device 120 semi-automatically based on an image segmentation algorithm and information provided by the user.

The processing device 120 may then adjust one or more components (e.g., a C-arm) of the first medical imaging device such that the scan region is targeted by an imaging isocenter of the first medical imaging device. Further, the processing device 120 may cause the first medical imaging device to scan the scan region of the target subject. More descriptions regarding the adjustment of positions of the component(s) based on the reference subject model may be found elsewhere in the present disclosure (e.g., FIGS. 15 and 17 and relevant descriptions thereof).

In some embodiments, before the scan of the scan region, the processing device 120 may obtain one or more parameter values of one or more scan parameters of the first medical imaging device relating to the scan to be performed on the target subject. The processing device 120 may generate a target image Ti' representing an internal structure of the scan region of the target subject to be scanned by the first medical imaging device under the one or more parameter values based on the reference subject model and the one or more parameter values. Optionally, the target image Ti' may be transmitted to a terminal device for display. A user may confirm whether the scan region needs to be adjusted according to the target image Ti'. More descriptions regarding the generation of the target image Ti' based on the reference subject model may be found elsewhere in the present disclosure (e.g., FIGS. 9-13 and relevant descriptions thereof).

According to some embodiments of the present disclosure, a reference subject model of a target subject may be generated based on image data of the target subject and reference image data that represents an internal structure of the target subject. The reference subject model may represent both an appearance (e.g., the posture, the shape, the size) of the target subject and an internal structure of the target subject. In some embodiments, the reference subject model may be displayed to a user for selecting a scan region of the target subject. Additionally or alternatively, a target image Ti' representing an internal structure of the scan region may be generated based on the reference subject model and displayed to the user. The user may check the scan region of the target subject according to the target image Ti'. Optionally, after the scan region is selected and/or checked, one or more components of the medical imaging device may be adjusted to prepare for the scan of the target subject. Traditionally, the scan region may be determined based on an image of the target subject merely indicating an appearance of the target subject, or the user may need to manually move the target subject and/or one or more components of the medical imaging device to prepare for the scan, which is inaccurate (e.g., susceptible to human errors or subjectivity) and inefficient (e.g., time-consuming).

Figure 22:
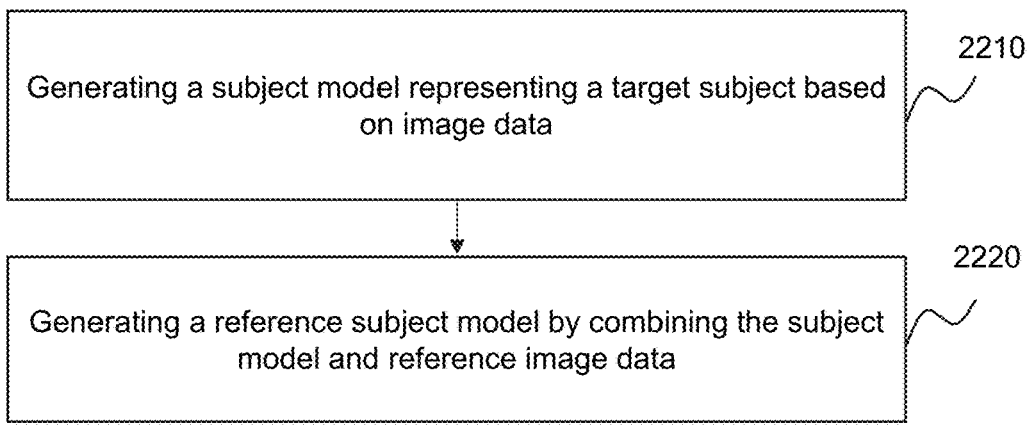
FIG. 22 is a flowchart illustrating an exemplary process for generating a reference subject model according to some embodiments of the present disclosure.

In some embodiments, operation 2130 of the process 2100 may be achieved by performing one or more operations of process 2200 as shown in FIG. 22.

In 2210, the processing device 120 (e.g., the analyzing module 520) may generate a subject model representing the target subject based on the image data. More descriptions regarding the generation of a subject model may be found elsewhere in the present disclosure. See, e.g., operation 660 in FIG. 6 and relevant descriptions thereof.

The processing device 120 (e.g., the analyzing module 520) may generate the reference subject model by combining the subject model and the reference image data.

In some embodiments, the processing device 120 may combine the subject model and the reference image data by performing one or more image processing operations, such as a fusion operation, an image registration operation, or the like, or any combination thereof. The fusion operation may include a data-level (or pixel-level) image fusion operation, a feature-level image fusion operation, a decision-level image fusion operation, or the like, or any combination thereof. The fusion operation may be performed according to, for example, a maximum density projection algorithm, a multiscale analysis algorithm, a wavelet transform algorithm, etc. In some embodiments, before the fusion operation, the processing device 120 may register the reference image data with the subject model. The registered reference image data may be represented in the same coordinate system as the subject model. The processing device 120 may further generate the reference subject model by fusing the registered reference image data and the subject model.

In some embodiments, the processing device 120 may identify, in the subject model, one or more first regions each of which corresponds to one of one or more ROIs of the target subject. The ROI(s) of the target subject may include one or more representative body portions, such as an anatomical joint (e.g., a shoulder joint, a knee joint, an elbow joint, an ankle joint, a wrist joint), the head, the neck, a hand, a leg, a foot, a spine, a pelvis, a hip, or the like, or any combination thereof, of the target subject. The processing device 120 may identify, in the reference image data, one or more second regions each of which corresponds to one of the one or more ROIs of the target subject. In some embodiments, the reference image data may include a reference anatomical image of a reference subject, and the identified second region(s) may correspond to the one or more ROIs of the reference subject. For example, a first region may correspond to the head of the target subject, and a second region may correspond to the head of the reference subject. Because the reference subject has a similar internal structure to the target subject, the internal structure within the second region of the reference subject may be regarded as an equivalent of the internal structure of the first region of the target subject.

Further, the processing device 120 may generate the reference subject model based on the one or more first regions and the one or more second regions. For instance, for each ROI of the target subject, the processing device 120 may align the second region corresponding to the ROI with the first region corresponding to the ROI. Optionally, the processing device 120 may adjust the shape and/or size of the second region corresponding to the ROI so that the adjusted second region may have a substantially same shape and/or size as the first region corresponding to the ROI.

In some embodiments, the processing device 120 may determine, based on the subject model, one or more first values of one or more contour parameters of the target subject. Exemplary contour parameters of the target subject may include a shape and/or a size (e.g., a height, a width, a thickness) of the target subject or a portion of the target subject. Merely by way of example, the contour parameter(s) of the target subject may include a shoulder-width, a chest circumference, a waistline, a length of a limb, etc. of the target subject. The processing device 120 may determine, based on the reference image data, one or more second values of the one or more contour parameters of the target subject. In some embodiments, the reference image data may include a reference anatomical image of a reference subject, and value(s) of the contour parameter(s) of the reference subject may be determined and designated as the second value(s) of the contour parameter(s) of the target subject. For example, a first value of the height of the target subject may be determined based on the subject model, and a height of the reference subject may be determined based on the reference image data. Because the reference subject has a similar internal structure to the target subject, the height of the reference subject may be designated as a second value of the height of the target subject. Further, the processing device 120 may generate the reference subject model based on the one or more first values and the one or more second values of the one or more contour parameters. For instance, the processing device 120 may align the reference image data with the subject model based on the first value(s) and the second value(s) of the contour parameter(s). If the first value(s) is equal to the second value(s), the processing device 120 may directly overlap the reference image data with the subject model. If the first value(s) is different from the second value(s), the processing device 120 may first adjust the reference image data (e.g., zoom in or out the reference image data) and then overlap the adjusted reference image data and the subject model.

In some embodiments, one or more operations may be added or omitted. For example, the operation 2210 may be omitted, and the reference subject model may be generated by combining the original image data and the reference image data. As another example, the operation 2140 may be omitted. In some embodiments, two or more operations may be performed simultaneously. For example, operation 2110 and operation 2120 may be performed simultaneously.

Figure 24A:
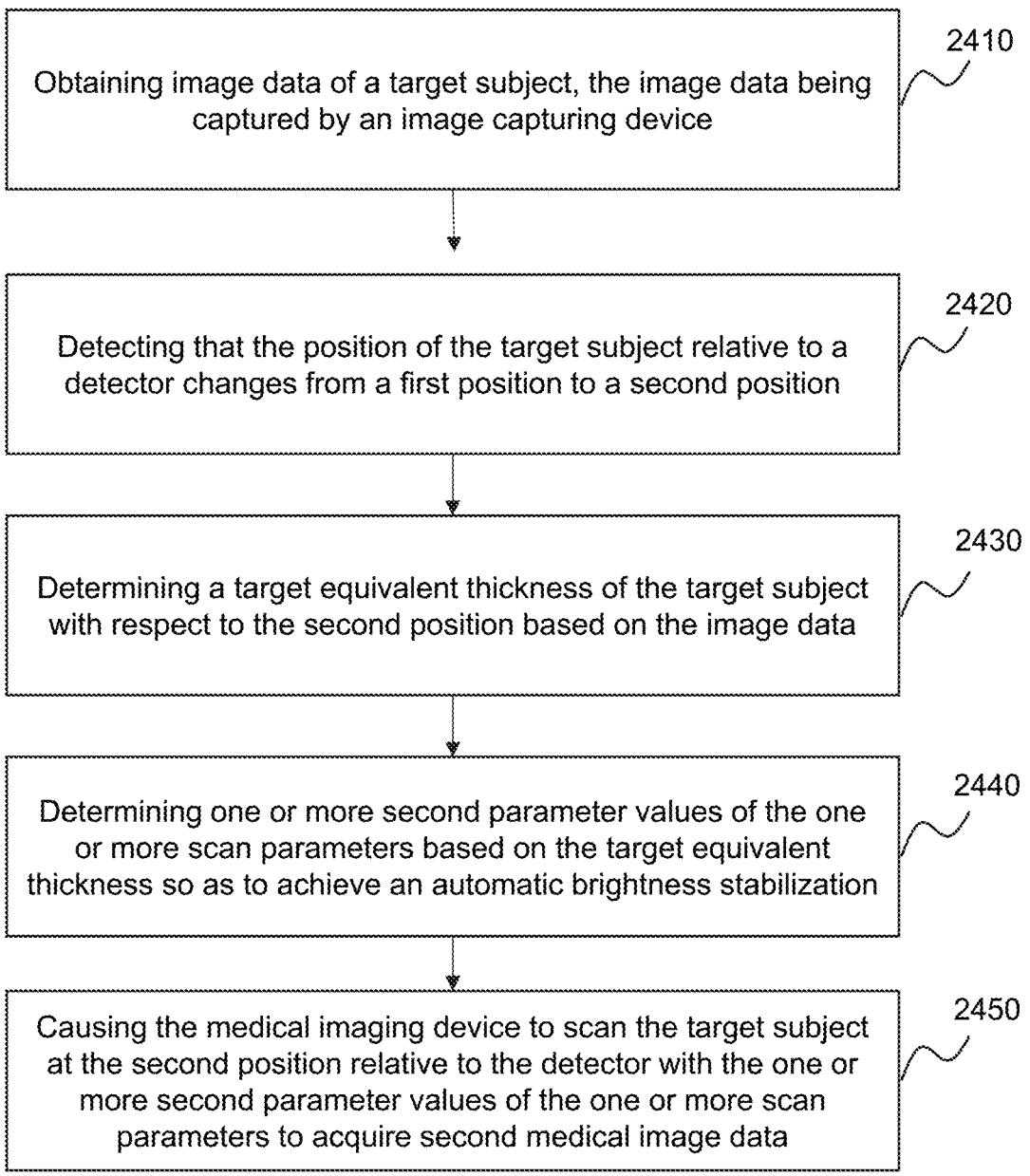
FIG. 24A is a flowchart illustrating an exemplary process for achieving automatic brightness stabilization (ABS) during a scan of a target subject performed by a medical imaging device according to some embodiments of the present disclosure.

FIG. 24A is a flowchart illustrating an exemplary process for achieving automatic brightness stabilization (ABS) during a scan of a target subject performed by a medical imaging device according to some embodiments of the present disclosure.

In some embodiments, the medical imaging device may acquire a plurality of sets of medical image data during the scan of the target subject. For example, the medical imaging device may rotate one or more components thereof (e.g., a radiation source, a detector, etc.) to acquire a plurality of sets of medical image data that correspond to different views of the target subject. As another example, a scanning table (e.g., the scanning table 114) may be moved to acquire a plurality of sets of medical image data that correspond to different scan regions of the target subject. Process 2400 may be used to automatically stabilize the brightness of the sets of medical image data acquired during the scan of the target subject.

For example, if the brightness of the sets of medical image data are the same or substantially the same, the brightness stabilization may be achieved. As used herein, two values may be regarded as being substantially the same as each other if a difference between the two values is below a threshold, such a constant value or a certain percentage (e.g., 1%, 2%, 5%, 10%, etc.) of one of the two values. As another example, if the brightness of the sets of medical image data are both within a specific range, the brightness stabilization may be achieved. As another example, if the brightness of each set of medical image data is close to a desired brightness corresponding to the set of medical image data, the brightness stabilization may be achieved. The desired brightness of a set of medical image data may be associated with the scan region corresponding to the set of medical image data. Merely by way of example, the desired brightness of a set of medical image data corresponding to the abdomen of the target subject may be different from the desired brightness of a set of medical image data corresponding to the feet of the target subject because the thicknesses of the abdomen and the feet may be different. The desired brightness corresponding to a scan region may be determined according to a default setting of the imaging system 100, or manually set by a user (e.g., an operator), or determined by the processing device 120 according to an actual need. For example, the desired brightness corresponding to a scan region may be determined based on feature information (e.g., an attenuation coefficient, a position, an equivalent thickness, or a density) of the scan region.

The brightness of a set of medical image data may be measured by, for example, a maximum brightness, a minimum brightness, an average brightness, or the like, of the set of medical image data. For example, the brightness of a set of medical image data may be determined by averaging the brightness of the pixels (or voxels) of the set of medical image data.

In 2410, the processing device 120 (e.g., the acquisition module 510) may obtain image data of the target subject.

The image data of the target subject may be captured by an image capturing device (e.g., the image capturing device 160) before or during the scan of the target subject. For example, the image capturing device may automatically capture the image data of the target subject when or after the target subject enters an examination room. As another example, the image capturing device may capture the image data of the target subject when the target subject lies on a scanning table (e.g., the scanning table 114) before or during the scan. In some embodiments, the obtaining of the image data of the target subject may be performed in a similar manner as that described in connection with operation 610.

In some embodiments, the target subject may be scanned at a first position relative to a detector of the medical imaging device with one or more first parameter values of one or more scan parameters. The scan parameter(s) may include, for example, a voltage of a radiation source, a current of the radiation source, a distance between the radiation source and a detector (also referred to as a source image distance, or a SID), a radiation dose, a size of a focal spot, a filtration of radiation rays, an exposure time of the scan, a size of a light field, a detector aperture, a field of view (FOV), or the like, or any combination thereof. In some embodiments, the first parameter value(s) of the scan parameter(s) may be set by a user (e.g., a doctor, an operator) manually or determined by the processing device 120 (or another computing device) according to an actual need.

In some embodiments, first medical image data may be acquired by the medical imaging device when the target subject is located at the first position relative to the detector. The first position and/or the first parameter value(s) of the scan parameter(s) may affect the quality of the first medical image data. Merely by way of example, the first position and/or the first parameter value(s) of the scan parameter(s) may be associated with the brightness (or referred to as the grey level) of the first medical image data. For example, the greater the radiation dose, the greater the brightness of the first medical image data is. As another example, the greater the attenuation coefficient of a first scan region of the target subject corresponding to the first position relative to the detector, the lower the brightness of the first medical image data is.

In 2420, the processing device 120 (e.g., the analyzing module 520) may detect that a position of the target subject relative to the detector changes from the first position to a second position.

In some embodiments, the position of the target subject relative to the detector may change when the scanning table moves, for example, along a horizontal direction (e.g., the X-axis and/or Y-axis direction of the coordinate system 170 as shown in FIG. 1), a vertical direction (e.g., the Z-axis direction of the coordinate system 170 as shown in FIG. 1), or the like, or any combination thereof. In some embodiments, the position of the target subject relative to the detector may change when the target subject target moves, for example, turns over.

In some embodiments, the position of the target subject relative to the detector may change when a scanning angle of the medical imaging device changes during the scan of the target subject. For example, a gantry (e.g., the gantry 111) of the medical imaging device may rotate to change the scanning angle of the medical imaging device so as to acquire medical image data of the target subject corresponding to different scanning angles. As another example, a user may manually adjust the position of a radiation source and/or a detector of the medical imaging device to change the scanning angle.

In some embodiments, the processing device 120 may detect a change of the position of the target subject relative to the detector by various approaches. For example, the change of the scanning angle may be detected based on an imaging protocol that defines a value and/or a change of the value of the scanning angle during the scan of the target subject. As another example, an angle detector mounted on the gantry may measure the scanning angle of the medical imaging device continuously or intermittently (e.g., periodically). The processing device 120 may detect the change of the scanning angle of the medical imaging device based on a measurement result of the angle detector. As another example, the processing device 120 may determine that the position of the target subject relative to the detector changes when an instruction for changing the position of the scanning table is received from a user terminal (e.g., the terminal(s) 140). In some embodiments, a second image capturing device (e.g., the image capturing device 160) may be configured to capture second image data associated with the medical imaging device during the scan in real time or intermittently (e.g., periodically). The processing device 120 may detect the change of the position of the target subject relative to the detector based on the second image data, for example, by detecting a change of a position of a radiation source of the medical imaging device, a motion of the target subject, a change of a position of the scanning table, or the like, or any combination thereof. The second image capturing device may be the same as or different from the image capturing device as described in connection with operation 2410.

Figure 24B:
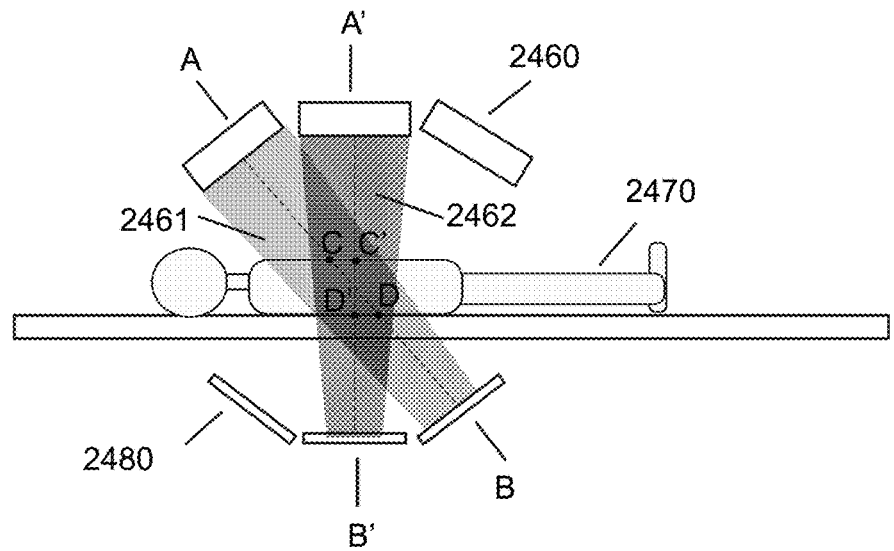
FIG. 24B illustrates a schematic diagram of different scanning angles of a medical imaging device according to some embodiments of the present disclosure.

In some embodiments, the change in the position of the target subject relative to the detector may result in a change in a scan region of the target subject. For the purpose of illustration, the change of the scan region caused by the change of the scanning angle of the medical imaging device may be taken as an example. FIG. 24B illustrates a schematic diagram of different scanning angles of a medical imaging device according to some embodiments of the present disclosure. As shown in FIG. 24B, a patient 2470 lies on a scanning table, and the medical imaging device includes a radiation source 2460 and a detector 2480. When the radiation source 2460 is located at a position A and the detector 2480 is located at a position B, the medical imaging device may scan a first scan region of the patient 2470 at a first angle. The first scan region may be a region of the patient 2470 passed by first radiation rays 2461 that are emitted by the radiation source 2460 at the position A. When the radiation source 2460 moves from the position A to a position A' and the detector 2480 moves from the position B to a position B', the medical imaging device may scan a second scan region of the patient at a second angle. The second scan region may be a region of the patient 2470 passed by second radiation rays 2462 that are emitted by the radiation source 2460 at the position A'.

The characteristics (e.g., a thickness, a density, a position, an attenuation coefficient, or the like, or any combination thereof) of the first and second scan regions may be different. For example, the first scan region of the target subject may have a first equivalent thickness and the second scan region of the target subject may have a second equivalent thickness different from the first equivalent thickness. An equivalent thickness of a scan region may indicate a thickness of the scan region. For example, an equivalent thickness of a scan region may be measured by an estimated distance that a radiation ray for scanning the scan region may traverse within the target subject. Merely by way of example, as shown in FIG. 24B, the first equivalent thickness of the first scan region may be measured by a length of a first line connecting point C and point D, wherein the first line may represent a central axis of the first radiation rays 2461 emitted by the radiation source 2460 at the first scanning angle. The second equivalent thickness of the second scan region may be measured by a length of a second line connecting point C' and point D', wherein the second line may represent a central axis of the second radiation rays 2462 emitted by the radiation source 2460 at the second scanning angle. It should be understood that the example illustrated in FIG. 24B is merely provided for illustration purposes, and not to be limiting. For example, the first equivalent thickness of the first scan region may be measured by an average distance that a plurality of first radiation rays may traverse within the target subject.

The change in the position of the target subject relative to the detector may also result in a change in the quality of medical image data acquired by the medical imaging device if the value(s) of the scan parameter(s) remain unchanged. For example, if the position of the target subject relative to the detector changes from the first position to the second position while the value(s) of the scan parameter(s) remain unchanged, the brightness of the second medical image data may have a great difference (e.g., a difference greater than a brightness threshold) with respect to the brightness of the first medical image data because of the change in the scan region of the target subject. The brightness difference between the first medical image data and the second medical image data may cause a brightness instability of the medical image data acquired during the scan, which may further affect a processing of the medical image data and diagnosis performed based on the medical image data. In order to eliminate or reduce the effect of the change of the position relative to the detector and the brightness instability, the medical imaging device may need to perform the scan on the target subject with different parameter values of the scan parameter(s) if the position of the target subject relative to the detector changes during the scan.

Conventionally, if the position of the target subject relative to the detector changes, the parameter value(s) of the scan parameter(s) may be adjusted manually. For example, an operator of the medical imaging device may manually adjust the parameter value(s) of the scan parameter(s) according to the change of the position of the target subject relative to the detector, which may be inefficient and/or susceptible to human errors or subjectivity. Alternatively, after the position of the target subject relative to the detector changes from the first position to the second position, the medical imaging device may be caused to acquire additional medical image data at the second position. An operator or the processing device 120 may adjust the parameter value(s) of the scan parameter(s) based on the additional medical image data. For example, if an image frame has a higher brightness than a corresponding second brightness threshold, the voltage and/or the current of the radiation source may be reduced. Normally, several image frames (e.g., 3-5 image frames) may need to be acquired and the adjustment of the parameter value(s) of the scan parameter(s) may be performed based on the several image frames until an automatic brightness stabilization is achieved. This may increase the radiation dose received by the target subject during the scan and cause a longer scanning time.

According to some embodiments of the present disclosure, the second parameter value(s) of the scan parameter(s) may be determined based on the image data of the target subject without acquiring additional medical image data of the target subject. In addition, the systems and methods disclosed herein for achieving automatic brightness stabilization may be implemented with reduced or minimal or without user intervention. Compared with conventional ways, the systems and methods disclosed herein for achieving automatic brightness stabilization are more efficient and accurate by, e.g., reducing the radiation dose received by the target subject, reducing the workload of a user, cross-user variations, and the time needed for the scan.

In 2430, the processing device 120 (e.g., the analyzing module 520) may determine a target equivalent thickness of the target subject with respect to the second position based on the image data.

As used herein, the target equivalent thickness (or referred to as a second equivalent thickness) may indicate a thickness of the second scan region of the target subject corresponding to the second position. For example, radiation rays may be emitted from a radiation source of the medical imaging device and irradiate the target subject during the scan of the target subject when the target subject is located at the second position relative to the detector. The target equivalent thickness may be measured by an estimated distance that the radiation rays may traverse within the target subject.

In some embodiments, the processing device 120 may determine the target equivalent thickness of the target subject with respect to the second position based on the image data acquired by the image capturing device. For example, the processing device 120 may determine an estimated trajectory of the radiation rays emitted by the radiation source corresponding to the second position, and determine the target equivalent thickness based on the estimated trajectory of the radiation rays. As another example, the processing device 120 may generate a subject model representing the target subject based on the image data, and determine the target equivalent thickness based on the subject model. The generation of a subject model may be performed in a similar manner as that described in connection with operation 660. After the subject model is generated, the processing device 120 may determine the target equivalent thickness based on the subject model in a similar manner as how the target equivalent thickness is determined based on the original image data as aforementioned.

In 2440, the processing device 120 (e.g., the analyzing module 520) may determine the second parameter value(s) of the scan parameter(s) based on the target equivalent thickness.

In some embodiments, the processing device 120 may determine the second parameter value(s) of the scan parameter(s) such that an automatic brightness stabilization may be achieved. For example, the second parameter value(s) of the scan parameter(s) may be determined such that the second medical image data of the target subject corresponding to the position may have a same (or substantially same) brightness as the first medical image data of the target subject corresponding to the first position. The second medical image data may be regarded as having a same (or substantially same) brightness as the first medical image data if a brightness difference between the first medical image data and the second medical image data is less than a brightness threshold. In some embodiments, the brightness threshold may be determined according to a default setting of the imaging system 100, manually by a user, or adjusted by the processing device 120 according to different conditions (e.g., an environmental brightness). In this way, a brightness stabilization may be achieved.

As another example, the second parameter value(s) of the scan parameter(s) may be determined such that the brightness of the second medical image data may be equal to (or substantially equal to) a desired brightness corresponding to the second scan region when the target subject is located at the second position relative to the detector. The desired brightness may be determined according to a default setting of the imaging system 100, manually by a user, or adjusted by the processing device 120 according to different conditions.

In some embodiments, the processing device 120 may determine the second parameter value(s) of the scan parameter(s) based on the target equivalent thickness and feature information of the target subject. The feature information of the target subject may include an attenuation coefficient, a position, a density of the second scan region of the target subject, or the like, or any combination thereof. For example, if the first scan region of the target subject has a greater equivalent thickness than the second scan region, the processing device 120 may determine a smaller voltage of the radiation source and/or a smaller current of the radiation source for the second scan region, such that the brightness of the second medical image data may be the same (or substantially same) as that of the first medical image data. As another example, if the attenuation coefficient corresponding to the first scan region is greater than that corresponding to the second scan region, the processing device 120 may determine a smaller voltage of the radiation source and/or a smaller current of the radiation source for the second scan region, such that the brightness of the second medical image data is the same (or substantially same) as that of the first medical image data.

In some embodiments, the processing device 120 may determine the second parameter value(s) based on the target equivalent thickness using a scan parameter determination model. The scan parameter determination model refers to a model (e.g., a machine learning model) or an algorithm for determining parameter value(s) of the scan parameter(s) corresponding to an equivalent thickness. For example, the processing device 120 may input the target equivalent thickness into the scan parameter determination model, and the scan parameter determination model may output the second parameter value(s) of the scan parameter(s) by processing the target equivalent thickness. Optionally, the input of the scan parameter determination model may further include, for example, feature information (e.g., the attenuation coefficient, the position, the density, etc.) of the second scan region.

In some embodiments, the scan parameter determination model may be predetermined by a computing device (e.g., the processing device 120 or a computing device of a vendor of the scan parameter determination model) and stored in a storage device (e.g., the storage device 130, the storage device 220, the storage 390, or an external source). The processing device 120 may obtain the scan parameter determination model from the storage device.

Alternatively, the processing device 120 may obtain the scan parameter determination model by training a preliminary model using at least one training sample. Each of the at least one training sample may include a sample equivalent thickness of a sample subject and sample parameter value(s) of the scan parameter(s) corresponding to the sample equivalent thickness. In some embodiments, the preliminary model may be of any type of machine learning model. Merely by way of example, the preliminary model may include an artificial neural network (ANN), a random forest model, a support vector machine, a decision tree, a convolutional neural network (CNN), a Recurrent Neural Network (RNN), a deep learning model, a Bayesian network, a K-nearest neighbor (KNN) model, a generative adversarial network (GAN) model, etc. The training of the preliminary model may be implemented according to a machine learning algorithm, such as an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the scan parameter determination model may be a supervised learning algorithm, a semi-supervised learning algorithm, an unsupervised learning algorithm, or the like.

In some embodiments, an objective function (e.g., a loss function) may be used to evaluate how well the preliminary model is trained. According to the objective function, the processing device 120 may adjust the preliminary model until the objective function reaches a desired value or converges. After the objective function reached the desired value or converges, the adjusted preliminary model may be designated as the scan parameter determination model.

In some embodiments, the processing device 120 may determine the second parameter value(s) of the scan parameter(s) based on a relationship between an equivalent thickness and the scan parameter(s). For example, the relationship may be represented in the form of a table or curve recording different equivalent thicknesses and their corresponding value(s) of the scan parameter(s), a drawing, a mathematical expression, etc. The relationship between the equivalent thickness and the scan parameter(s) may be stored in a storage device, and the processing device 120 may retrieve the relationship from the storage device. Alternatively or additionally, the relationship between the equivalent thickness and the scan parameter(s) may be determined by the processing device 120 based on experimental data. In some embodiments, the relationship may be obtained or determined based on the second scan region. For example, if the second scan region is the chest of a patient, a relationship between an equivalent thickness of the human chest and the scan parameter(s) may be obtained or determined.

In some embodiments, the processing device 120 may determine the second parameter value(s) of the scan parameter(s) based on an ABS curve. The ABS curve may include a plurality of points each of which corresponds to a specific combination of the current of the radiation source and the voltage of the radiation source. The points of the ABS curve may correspond to a same brightness level. For example, the equivalent thickness of the second scan region (i.e., the target equivalent thickness) may greater than that of the first scan region. The processing device 120 may determine a point on the ABS curve that corresponds to a higher current of the radiation source and a higher voltage of the radiation source than a point corresponding to the first scan region. The current and the voltage of the radiation source corresponding to the determined point may be designated as the second parameter value(s) of the scan parameter(s).

In 2450, the processing device 120 (e.g., the control module 530) may cause the medical imaging device to scan the target subject at the second position with the second parameter value(s) of the scan parameter(s) to acquire the second medical image data.

In some embodiments, the processing device 120 may generate a control instruction to cause one or more components of the medical imaging device to scan the target subject. For example, the processing device 120 may cause the radiation source to emit radiation rays base on the second parameter value(s). As another example, the processing device 120 may cause the detector to detect radiation rays that pass through the target subject.

In some embodiments, one or more operations of the process 2400 may be omitted, and/or the process 2400 may include one or more additional operations. Merely by way of example, when the scan is performed when the target subject is at the first position, a target image Ti' representing an internal structure of the first scan region with respect to the first position may be generated according to one or more operations of the process 900 as described in connection with FIG. 9 and displayed on a terminal device. When the position of the target subject relative to the detector changes from the first position to the second position, another target image Ti' representing an internal structure of the second scan region corresponding to the second position may be generated according to one or more operations of the process 1100 as described in connection with FIG. 11 and displayed on the terminal device. An operator of the medical imaging device may check the position of one or more components of the medical imaging device based on the target image Ti' corresponding to the first position and/or the target image Ti' corresponding to the second position. As another example, one or more operations of process 2500 as described in connection with FIG. 25 may be added to monitor the posture of the target subject during the scan of the target subject. In some embodiments, operation 2450 may be omitted.

Figure 25:
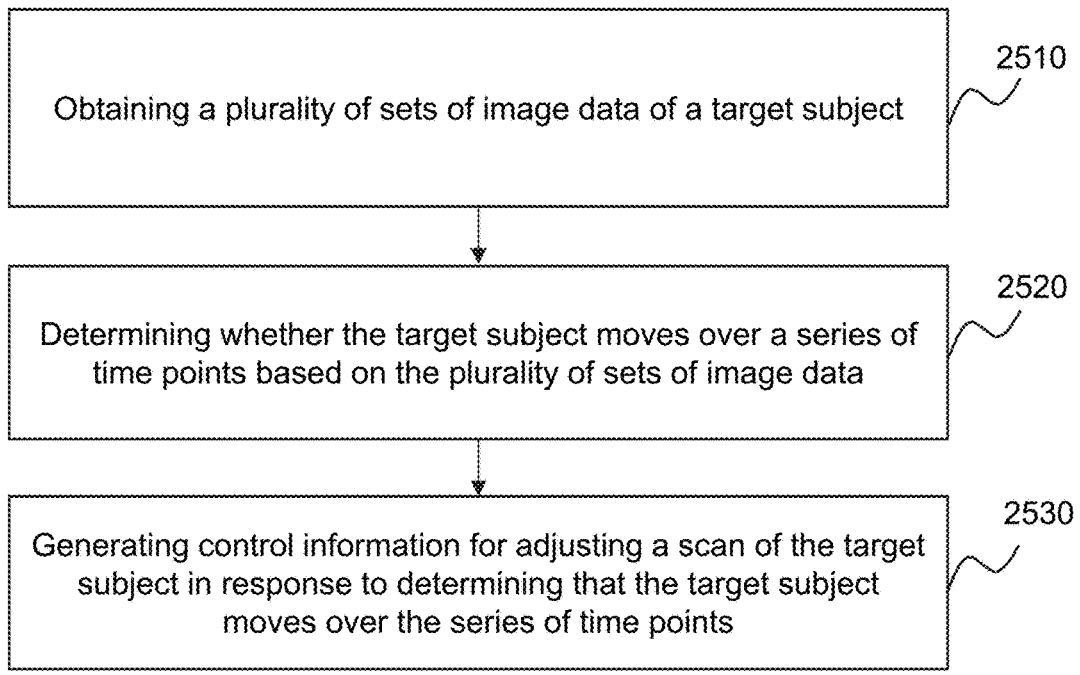
FIG. 25 is a flowchart illustrating an exemplary process for monitoring a target subject during a scan of the target subject according to some embodiments of the present disclosure.

FIG. 25 is a flowchart illustrating an exemplary process for monitoring a target subject during a scan of the target subject according to some embodiments of the present disclosure.

In some embodiments, the target subject may be scanned by a medical imaging device (e.g., the medical imaging device 110), and the process 2500 may be performed to monitor the target subject during the scan of the target subject. For example, the process 2500 may be performed to determine whether the target subject moves during the scan based on image data of the target subject captured by an image capturing device (e.g., the image capturing device 160). Conventionally, a user (e.g., an operator of the medical imaging device) may need to manually observe the target subject and determine whether the target subject remains in a still or substantially still state, which may be inefficient and susceptible to human error or subjectivity. The systems and methods for monitoring the target subject during the scan may be implemented without or with reduced or minimal user intervention, which is time-saving, more efficient, and more accurate (e.g., insusceptible to human error or subjectivity).

In 2510, the processing device 120 (e.g., the acquisition module 510) may obtain a plurality of sets of image data of the target subject.

The plurality of sets of image data may be captured by an image capturing device (e.g., the image capturing device 160) during the scan of the target subject at a series of time points (or referred to as a time series). Each of the plurality of sets of image data may correspond to one of the series of time points. The time interval between each pair of consecutive time points of the series of time points may be fixed or unfixed. For example, the image capturing device may be directed to capture a set of image data of the target subject (or a portion thereof) in every time unit (e.g., 0.1 seconds, 0.2 seconds, 0.3 seconds, etc.) during the scan of the target subject. The processing device 120 may obtain the plurality of sets of image data of the target subject from the image capturing device. Alternatively, the plurality of sets of image data may be captured by the image capturing device and stored in a storage device (e.g., a storage device of the imaging system, an external storage device, etc.). The processing device 120 may obtain the sets of image data from the storage device.

A set of image data captured by the image capturing device may include image data representing the entire or a portion of the target subject (e.g., an upper part, a lower part, or the chest of the target subject). The plurality of sets of image data may include an RGB image, a depth image, an IR image of the target subject, etc.

In 2520, the processing device 120 (e.g., the determination module 530) may determine whether the target subject moves over the series of time points based on the plurality of sets of image data.

As used herein, a motion of the target subject may be measured by one or more motion parameters, such as a moving distance, a moving direction, a moving trajectory, a change of a posture, or the like, or any combination thereof, of the target subject (or a portion thereof). A moving distance may include a pixel distance in the image domain and/or an actual distance in the physical space. A posture of the target subject may reflect one or more of a position, a pose, a shape, a size, etc., of the target subject (or a portion thereof).

In some embodiments, the processing device 120 may determine a motion of the target subject over the time series based on the plurality of sets of image data, and determine whether the target subject moves over the time series based on the determined motion. For example, the processing device 120 may determine whether the motion of the target subject exceeds a threshold T. If the motion of the target subject exceeds than the threshold T, the processing device 120 may determine that the target subject moves over the series of time points. If the motion of the target subject does not exceed the threshold T, the processing device 120 may determine that the target subject does not move. The threshold T may have a preset value or a value that can be dynamically adjusted by the processing device 120 according to different conditions.

The motion of the target subject over the series of time points may include a motion of the target subject from a first time point of the time series to a second time point after the first time point of the time series, wherein the first and second time points may be any two different time points of the time series. The first and second time points may be a pair of consecutive time points (i.e., there is no intermediate time point between the first and second time points) or a pair of inconsecutive time points (i.e., there are one or more intermediate time points between the first and second time points) among the time series. For example, it is assumed that the time series includes time points T1 to Tn, wherein n refers to any positive integer greater than 1. The motion of the target subject over the time series may include a motion of the target subject from T1 to Tn, which may be determined based on the set of image data captured at T1 and Tn. As another example, the motion of the target subject over the time series may include a motion of the target subject between each pair of consecutive time points of the time series, e.g., a motion from T1 to T2, a motion from T2 to T3, . . . , and a motion from T(n−1) to Tn. The motion of the target subject between a pair of consecutive time points may be determined based on the set of image data captured at the pair of consecutive time points.

In some embodiments, the processing device 120 may determine the motion of the target subject by tracking a motion of at least one body landmark of the target subject over the time series. The at least one body landmark may include one or more representative body regions of the target subject, such as one or more anatomical joints, a shoulder, an ankle, the waist, a knee, a groin, or the like, or any combination thereof. To determine the motion of the at least one body landmark over the time series, the processing device 120 may identify at least one feature point representing the at least one body landmark of the target subject from each of the plurality of sets of image data. For example, the one or more feature points may be annotated manually by a user (e.g., a doctor, an imaging specialist, a technician) on an interface (e.g., implemented on the terminal(s) 140) that displays a set of image data. Alternatively, the one or more feature points may be identified from a set of image data by the processing device 120 automatically according to an image analysis algorithm (e.g., an image segmentation algorithm, a feature point extraction algorithm). Alternatively, the one or more feature points may be identified from a set of image data by the processing device 120 semi-automatically based on an image analysis algorithm in combination with information provided by a user. In some embodiments, for each set of image data, the processing device 120 may generate a first subject model representing the target subject and identify the at least one feature point from the first subject model. More descriptions regarding the generation of a subject model based on a set of image data may be found elsewhere in the present disclosure. See, e.g., operation 660 and the relevant descriptions thereof.

Based on the feature point(s) identified in each set of image data or the first subject model corresponding to the set of image data, the processing device 120 may further determine the motion of the body landmark over the time series. Taking the left ankle as an exemplary body landmark, a first pixel representing the left ankle may be identified from an image corresponding to a first time point, and a second pixel representing the left ankle may be identified from an image corresponding to a second time point after the first time point. The processing device 120 may determine a pixel distance between the first and second pixels and designate the pixel distance or an actual distance corresponding to the pixel distance as the motion of the left ankle over the time series. The processing device 120 may further determine the motion of the target subject based on the motion of the body landmark of the target subject over the time series. For example, if there are a plurality of body landmarks, the processing device 120 may determine a maximum motion or an average motion of the body landmarks as the motion of the target subject.

In some embodiments, for each of the sets of image data, the processing device 120 may determine one or more parameter values of one or more posture parameters of the target subject based on the set of image data. Exemplary posture parameter(s) may include a position (e.g., a coordinate in a coordinate system) of a portion (e.g., the head, the neck, a hand, a leg, and/or a foot) of the target subject, a joint angle of a joint (e.g., a shoulder joint, a knee joint, an elbow joint, and/or an ankle joint) of the target subject, a shape and/or a size of a portion of the target subject, a height of the entire target subject or a portion (e.g., the upper body, the lower body) of the target subject, or the like, or any combination thereof. For a set of image data, the processing device 120 may determine the parameter value(s) of the posture parameter(s) based on the original set of image data or a second subject model generated based on the set of image data. The second subject model may include a 2D skeleton model, a 3D skeleton model, a 3D mesh model, etc., which may be the same as or different from the first subject model as mentioned above.

The processing device 120 may further determine the motion of the target subject over the time series based on the parameter value(s) of the posture parameter(s) of the target subject corresponding to each of the sets of image data. Merely by way of example, the processing device 120 may determine a first parameter value of a posture parameter based on a first set of image data captured at a first time point of the time series, and a second parameter value of the posture parameter based on a second set of image data captured at a second time point of the time series. The processing device 120 may determine a parameter value change of the posture parameter based on the first and second parameter values as the motion of the target subject. As another example, if there are a plurality of posture parameters, the processing device 120 may determine a value change of each of the posture parameters, and determine the motion of the target subject by summing up or averaging the parameter value changes corresponding to the posture parameters.

In some embodiments, as aforementioned, after the motion of the target subject is determined, the processing device 120 may determine whether the target subject moves by comparing the motion with a threshold T. In some embodiments, the motion of the target subject may be measured by various parameters, such as a motion of a body landmark, a parameter value change of a posture parameter, or the like, or any combination thereof. Each of the parameters may have a corresponding threshold value. For example, the motion of a body landmark may be compared with a threshold distance. As another example, the value change of a posture parameter may be compared with a threshold with respect to the posture parameter.

In 2530, the processing device 120 (e.g., the generation module 520) may generate control information for adjusting the scan of the target subject in response to determining that the target subject moves over the time series.

In some embodiments, in response to determining that the target subject moves over the time series, the processing device 120 may generate control information to adjust one or more components of the medical imaging device. For example, the processing device 120 may transmit an instruction to cause the medical imaging device to terminate the scan of the target subject (e.g., cause a radiation source of the medical imaging device to terminate emitting radiation rays). As another example, the target subject may lie on a scanning table of the medical imaging device, and the processing device 120 may move the target subject via moving the scanning table so as to compensate for the motion of the target subject. As yet another example, the processing device 120 may cause the radiation source and/or a detector of the medical imaging device to move their respective position(s) such that an ROI of the target subject can be targeted by an imaging isocenter of the medical imaging device after the target subject moves.

In some embodiments, the processing device 120 may generate the control information for adjusting the scan by causing a terminal device to generate a notification. The notification may indicate that the target subject moves. The notification may be in the form of, for example, a text message, a voice message, a graphic message, etc. An operator of the medical imaging device may adjust the posture of the target subject and/or the position(s) of one or more components of the medical imaging device according to the notification.

In some embodiments, in response to determining that the target subject moves over the time series, the processing device 120 may adjust value(s) of scan parameter(s) relating to the scan. Exemplary scan parameters may include a voltage of a radiation source, a current of the radiation source, a distance between the radiation source and a detector, a radiation dose, a scan time, or the like, or any combination thereof. For illustration purposes, if the processing device 120 determines that the target subject places the hands on two sides of the target subject's body, the processing device 120 may increase the value(s) of the scan parameter(s).

Figure 26:
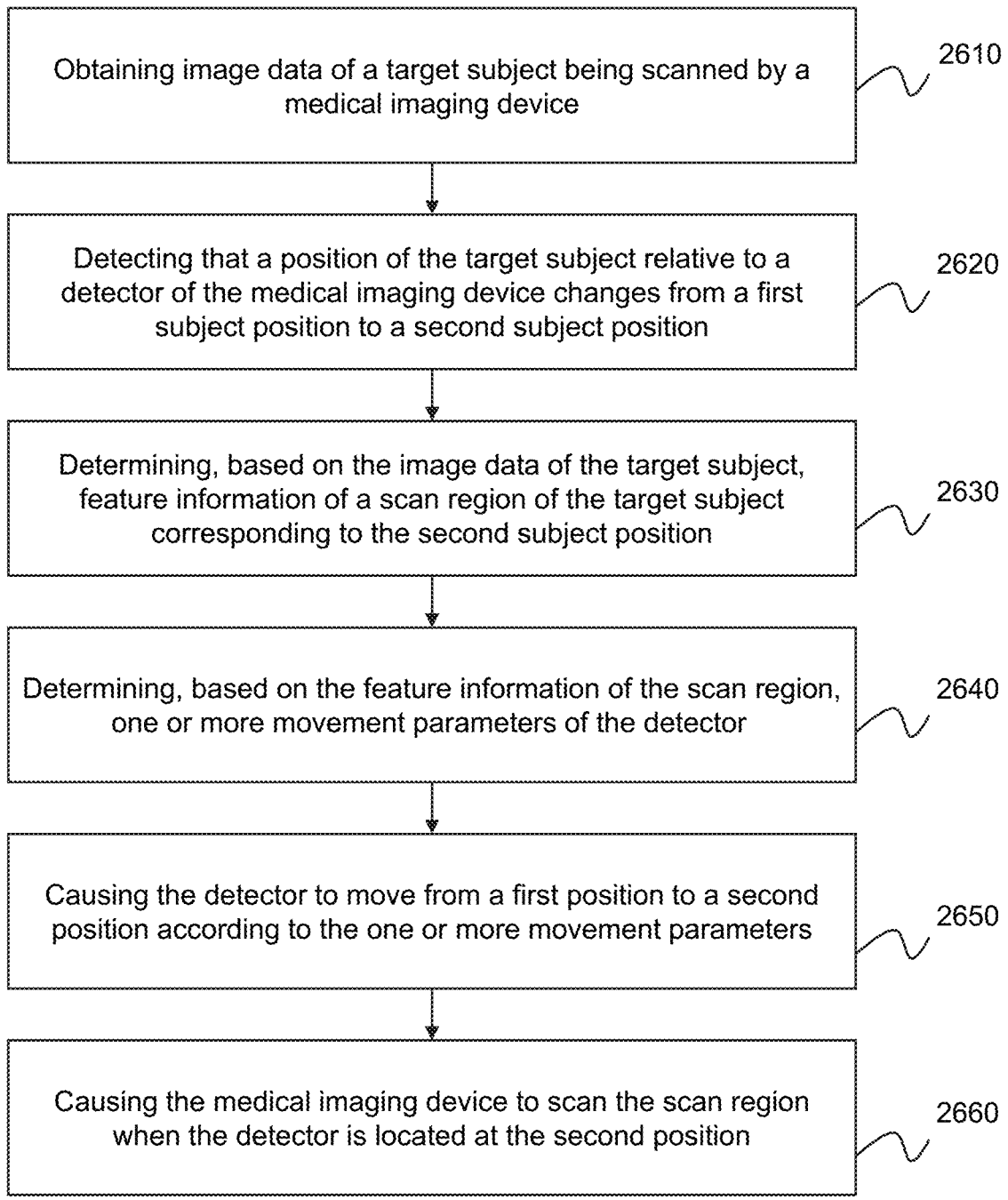
FIG. 26 is a flowchart illustrating an exemplary process for medical imaging according to some embodiments of the present disclosure.

FIG. 26 is a flowchart illustrating an exemplary process for medical imaging according to some embodiments of the present disclosure.

In some embodiments, a target subject (e.g., a patient or a portion thereof) may be scanned by a medical imaging device (e.g., a CT device, a PET device, an MRI device, a DR device). During the scan of the target subject, a position of the target subject with respect to a detector of the medical imaging device may be changed, for example, by adjusting a position of a scanning table of the medical imaging device. In some occasions, the scan region of the target subject may change with the position of the target subject. Normally, different scan regions of the target subject may have different features, such as different thicknesses, attenuation coefficients. If the scan region changes, one or more components of the medical imaging device (e.g., the detector) may need to change their positions to adapt to the change in the scan region. Merely by way of example, the distance between the detector of the medical imaging device and the target subject may need to remain unchanged during the scan of the target subject. If the scanning table on which the target subject is placed is driven to move (e.g., translate and/or rotate) by a user manually or a driving device of the scanning table, the scan region of the target subject may change. Correspondingly, a thickness of the scan region may change. In such cases, a position (e.g., a height) of the detector of the medical imaging device may need to be adjusted to remain the distance between the detector of the medical imaging device and the target subject unchanged. Conventionally, the position of the detector may be adjusted by a user manually. During the adjustment process, the user may move the detector several times to adjust it to a desired position based on subjective judgment, which may be inefficient and inaccurate (e.g., susceptible to human error or subjectivity).

Therefore, it is desirable to provide systems and methods for adjusting component(s) of the medical imaging device to adapt to a change in a scan region during the scan of the target subject. For example, one or more operations of process 2600 as shown in FIG. 26 may be performed during the scan of the target subject to automatically adjust one or more components of the medical imaging device if the scan region of the target subject changes. For illustration purposes, the adjustment of the detector during the scan is described hereinafter as an example.

In 2610, the processing device 120 (e.g., the acquisition module 510) may obtain image data of the target subject being scanned by the medical imaging device.

In some embodiments, the image data may be captured by an image capturing device before or during the scan. For example, the image data may be captured by the image capturing device after the target subject is placed at a scan position (e.g., lies on a scanning table) and before the scan is performed. As another example, the image data may be captured by the image capturing device during the scan. Merely by way of example, the image data may include a plurality of sets of image data captured at a plurality of time points. In some embodiments, the image capturing device may be configured to capture image data of the target subject during the scan continuously or intermittently (e.g., periodically), and transmit the captured image data to the processing device 120 for analysis. In some embodiments, operation 2610 may be performed in a similar manner as operation 610 as described in connection with FIG. 6, and the descriptions thereof are not repeated here.

In 2620, during the scan of the target subject, the processing device 120 (e.g., the analyzing module 520) may detect that a position of the target subject relative to the detector of the medical imaging device changes from a first subject position to a second subject position.

For example, the target subject may be placed on a scanning table (e.g., the scanning table 114 illustrated in FIG. 1) of the medical imaging device. During the scan of the target subject, the scanning table may be driven to move (e.g., translate and/or rotate) by a user manually or a driving device of the scanning table. If the scanning table moves, the processing device 120 may determine that the position of the target subject with respect to the detector changes due to the movement of the scanning table. The movement of the scanning table may be detected by, for example, a position encoder of the scanning table. As another example, the position of the target subject relative to the detector may change if the target subject turns over. The scan region of the target subject may remain unchanged but the thickness of the scan region along a direction from the radiation source and the detector may change if the target subject turns over. For illustration purposes, the scan region corresponding to the first subject position is referred to as a first scan region, and the scan region corresponding to the second subject position is referred to as a second scan region.

In some embodiments, the processing device 120 may detect that the position of the target subject with respect to the detector changes from the first subject position to the second subject position based on the image data of the target subject. For example, the image data may include a first image of the target subject captured at a time point and a second image of the target subject captured at another time point. The processing device 120 may determine the first subject position based on the first image and the second subject position based on the second image. If the difference between the first subject position and the second subject position is greater than a threshold, the processing device 120 may determine that the position of the target subject with respect to the detector changes from the first subject position to the second subject position.

In some embodiments, when the first scan region of the target subject is scanned, the detector of the medical imaging device may be located at a first position corresponding to the first scan region. The detector may need to be moved to adapt to the change in the scan region of the target subject or the motion of the target subject.

In 2630, the processing device 120 (e.g., the analyzing module 520) may determine, based on the image data of the target subject, feature information of the scan region of the target subject corresponding to the second subject position (e.g., the second scan region as described above).

The feature information of the second scan region of the target subject may include a position, a thickness, or the like, of the second scan region. As used herein, the thickness of the second scan region refers to a thickness of the second scan region along a direction of radiation rays (e.g., X-ray beams) emitted from a radiation source (e.g., an X-ray source) of the medical imaging device toward the target subject. For example, the thickness of the second scan region may be an estimated distance that a radiation ray (e.g., a central radiation ray) for scanning the second scan region may traverse within the target subject. As another example, the thickness of the second scan region may be an average distance that multiple radiation rays for scanning the second scan region may traverse within the target subject. As yet another example, the thickness of the second scan region may be a length of the second scan region along a direction perpendicular to a coronal plane of the target subject. In some embodiments, the thickness of the second scan region may also be referred to as an equivalent thickness of the second scan region.

In some embodiments, the processing device 120 may identify a target region corresponding to the second scan region in the image data, and determine the feature information of the second scan region of the target subject based on the target region corresponding to the second scan region. In some embodiments, the image data may include a plurality of sets of image data captured at a plurality of time points as aforementioned. The processing device 120 may identify the target region from any set of image data. Alternatively, the processing device 120 may identify the target region from a set of image data captured when the target subject is at the second subject position. For example, the target subject may be a patient and the second scan region may be the abdomen of the patient. The processing device 120 may identify a target region corresponding to the abdomen of the patient from the set of image data captured at the second subject position according to an image analysis algorithm (e.g., an image segmentation algorithm).

In some embodiments, the processing device 120 may generate a subject model of the target subject based on the image data, and identify the target region from the subject model. More details regarding the generation of the subject model may be found elsewhere in the present disclosure, for example, in operation 660 and the description thereof. More details regarding the identification of the target region from the subject model may be found elsewhere in the present disclosure, for example, in operation 1520 of FIG. 15 and the description thereof.

After the target region is identified from the image data or the subject model, the processing device 120 may determine the feature information of the second scan region of the target subject based on the target region. For example, the processing device 120 may determine a reference thickness of the target region in the image domain, and determine the thickness of the second scan region based the reference thickness and one or more parameters (e.g., intrinsic parameters, extrinsic parameters) of the image capturing device that captures the image data. The one or more parameters of the image capturing device may reflect a transformation from the image domain to the real world.

In 2640, the processing device 120 (e.g., the analyzing module 520) may determine, based on the feature information of the scan region corresponding to the second subject position (i.e., the second scan region), one or more movement parameters of the detector.

For example, the detector may be a flat panel detector. The one or more movement parameters may include a moving distance, a moving direction, a moving speed, or the like, or any combination thereof.

In some embodiments, the detector of the medical imaging device may need to be located at a specific target distance away from the target subject during the scan of the target subject. For example, the change in the scan region of the target subject may be caused by the change in the position of the scanning table and/or a motion of the target subject. As another example, the scan region of the target subject may remain unchanged but the thickness of the scan region along a direction from the radiation source and the detector may change if the target subject turns over. If the scan region changes or the thickness of the scan region changes, the detector may need to change its position to keep the target distance. In some embodiments, the processing device 120 may obtain or determine a target distance between the detector and the target subject, and further determine the movement parameter(s) of the detector based on the target distance and the feature information of the second scan region.

Figure 27:
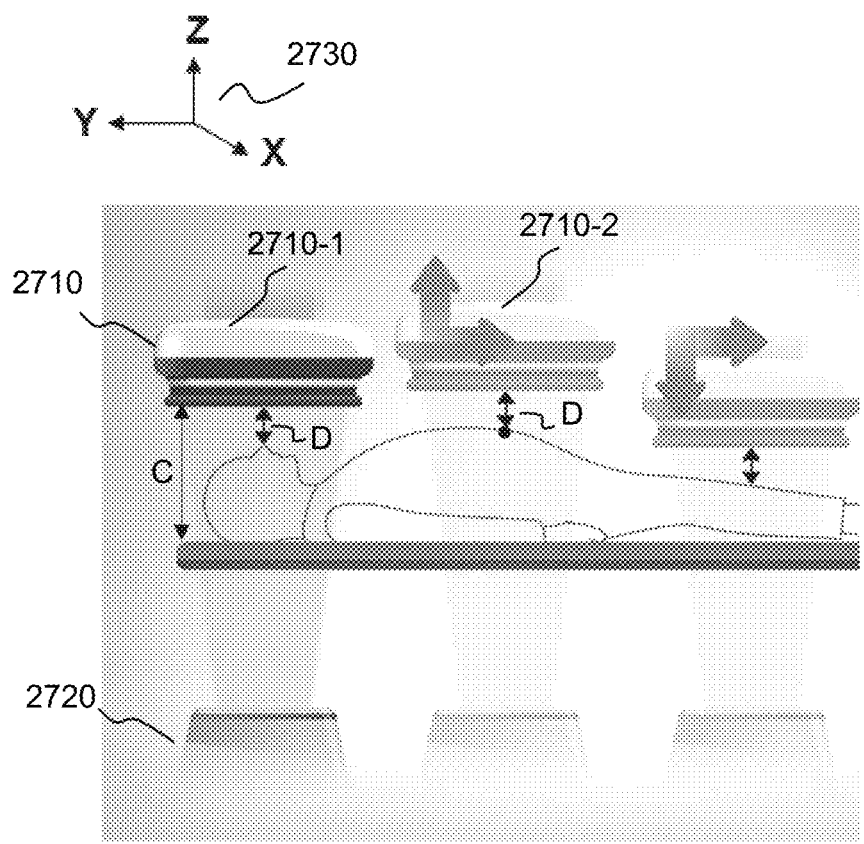
FIG. 27 is a schematic diagram illustrating an exemplary patient to be scanned by a medical imaging device according to some embodiments of the present disclosure.

Merely by way of example, as shown in FIG. 27, a flat panel detector 2710 may be located at a first position 2710-1 corresponding to the head (i.e., the first scan region) of a target subject. When the head of the target subject is being scanned, the distance between the flat panel detector 2710 and the target subject may be equal to a target distance D.

In some embodiments, the target distance D may be set manually by a user (e.g., a doctor) of the imaging system 100, or determined according to a default setting of the imaging system 100, or determined by one or more components (e.g., the processing device 120) of the imaging system 100 according to different situations. For example, the user may manually input the target distance D via a terminal device. As another example, the user may manually move the flat panel detector 2710 to a certain position, and the distance between the flat panel detector 2710 at the certain position and the target subject may be designated as the target distance. As another example, the processing device 120 may determine the target distance based on the image data. For example, the processing device 120 may determine a thickness of the first scan region based on the image data of the target subject. The determination of the thickness of the first scan region may be performed in a similar manner as that of the thickness of the second scan region as described in connection with operation 2630. The processing device 120 may further determine the target distance D based on the thickness of the first scan region and the first position 2710-1 of the flat panel detector 2710. Merely by way of example, the processing device 120 may determine a difference between a distance C as shown in FIG. 27 and the thickness of the first scan region as the target distance D, wherein the distance C is the distance between the first position 2710-1 and the scanning table.

When the scan region changes from the head to the abdomen (i.e., the second scan region) of the target subject, one or more movement parameters of the flat panel detector 2710 may be determined based on the target distance D and feature information of the abdomen of the target subject. For example, it is desired that when the flat panel detector 2710 moves to a second position 2710-2 according to the movement parameter(s), the distance between the flat panel detector 2710 at the second position 2710-2 and the target subject is still equal to the target distance D. In such cases, the distance between the flat panel detector 2710 and the target subject may remain unchanged even if the scan region of the target subject changes, which may avoid collision between the target subject and the flat panel detector 7210 during the scan.

In some embodiments, the processing device 120 may determine the one or more movement parameters of the flat panel detector 2710 based on the target distance D and the thickness of the second scan region of the target subject. For example, if the thickness of the second scan region is larger than the thickness of the first scan region, the moving direction of the flat panel detector 2710 may be the positive direction of the Z-axis of the coordinate system 2730, and the moving distance of the flat panel detector 2710 may be equal to a difference between the thickness of the second scan region and the thickness of the first scan region. If the thickness of the second scan region is less than the thickness of the first scan region, the moving direction of the flat panel detector 2710 may be the negative direction of the Z-axis of the coordinate system 2730, and the moving distance of the flat panel detector 2710 may be equal to the difference between the thickness of the second scan region and the thickness of the first scan region.

In some embodiments, the processing device 120 may further determine one or more movement parameters of the radiation source (e.g., an X-ray tube) and the scanning table based on the one or more movement parameters of the detector and/or an imaging protocol of the target subject. For instance, in response to determining that the position of the target subject relative to the detector changes from the first subject position to the second subject position, the processing device 120 may cause the radiation source and the scanning table to move synchronously. A distance between the scanning table and the radiation source may remain unchanged so that a distance between the subject and the radiation source may remain unchanged. Merely by way of example, the one or more movement parameters of the radiation source and the scanning table may be determined to be the same (i.e., the radiation source may be caused to move in a same direction at a same distance as the scanning table). Alternatively, as shown in FIG. 27, a radiation source 2720 may be located at a fixed distance from the scanning table when the scan region of the target subject changes.

In 2650, the processing device 120 (e.g., the control module 530) may cause the detector to move from the first position to a second position according to the one or more movement parameters.

For example, the processing device 120 may generate an instruction according to the one or more movement parameters of the detector. Further, the processing device 120 may send the instruction to the detector or a driving apparatus that drives the detector to move so as to cause the detector to move to the second position. Additionally or alternatively, the processing device 120 may cause the radiation source and the scanning table to move synchronously according to the one or more parameters.

In some embodiments, before the detector is caused to move from the first position to the second position, the processing device 120 may determine, whether a collision is likely to occur between the target subject and the detector. For example, the processing device 120 may determine an estimated trajectory from the first position to the second position according to the movement parameter(s) of the detector. The processing device 120 may further determine whether a collision is likely to occur between the target subject and the detector based on the second subject position of the target subject and the estimated trajectory. In some embodiments, the processing device 120 may determine whether a distance between the target subject and the estimated trajectory is smaller than a distance threshold (e.g., the first or second distance threshold as described in connection with FIG. 38). If the distance is smaller than the threshold distance, the processing device 120 may determine that a collision is likely to occur. For example, for each of a plurality of estimated positions of the detector in the estimated trajectory, the processing device 120 may determine the distance between the target subject and the estimated position based on the second subject position, the thickness of one or more portions of the target subject, and the estimated position of the detector. In response to determining that the collision is likely to occur, the processing device 120 may adjust at least one of the one or more movement parameters of the detector so as to avoid the collision.

In 2660, the processing device 120 (e.g., the control module 530) may cause the medical imaging device to scan the second scan region when the detector is located at the second position.

In some embodiments, before operation 2660, the second position of the detector may be further checked and/or adjusted. For example, the second position of the detector may be manually checked and/or adjusted by a user of the imaging system 100. The processing device 120 may transmit information associated with the second position to a terminal device of the user. Merely by way of example, the information associated with the second position may be provided to the user in the form of a display image. The display image may illustrate the target subject and one or more components of the medical imaging device including the detector. For example, the display image may illustrate the detector located at the second position and the target subject located at the second subject position. The user may verify the second position and/or adjust the second position by providing a user input via the terminal device. The processing device 120 may obtain the user input from the terminal device and cause the detector to move to the second position (or an adjusted second position) based on the user input. As another example, the processing device 120 may check and/or adjust the second position of the detector based on the image data of the target subject captured using an image capturing device when the target subject is at the second subject position.

According to some embodiments of the present disclosure, during a scan of the target subject, a change in the scan region of the target subject and/or a motion of the target subject may be detected, and the position(s) of one or more components of the medical imaging device may be adjusted automatically to adapt to the change in the scan region. For example, image data of the target subject may be captured continuously or intermittently (e.g., periodically) during the scan to detect a change in the scan region from a first scan region to a second scan region. In addition, one or more movement parameters of the detector of the medical imaging device may be determined based on the image data, such that the detector may be caused to move to a new position corresponding to the second scan region. The systems and methods may achieve an automatic adjustment of the component(s) of the medical imaging device with reduced or minimal or without user intervention. Compared with conventional approaches in which a user needs to manually adjust the components, the systems and methods are more accurate and efficient in reducing, e.g., the workload of a user, cross-user variations, and the time needed for the adjustment of the component(s).

Figure 28:
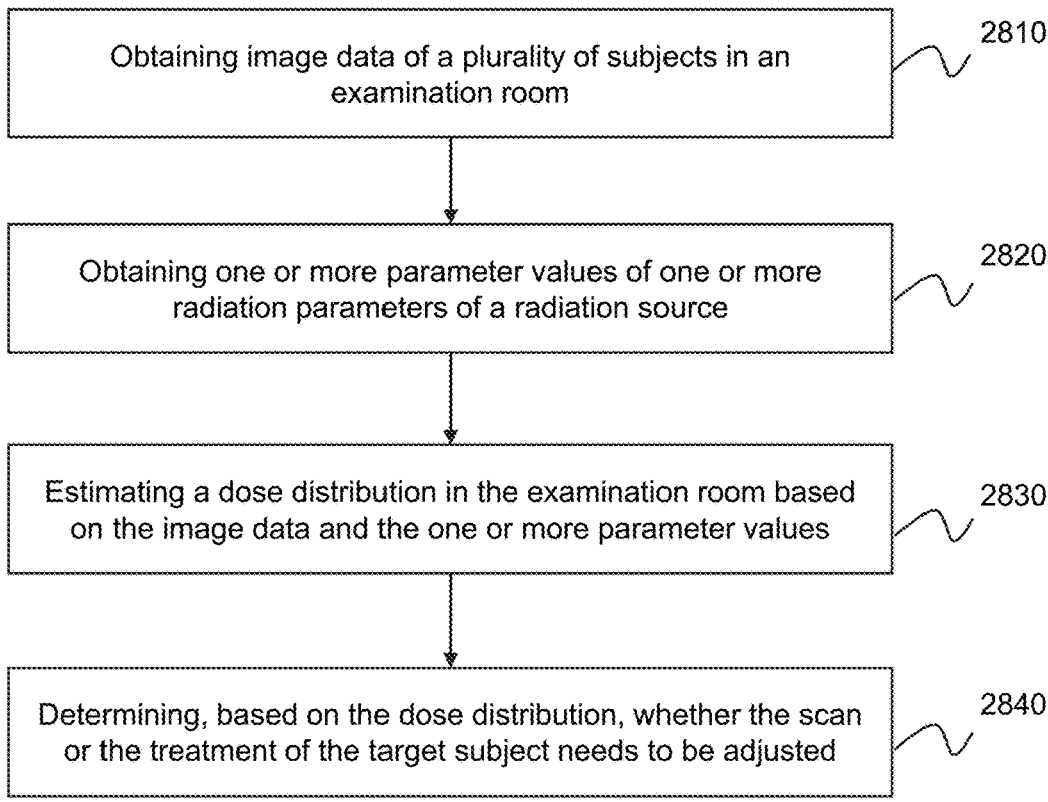
FIG. 28 is a flowchart illustrating an exemplary process for dose estimation according to some embodiments of the present disclosure.

FIG. 28 is a flowchart illustrating an exemplary process for dose estimation according to some embodiments of the present disclosure.

In some embodiments, a scan or a treatment may be performed on a target subject (e.g., a patient or a portion thereof) by a medical device, such as a medical imaging device (e.g., a CT device, a PET device, an MRI device, a DR device), a radiotherapy device, etc. The target subject and the medical device may be located in an examination room. The medical device may include a radiation source for emitting radiation rays to irradiate the target subject during the scan or the treatment of the target subject. Process 2800 may be performed during the scan or the treatment of the target subject. For example, the process 2800 may be performed continuously or intermittently (e.g., periodically) during the scan or the treatment of the target subject to monitor a dose distribution in an examination room.

In 2810, the processing device 120 (e.g., the acquisition module 510) may obtain image data of a plurality of subjects in the examination room.

The image data may be captured by an image capturing device mounted in the examination room. For example, the image capturing device may include a camera, a video camera, an infrared camera, etc. In some embodiments, the image capturing device may include at least two image capturing devices mounted on different places in the examination room. In some embodiments, the image capturing device may capture the image data at a specific time point set by the imaging system 100 or designated by a user (e.g., an operator).

The plurality of subjects may include one or more biological subjects and/or one or more non-biological subjects in the examination room. For example, the plurality of subjects may include the target subject, a medical device for scanning or treating the target subject or a portion of the medical device (e.g., a gantry, a scanning table, a radiation source), an operator who manipulates the scan or the treatment of the target subject, a roof, a floor, a wall, a surgical towel, a lead curtain, a cable, or the like, or a combination thereof. A subject in the examination room may be a moving subject or a stationary subject.

In 2820, the processing device 120 (e.g., the analyzing module 520) may obtain one or more parameter values of one or more radiation parameters of the radiation source.

For example, the one or more radiation parameters may include a voltage of the radiation source, a current of the radiation source, a radiation duration (also referred to as exposure time), an irradiation angle, a position of the radiation source, a position of a detector of the medical device, a shape of a radiation beam emitted by the radiation source, a size of a field of view (FOV), a gantry rotation speed, or the like, or any combination thereof.

In some embodiments, the processing device 120 may obtain a parameter value of a radiation parameter based on a protocol (e.g., an imaging protocol or a treatment protocol) relating to the scan or the treatment performed on the target subject. For example, the protocol may be predetermined and stored in a storage (e.g., the storage device 130). As another example, at least a portion of the protocol may be determined manually by a user (e.g., an operator). Alternatively, the processing device 120 may obtain a parameter value of a radiation parameter from a measurement device that is capable of measuring the radiation parameter. For example, the current of the radiation source may be measured by a current meter and transmitted to the processing device 120. Alternatively, the processing device 120 may determine a parameter value by analyzing the image data acquired in operation 2810. For example, the processing device 120 may determine the position of the radiation source and/or the detector based on the image data.

In 2830, the processing device 120 (e.g., the analyzing module 520) may estimate a dose distribution in the examination room based on the image data and the one or more parameter values.

As used herein, "estimating a dose distribution in the examination room" refers to estimating a dose distribution in at least a portion of the examination room. In some embodiments, the dose distribution in the examination room may include a dose delivered to each of the plurality of subjects (or a portion thereof) in the examination room, and/or a dose delivered to each of a plurality of regions in the examination room. The dose delivered to a subject or a region may be measured by a dose rate and/or a total dose. In some embodiments, a subject or a region in the examination room may include a plurality of portions. The dose delivered to a subject or a region may include a dose delivered to each portion of the subject or the region. For example, a patient may include a plurality of body parts including the head, the chest, the abdomen, the limbs, or the like, or any combination thereof. The dose delivered to the patient may include a dose delivered to each of the body parts of the patient. In some embodiments, the dose distribution may include a dose delivered to each physical point in the examination.

In some embodiments, the dose distribution may be represented in various forms. For example, the dose distribution may be represented as a table or a map recording doses delivered to different subjects and/or regions in the examination room.

In some embodiments, the processing device 120 may estimate the dose distribution in the examination room based on position information of each of the plurality of subjects, the feature information of each of the plurality of subjects, and the one or more parameter values. Exemplary feature information of a subject may include a shape, a height, a width, a thickness, an attenuation coefficient, or the like, or any combination thereof, of the subject. In some embodiments, the processing device 120 may estimate the dose distribution in the examination room using a dose estimation algorithm. Exemplary dose estimation algorithms may include a Monte Carlo algorithm, a greedy algorithm, a dynamic programming algorithm, a divide-and-conquer algorithm, a backtracking algorithm, a branch bound algorithm, a pencil beam algorithm, a cone convolution algorithm, or the like, or any combination thereof. More descriptions regarding the estimation of the dose distribution in the examination room may be found elsewhere in the present disclosure, for example, in FIG. 29 and descriptions thereof.

In some embodiments, the processing device 120 may verify the dose distribution based on at least one measured dose. Each of the at least one measured dose may be measured by a dosimeter at a certain position in the examination room. For example, the processing device 120 may obtain one or more measured doses from one or more dosimeters placed at one or more positions in the examination room. The processing device 120 may further determine a correction parameter based on the measured dose(s) and the dose distribution. The processing device 120 may further correct the dose distribution based on the one or more correction parameters. For example, for each of the position(s) where the dosimeter(s) are located, the processing device 120 may determine an estimated dose delivered to the position according to the dose distribution. The processing device 120 may further determine the correction parameter based on the measured dose and the estimated dose of each position. Merely by way of example, if an average value of the measured dose(s) of the position(s) is greater than the average value of the estimated dose(s) of the position(s), the processing device 120 may determine a correction parameter having a value greater than 1. The processing device 120 may further multiply the correction parameter with the dose distribution to increase the estimated dose delivered to the subjects and/or the regions in the examination room.

In some embodiments, the processing device 120 may obtain the correction parameter from the storage device 130. The correction parameter may be determined in advance based on an estimated dose distribution of a reference scan or a reference treatment of a reference subject, and one or more measured doses that are measured in the reference scan or the reference treatment using one or more dosimeters.

In some embodiments, the processing device 120 may determine an absorbed dose of a subject (e.g., the target subject and/or an operator) based on the dose delivered to the subject and attenuation information of the subject. The absorbed dose of a subject may be measured by a dose rate, a total dose, a dose absorbed by different portions of the subject, or the like, or any combination thereof. Taking the target subject as an example, the processing device 120 may determine an absorbed dose of each of a plurality of portions of the target subject based on a dose delivered to the portion of the target subject and the attenuation coefficient of the portion of the target subject. As another example, the processing device 120 may determine a total absorbed dose of the target subject based on a difference between the energy of radiation particles that reach the target subject and the energy of the radiation particles after passing through the target subject.

In 2840, the processing device 120 (e.g., the analyzing module 520) may determine, based on the dose distribution, whether the scan or the treatment of the target subject needs to be adjusted.

For example, the processing device 120 (e.g., the acquisition module 510) may obtain a dose delivery threshold relating to the target subject. The processing device 120 may determine whether the dose delivered to the target subject exceeds the dose delivery threshold. In response to determining that the dose delivered to the target subject exceeds the dose delivery threshold, the processing device 120 may determine that the scan or the treatment of the target subject needs to be adjusted. Additionally or alternatively, the processing device 120 may obtain a dose absorption threshold relating to the target subject. The processing device 120 may determine whether the dose absorbed by the target subject exceeds the dose absorption threshold. In response to a determination that the dose absorbed by the target subject exceeds the dose absorption threshold, the processing device 120 may determine that the scan or the treatment of the target subject needs to be adjusted. The dose delivery threshold and/or the dose absorption threshold may be determined according to a default setting of the imaging system 100, or manually set by a user (e.g., an operator), or determined by the processing device 120 according to an actual need.

In some embodiments, in response to determining that the scan or the treatment of the target subject needs to be adjusted, the processing device 120 may cause a first notification to be generated. For example, the first notification may be configured to notify the operator that the scan or the treatment of the target subject needs to be adjusted. In some embodiments, to adjust the scan or the treatment of the target subject, the processing device 120 and/or the operator may adjust one or more scan parameters related to the scan or the treatment. For example, the processing device 120 and/or the operator may terminate the scan or the treatment when the dose delivered to the target subject exceeds the dose delivery threshold.

In some embodiments, the processing device 120 may determine a recommended operating region for the operator to manipulate the scan or the treatment based on the dose distribution in the examination room. For example, based on the dose distribution, the processing device 120 may determine a region that is in the vicinity of the target subject and/or the medical device and corresponds to a low dose (e.g., the dose delivered to the region being lower than a threshold value), and designate the determined region as the recommended operating region. As another example, the processing device 120 may determine a dose delivered to each of a plurality of regions in the examination room, and determine the recommended operating region by selecting the region having the minimum dose from the plurality of regions. In some embodiments, the processing device 120 may cause a terminal device (e.g., the terminal device 140) to generate a second notification regarding the recommended operating region. For example, the second notification may be in the form of a text, an image, an animation, a voice message, a video, or the like, or any combination thereof. In some embodiments, the processing device 120 may determine whether the operator is located in the recommended operating region, and cause the second notification to be generated if the operator is not located in the recommended operating region. The dose delivered to the operator may be relatively low in the recommended operating region. Thus, the determination of the recommended operating region may help reduce health damage to the operator caused by the radiation beam during the scan or the treatment of the target subject.

In some embodiments, the processing device 120 (e.g., the analyzing module 520) may generate a dose distribution map based on the dose distribution in the examination room and the image data acquired in operation 2810. For example, the dose distribution map may include an image or a map illustrating the examination room and the dose delivered to the subjects and/or regions in the examination room. In some embodiments, the dose distribution map may be generated by annotating the dose delivered to the subjects and/or regions in the examination room on the image data. For instance, in the dose distribution map, different portions of the target subject and/or the operator may be displayed in different colors according to the doses delivered to the portions. As another example, if the dose delivered to a portion of the target subject exceeds a dose delivery threshold, the portion may be marked by a specific color or an annotation for reminding the high dose delivered to the portion. In some embodiments, the dose distribution map may be displayed on a terminal device of the operator to represent the dose distribution in the examination room intuitively and efficiently.

In some embodiments, the processing device 120 may determine a position of the lead curtain based on the dose distribution in the examination room. For example, if the lead curtain is hung on the ceiling of the examination room, and the dose near the operator of the medical imaging device is relatively large, the lead curtain may be put down to separate the operator and the radiation source to prevent the operator from being injured by the radiation.

Figure 29:
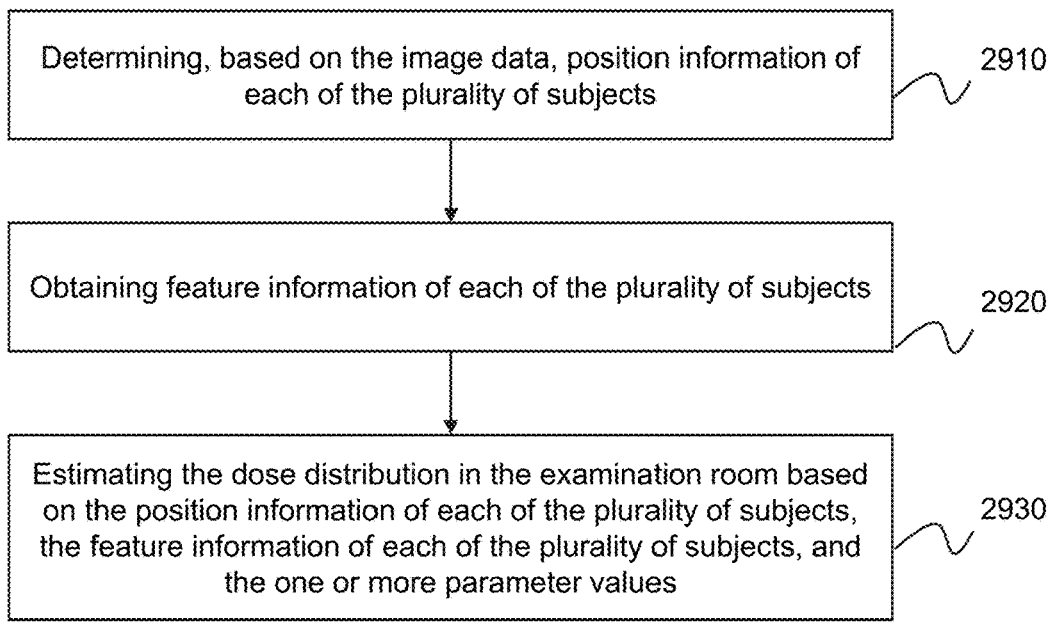
FIG. 29 is a flowchart illustrating an exemplary process for estimating a dose distribution in an examination room according to some embodiments of the present disclosure.

In some embodiments, operation 2830 of the process 2800 may be implemented by one or more operations of process 2900 as illustrated in FIG. 29.

In 2910, the processing device 120 (e.g., the analyzing module 520) may determine, based on the image data, position information of each of the plurality of subjects in the examination room.

For example, the position information of a subject may include a position of the subject in the examination room (e.g., represented as a coordinate of the subject in a coordinate system with respect to the examination room), a position of the subject with respect to one or more other subjects (e.g., the radiation source of the medical device) in the examination room. The position information of the subject may be determined by the processing device 120 by analyzing the image data. Alternatively, the processing device 120 may obtain the position information of the subject from a position measurement device configured to measure the position of the subject. Merely by way of example, the position information of a scanning table of the medical device may be obtained from a position encoder of the scanning table.

In some embodiments, the processing device 120 may determine position information of one or more portions of the target subject, such as the heart, the chest, the head, etc. For example, the processing device 120 may obtain a subject model representing the target subject and determine the position information of the one or more portions of the target subject based on the subject model. The subject model may indicate an appearance of the target subject, such as a body shape, a size (e.g., a height, a width, a thickness), or the like, or any combination thereof. The position information of a portion of the target subject may include, for example, a position of a body surface of the portion of the target subject in the examination room, a position of the body surface of the portion of the target subject with respect to one or more other subjects in the examination room (e.g., the radiation source).

In some embodiments, the subject model may be predetermined based on image data of the target subject and stored in a storage device (e.g., the storage device 130). The processing device 120 may acquire the subject model from the storage device. As another example, the processing device 120 may determine the subject model based on the image data obtained in operation 2810. Based on the obtained or generated subject model, the processing device 120 may determine the position information of a portion of the target subject. Merely by way of example, the target subject may lie on a scanning table, and the processing device 120 may determine a distance between the body surface of the chest of target subject and the radiation source based on the position of the scanning table, the position of the radiation source, and the thickness of the chest of the target subject. The thickness of the chest of the target subject may be determined based on the subject model.

Additionally or alternatively, the processing device 120 may obtain or generate an operator model representing the operator. The processing device 120 may further determine the position information of one or more portions of the operator based on the operator model. The operator model may be obtained or generated in a way similar to how the subject model is obtained or generated as aforementioned. The determination of the position information of a portion of the operator may be performed in a similar manner to that of the position information of a portion of the target subject as aforementioned.

In 2920, the processing device 120 (e.g., the analyzing module 520) may obtain feature information of each of the plurality of subjects.

Exemplary feature information of a subject may include a shape, a height, a width, a thickness, an attenuation coefficient, or the like, or any combination thereof, of the subject. In some embodiments, different portions of a subject may have features such as different thicknesses, widths, and attenuation coefficients. The feature information of the subject may include feature information (e.g., a thickness, an attenuation coefficient) of each portion of the subject.

In some embodiments, the processing device 120 may obtain at least a portion of the feature information of a subject from the storage device 130. For example, the processing device 120 may obtain the attenuation coefficient of the subject from the storage device 130. Additionally or alternatively, the processing device 120 may determine at least a portion of the feature information based on the image data acquired in operation 2810. For instance, the processing device 120 may determine the height, the width, the thickness, or the like, or a combination thereof, of the subject based on the image data. As another example, a model representing the subject (e.g., the subject model representing the target subject) may be generated based on the image data, and the processing device 120 may determine the height, the width, the thickness, and/or other feature information based on the model.

In 2930, the processing device 120 (e.g., the analyzing module 520) may estimate the dose distribution in the examination room based on the position information of each of the plurality of subjects, the feature information of each of the plurality of subjects, and the one or more parameter values.

In some embodiments, the processing device 120 may estimate the dose distribution in the examination room using a dose estimation algorithm as described elsewhere in this disclosure (e.g., FIG. 28 and the relevant descriptions).

Merely by way of example, the processing device 120 may estimate the dose distribution in the examination room using a Monte Carlo algorithm. For example, the processing device 120 may determine an original state of each radiation particle emitted from the radiation source of the medical device based on the one or more scan parameters related to the radiation source. The original state of each radiation particle may indicate an energy, a moving direction, a position, or other parameters related to the radiation particle, or a combination thereof. The processing device 120 may simulate a transport process of each radiation particle based on one or more physical processes that may occur during the transport process of the radiation particle. The processing device 120 may further determine an estimated state of each radiation particle based on the original state of each radiation particle and the transport process of each radiation particle. The one or more physical processes may include, for example, a collision between the radiation particle and an atom (or a portion thereof) in a medium that the radiation particle is penetrating, a change in the energy of the radiation particle after the collision, a generation of secondary particles (e.g., electrons) after the collision, a change in the moving direction of the radiation particle, or the like, or any combination thereof. For instance, the processing device 120 may use one or more functions to randomly determine whether a physical process may occur or not.

In some embodiments, the process 2800 and/or the process 2900 may be performed continuously or intermittently (e.g., periodically) during the scan or the treatment of the target subject. For example, the image capturing device may be configured to capture image data during the scan or the treatment of the target subject continuously or intermittently (e.g., at predetermined time intervals (e.g., 0.5 seconds, 0.2 seconds)). After the image capturing device captures a set of image data at a specific time point, it may transmit the set of image data to the processing device 120. The processing device 120 may perform the process 2800 to determine the dose distribution in the examination room at the specific time point. In some embodiments, the acquisition of the set of image data, the transmission of the set of image data to the processing device 120, and the analysis of the set of image data may be performed substantially in real time so that a substantially real-time dose distribution in the examination room may be monitored.

Conventionally, the dose distribution in the examination room may be determined without image data of the plurality of subjects in the examination room. The dose distribution in the examination room may be determined based on position information of one or more movable components acquired by one or more position sensors and position information of a stationary subject stored in the storage device. For example, the dose delivered to the target subject may be determined based on a preset physical point in the examination room that represents the position of the target subject (e.g., a point that is located at a specific distance from the radiation source). Additionally or alternatively, the dose delivered to different target subjects in different scans or treatments may be determined using a same predetermined model (e.g., an ellipsoid model) that roughly represents the shape of the target subject. As another example, conventionally, the operator selects an operating region in the examination room based on experience.

Compared with the conventional approach, the systems and methods described herein may improve the accuracy and/or efficiency of dose estimation. For example, image data of a plurality of subjects in the examination room may be acquired by an imaging capturing device. At least a portion of the feature information of each subject may be determined based on the image data. The position information of each subject may be monitored in real time based on the image data. Additionally or alternatively, the position information of each subject may be monitored based on the image data and/or position data measured by one or more position sensors in the examination room. Thus the position information of each subject may be determined more accurately. According to some embodiments of the present disclosure, a subject model corresponding to the target subject and/or an operator model corresponding to the operator may be generated or obtained for determining feature information and/or position information of the target subject and/or the operator. The subject model and the operator model may reflect contour information of the target subject and the operator, respectively. Compared with using a predetermined model for dose estimation during scans or treatments on different target subjects, using the subject model and the operator model may be more accurate, thereby improving the accuracy of the estimated dose distribution in the examination room. In addition, the systems and methods for dose estimation disclosed herein may be implemented with reduced or minimal or without user intervention, which may be more accurate and efficient by, e.g., reducing the workload of a user, cross-user variations, and the time needed for the dose estimation.

In some embodiments, one or more additional operations not described may be added and/or one or more of the operations discussed may be omitted. Additionally, the order of the operations illustrated in FIGS. 29-28 and described above is not intended to be limiting. For example, the process 2800 may further include an operation to transmit the dose distribution map to a storage device (e.g., the storage device 130). As another example, the process 2800 may be combined with the process 900 to generate a target image Ti' illustrating an internal structure of a scan region of the target subject to be scanned. Different portions of the internal structure of the scan region may be illustrated using different colors to indicate an estimated dose delivered to or absorbed by each of the different portions. As still another example, operation 2840 may be omitted. As still another example, the process 2800 may further include an operation to cause a terminal device to display the does distribution. The user may adjust the scan or the treatment of the target subject based on the displayed does distribution.

Figure 30:
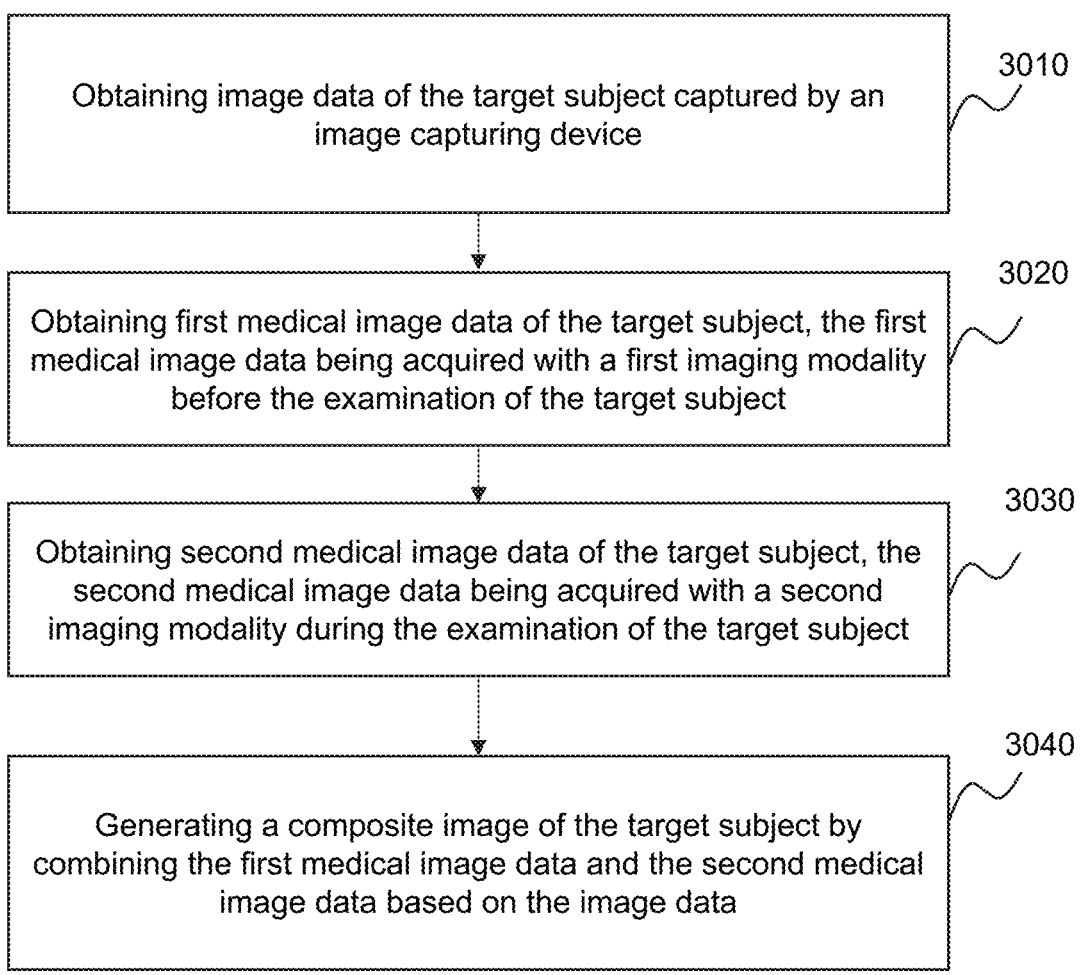
FIG. 30 is a flowchart illustrating an exemplary process for examining a target subject according to some embodiments of the present disclosure.

FIG. 30 is a flowchart illustrating an exemplary process for examining a target subject according to some embodiments of the present disclosure.

In some embodiments, the examination of the target subject may include an imaging process (e.g., optical imaging, medical scan imaging, etc.) performed on the target subject. Image data obtained in the imaging process may be further used for medical diagnosis and/or treatment.

In some embodiments, the examination of the target subject may include a treatment of the target subject implemented by an invasive device, for example, when the target subject has a tumor or a vascular malformation. An invasive device refers to a medical device that needs to be inserted into the target subject to achieve the treatment of the target subject. Exemplary invasive devices may include a needle, a guide wire, a sheath, a sheath, an endoscopy, a laparoscopy, an arthroscopy, a sucker, a catheter, etc. For example, the invasive device may be a guide wire that is made of metals, such as nickel-titanium.

During the treatment, a trajectory and/or a position of the invasive device relative to an internal structure (e.g., a blood vessel or a tumor) of the target subject may need to be monitored, such that a user (e.g., a doctor or an operator) of the invasive device can adjust the trajectory and/or the position of the invasive device. Conventionally, during the treatment of the target subject, an X-ray imaging device (e.g., a DR device, a DSA device) may be used to capture X-ray images of the target subject continuously or intermittently (e.g., periodically). The X-ray images may illustrate the invasive device within the target subject but include limited anatomical information of the target subject and cannot illustrate the position of the invasive device relative to the internal structure of the target subject clearly. In order to improve the treatment accuracy and efficiency, it is desired to provide systems and methods for monitoring the invasive device during the treatment of the target subject. According to some embodiments of the present disclosure, the process 3000 may be performed to generate a composite image to provide a real-time position of the invasive device relative to the internal structure of the target subject, such that the trajectory and/or the position of the invasive device may be monitored and/or adjusted more accurately and efficiently during the treatment.

In 3010, the processing device 120 (e.g., the acquisition module 510) may obtain image data of the target subject (e.g., a patient) captured by an image capturing device (e.g., the image capturing device 160).

The image data may be captured before or during the examination of the target subject. Taking the treatment implemented by an invasive device as an example, the image data of the target subject may be captured before the invasive device is inserted into the target subject. The image data of the target subject may indicate an appearance, such as the posture and/or the contour, of the target subject. In some embodiments, the acquisition of the image data may be performed in a similar manner as that as described in connection with operation 610.

In 3020, the processing device 120 (e.g., the acquisition module 510) may obtain first medical image data of the target subject.

The first medical image data may be acquired with a first imaging modality in which anatomical information of a subject may be acquired. Exemplary first imaging modality may include a CT imaging, an MR imaging, a PET imaging, an ultrasound imaging, or the like, or any combination thereof.

In some embodiments, the first medical image data may indicate an internal structure (e.g., organs and/or tissues) of the target subject. In some embodiments, the first medical image data may include a historical anatomical image of the target subject (or a portion thereof) captured before the examination of the target subject. For example, the first medical image data may include a historical CT image or a historical MRI image of the target subject. As another example, the first medical image may include an angiographic image of the target subject captured before the examination of the target subject. The angiographic image of the target subject may be acquired by a DSA device after a contrast agent is injected into the target subject.

In 3030, the processing device 120 (e.g., the acquisition module 510) may obtain second medical image data of the target subject.

The second medical image may be acquired with a second imaging modality different from the first imaging modality. Exemplary second imaging modality may include an X-ray imaging (e.g., a DR imaging, a DSA imaging).

In some embodiments, the second medical image data may include a fluoroscopy of the target subject. Taking the treatment implemented by an invasive device as an example, the second medical image data may include a fluoroscopy indicative of the position of the invasive device relative to the target subject. In some embodiments, the second medical image data may be captured during the treatment of the target subject. For example, a needle or a guide wire may be inserted into the target subject for treating the target subject. After the needle or the guide wire is inserted into the target subject, the second medical image data may be acquired in real time or intermittently (e.g., periodically), which may indicate a movement and a position of the needle or the guide wire relative to the target subject. As another example, the second medical image data may be acquired before the needle or the guide wire is inserted into the target subject.

In some embodiments, compared with the first medical image data as described in connection with operation 3020, the second medical image data may include less anatomical information of the target subject but more real-time information (e.g., real-time position information of the invasive device). For example, the first medical image data may be acquired by a CT device or an MRI device, and the second medical image data may be acquired by a DR device. As another example, the first medical image data may be an angiographic image representing blood vessels of the target subject, which may be acquired by a DSR device after a contrast agent is injected into the target subject. The second medical image data may be an image captured by the DSR device after a guide wire is inserted into the target subject when no contrast agent is injected into the target subject. The second medical image data may indicate the position of the guide wire in the target subject but cannot illustrate blood vessels of the target subject.

In 3040, the processing device 120 (e.g., the analyzing module 520) may generate a composite image of the target subject by combining the first medical image data and the second medical image data based on the image data. For example, the composite image may include both the anatomical information included in the first medical image data and the real-time information included in the second medical image data.

In some embodiments, the processing device 120 may generate registered first medical image data by registering the first medical image data with the image data. Further, the processing device 120 may generate the composite image by combining the registered first medical image data and the second medical image data. In other words, the image data may serve as a mediator for combining the first medical image data and the second medical image data. For example, the second medical image data may be a fluoroscopy acquired during the examination of the target subject, and the first medical image data may be a historical anatomical image (e.g., a CT image) of the target subject. In some cases, the second medical image data cannot be directly combined with the first medical image data because the historical anatomical image may be a 3D image and the fluoroscopy may be a 2D image, or the second medical image data may include insufficient anatomical information to be registered with the first medical image data. The image data may represent a state (e.g., a current state) of the target subject during the examination and can be used to register the first medical image data so that the registered first medical image data may be combined with the second medical image data.

In some embodiments, the registered first medical image data and the second medical image data may correspond to a same view (e.g., the front view) of the target subject. In such cases, the processing device 120 may overlap the registered first medical image data on the second medical image data directly so as to generate the composite image. Alternatively, the second medical image data may correspond to a specific view of the target subject, and the registered first medical image data may be 3D image data. The processing device 120 may extract a 2D image corresponding to the specific view of the target subject from the registered first medical image data, and generate the composite image by overlapping the second medical image data and the extracted 2D image. Alternatively, the composite image may be generated based on the registered first medical image data and the second medical image data in a similar manner as how the reference subject model is generated as described in connection with operation 2220. In some embodiments, the processing device 120 may combine the registered first medical image data with the second medical image data according to an image fusion algorithm.

In some embodiments, the composite image may be generated by combining the first medical image data, the second medical image data, and the image data. Merely by way of example, the processing device 120 may generate, based on the image data of the target subject, a subject model representing the target subject. The generation of the subject model may be performed in a similar manner as that as described in connection with operation 2210. Further, the processing device 120 may generate the composite image of the target subject by combining the subject model, the first medical image data, and the second medical image data. For example, the processing device 120 may combine the subject model, the first medical image data, and the second medical image data by performing one or more image processing operations (e.g., a fusion operation, an image registration operation) as that as described in connection with operation 2220.

In some embodiments, the processing device 120 may identify, in the subject model, one or more first regions each of which corresponds to one of one or more ROIs of the target subject. The processing device 120 may identify, in the first medical image data, one or more second regions each of which corresponds to the one of the one or more ROIs of the target subject. The processing device 120 may identify, in the second medical image data, one or more third regions each of which corresponds to the one of the one or more ROIs of the target subject. The processing device 120 may generate the composite image based on the one or more first regions, the one or more second regions, and the one or more third regions. The generation of the composite image based on the ROI(s) may be performed in a similar manner as the generation of the reference subject model based on the ROI(s) as described in operation 2020. For instance, for each ROI of the target object, the processing device 120 may align the second region corresponding to the ROI and the third region corresponding to the ROI with the first region corresponding to the ROI.

In some embodiments, the processing device 120 may determine, based on the subject model, one or more first values of one or more contour parameters of the target subject. The processing device 120 may determine, based on the first medical image data, one or more second values of the one or more contour parameters of the target subject. The processing device 120 may determine, based on the second medical image data, one or more third values of the one or more contour parameters of the target subject. The processing device 120 may generate the composite image based on the one or more first values, the one or more second values, and the one or more third values of the one or more contour parameters. The generation of the composite image based on the contour parameter(s) may be performed in a similar manner as the generation of the reference subject model based on the contour parameter(s) as described in operation 2220.

In some embodiments, the processing device 120 may generate the composite image by combining the first medical image data, the second medical image data, and the original image data. In some embodiments, the processing device 120 may generate a reference subject model by combining the first medical image data and the image data, for example, by performing operation 2130 as described in connection with FIG. 21. The processing device 120 may further generate the composite image by combining the reference subject model and the second medical image data. Alternatively, the processing device 120 may generate a first combined image by combining the image data and the second medical image data, and then generate the composite image by combining the first combined image and the first medical image data. Alternatively, the processing device 120 may generate a second combined image by combining the first and second medical image data, and then generate the composite image by combining the second combined image and the image data.

In some embodiments, the processing device 120 may use the composite image of the target subject to facilitate the examination of the target subject, e.g., to guide a movement of the invasive device in the target subject. For example, during a puncture treatment of the target subject, the composite image may indicate a position of a needle relative to a tumor of the target subject and guide the movement of the needle for better treatment. For instance, according to the composite image, an orientation of the needle relative to the tumor and/or a depth of the needle relative to the tumor may be adjusted. As another example, during a treatment of the target subject having a vascular malformation, the composite image may be used as a 3D roadmap that indicates a position of a guide wire relative to a blood vessel and guides the movement of the guide wire in the blood vessel for better treatment. For instance, according to the composite image, the guide wire may be caused to move along the blood vessel of the target subject accurately.

In some embodiments, the processing device 120 may further cause a terminal device (e.g., the terminal device 140) to display the composite image during the examination of the target subject. For example, the terminal device may display the second medical image data and the corresponding composite image simultaneously. In some embodiments, the image data may be acquired in real time or intermittently (e.g., periodically). The processing device 120 may obtain updated image data and generate updated registered first medical image data by registering the first medical image data with the updated image data. Further, the processing device 120 may generate an updated composite image of the target subject by combining the updated registered first medical image data and the second medical image. Additionally or alternatively, the second medical image data of the target subject may be acquired in real time or intermittently (e.g., periodically) during the examination of the target subject. The processing device 120 may obtain updated second medical image data and generate an updated composite image of the target subject by combining the updated registered first medical image data and the updated second medical image. Then, the processing device 120 may cause the terminal device to display the updated composite image. In such cases, a real-time composite image may be generated to indicate a real-time status of the target subject.

For example, the real-time composite image may be generated such that the trajectory and/or the position of the invasive device may be monitored and/or adjusted more accurately and efficiently during the examination.

According to some embodiments of the present disclosure, first medical image data acquired with a first imaging modality before the examination of the target subject and second medical image data acquired with a second imaging modality during the examination of the target subject may be combined based on image data to generate a composite image. The composite image may include more comprehensive information of the target subject (e.g., both the internal structure of the target subject and a real-time position of the invasive device) and can be used to guide the treatment of the target subject. For example, the composite image may be displayed to an operator of the invasive device, and the operator may adjust the trajectory and/or the position of the invasive device according to the composite image. Compared with conventional ways in which an operator may need to operate the invasive device based on experience or an image includes limited anatomical information of the target subject, the systems and methods disclosed herein may be more accurate and efficient by, e.g., reducing the workload of the operator, cross-user variations, and providing more comprehensive information to the operator. In addition, in some embodiments, the image data and/or the second medical image data may be updated in real time or intermittently (e.g., periodically), and an updated composite image may be generated based thereon. In this way, the target subject and/or the invasive device may be monitored in real time or intermittently (e.g., periodically) and the treatment of the target subject may be adjusted in time, thereby improving the treatment accuracy. In some embodiments, one or more operations may be added or omitted. For example, a process for generating a subject model may be added before operation 3040. In some embodiments, two or more operations may be performed simultaneously. For example, operation 3010 and operation 3020 may be performed simultaneously. In some embodiments, one or more operations of process 3100 may be added to monitor the motion of the target subject during the examination.

Figure 31:
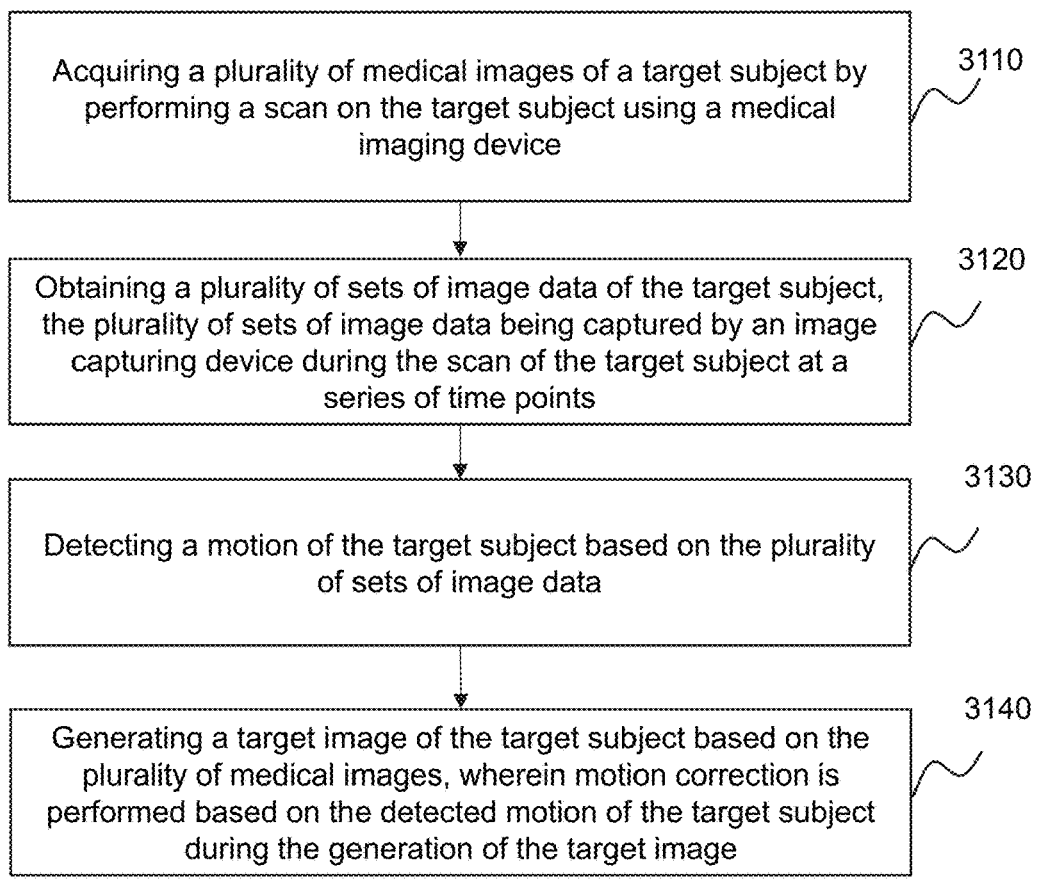
FIG. 31 is a flowchart illustrating an exemplary process for motion correction in medical imaging according to some embodiments of the present disclosure.

FIG. 31 is a flowchart illustrating an exemplary process for motion correction in medical imaging according to some embodiments of the present disclosure.

In some occasions, during a scan performed on a target subject, the target subject may move, which may reduce an image quality of a resulting medical image of the scan (e.g., cause motion artifacts in the resulting medical image). Traditionally, the motion artifacts in the medical image may be post-processed and corrected after the imaging process is finalized. The imaging process cannot be adjusted promptly to compensate for the motion of the target subject. For example, the target subject may be treated by an invasive device, and the image process is performed during the treatment to image the invasive device in the target subject. If the target subject moves while motion correction cannot be performed promptly, a resulting medical image may have a low accuracy, which may affect the treatment accuracy. In some embodiments, the process 3100 may be performed during the imaging of the target subject to achieve a prompt (e.g., real-time) compensation for the motion of the target subject.

In 3110, the processing device 120 (e.g., the acquisition module 510) may acquire a plurality of medical images of the target subject (e.g., a patient or a portion thereof) by performing a scan on the target subject using a medical imaging device.

A medical image of the target subject may be a 2D image, a 3D image, a 4D image (e.g., a time series of 3D images), etc. of the target subject. In some embodiments, the medical imaging device may include an X-ray imaging device (e.g., a DSA device).

In some embodiments, the plurality of medical images may be generated during different stages of the scan performed on the target subject. For example, the scan may be a DSA scan configured to image blood vessels of the target subject. To perform the DSA scan, the target subject may be injected with a contrast agent. The plurality of medical images may include a first medical image acquired before the contrast agent is injected into the target subject and a second medical image acquired after the contrast agent is injected into the target subject. For illustration purposes, it is assumed that the first medical image is acquired at a first time point and the second medical image is acquired at a second time point after the first time point. In some embodiments, the first medical image may serve as a mask. If the target subject keeps in a still state during a period between the first and second time points, a difference image between the second medical image and the first medical image may illustrate blood vessels of the target subject without other organs or tissues of the target subject. If the target subject moves during a period between the first and second time points, a difference image between the second medical image and the first medical image may have a reduced quality (e.g., have motion artifacts and illustrate other organs or tissues of the target subject). The first medical image may need to be corrected to remove or eliminate the effect of the movement of the target subject.

As another example, the target subject may be treated by an invasive device, and the scan may be performed during the treatment. The plurality of medical images may include a third medical image captured before the invasive device is inserted into the target subject and a fourth medical image acquired after the invasive device is inserted into the target subject. In some embodiments, one or more roadmaps for guiding the movement of the invasive device may be generated based on the scan performed during the treatment. For example, the roadmap(s) may include the medical images acquired during the scan and/or one or more images generated based on the medical images (e.g., a second target image as described below). In some embodiments, the scan that can generate one or more roadmaps for guiding the movement of the invasive device may also be referred to as a roadmap scan. In some embodiments, the acquisition of the plurality of medical images may be performed in a similar manner as the acquisition of the second medical image data as described in operation 3030. For illustration purposes, it is assumed that the third medical image is acquired at a third time point and the fourth medical image is acquired at a fourth time point after the third time point. In some embodiments, the third medical image may serve as a mask. If the target subject keeps in a still state during a period between the third and fourth time points, a difference image between the third medical image and the fourth medical image may illustrate the invasive device in the target subject. If the target subject moves during a period between the third and fourth time points, a difference image between the fourth medical image and the third medical image may have a reduced quality (e.g., have motion artifacts). The third medical image may need to be corrected to remove or eliminate the effect of the movement of the target subject.

In 3120, the processing device 120 (e.g., the acquisition module 510) may obtain a plurality of sets of image data of the target subject.

The plurality of sets of image data may be captured by an image capturing device (e.g., the image capturing device 160) during the scan of the target subject at a series of time points (or referred to as a time series). Each of the plurality of sets of image data may correspond to one of the series of time points. In some embodiments, each of the plurality of medical images of the target subject acquired in operation 3110 may correspond to one of the series of time points. A medical image and a set of image data that correspond to a same time point may be regarded as corresponding to each other. In other words, the image capturing device and the medical imaging device may be directed to acquire a set of image data and a medical image, respectively, at a same (or substantially same) time point.

In some embodiments, operation 3120 may be performed in a similar manner as operation 2510, and the descriptions thereof are not repeated here.

In 3130, the processing device 120 (e.g., the analyzing module 520) may detect, based on the plurality of sets of image data, a motion of the target subject.

As used herein, a motion of the target subject may be measured by one or more motion parameters, such as a moving distance, a moving direction, a moving trajectory, a change of a posture, or the like, or any combination thereof, of the target subject (or a portion thereof). In some embodiments, the motion of the target subject may include a motion of the target subject on an XY plane of the coordinate system 170 as shown in FIG. 1. In some embodiments, the motion of the target subject may be represented as a motion vector. The determination of the motion of the target subject may be in a similar manner as that as described in connection with operation 2520, and the descriptions thereof are not repeated here.

In some embodiments, the plurality of medical images may include a first medical image acquired before the contrast agent is injected into the target subject and a second medical image acquired after the contrast agent is injected into the target subject. The processing device 120 may determine a first time point at which the first medical image is acquired and a second time point at which the second medical image is acquired. The processing device 120 may select a first set of image data corresponding to the first medical image from the plurality of sets of image data, wherein the first set of image data may be acquired at a time point that is the closest to or same as the first time point. The processing device 120 may determine a second set of image data corresponding to the second medical image from the plurality of sets of image data, wherein the second set of image data may be acquired at a time point that is the closest to or same as the second time point. The processing device 120 may determine a motion of the target subject between the first time point and the second time point based on the first set of image data and the second set of image data. In some embodiments, a plurality of second medical images may be acquired. For each of the second medical images, the processing device 120 may determine a motion of the target subject between the first time point and a time point when the second medical image is acquired based on the sets of image data.

In some embodiments, the plurality of medical images may include a third medical image acquired before the invasive device is inserted into the target subject and a fourth medical image acquired after the invasive device into the target subject. The processing device 120 may determine a third time point at which the third medical image is acquired and a fourth time point at which the fourth medical image is acquired. The processing device 120 may select a third set of image data corresponding to the third medical image from the plurality of sets of image data, wherein the third set of image data may be acquired at a time point that is the closest to or same as the third time point. The processing device 120 may determine a fourth set of image data corresponding to the fourth medical image from the plurality of sets of image data, wherein the fourth set of image data may be acquired at a time point that is the closest to or same as the fourth time point. The processing device 120 may determine a motion of the target subject between the third time point and the fourth time point based on the third set of image data and the fourth set of image data. In some embodiments, a plurality of fourth medical images may be acquired. For each of the fourth medical images, the processing device 120 may determine a motion of the target subject between the third time point and a time point when the fourth medical image is acquired based on the sets of image data.

In some embodiments, the processing device 120 may determine the motion of the target subject based on a marker placed on the target subject. For example, the processing device 120 may identify a position of a representation of the marker in each set of image data. Further, the processing device 120 may determine the motion of the target subject based on a difference between the positions of the representation of the marker in the sets of image data. In 3140, the processing device 120 (e.g., the analyzing module 520) may generate a target image of the target subject based on the plurality of medical images, wherein motion correction may be performed based on the detected motion of the target subject during the generation of the target image.

Figure 32:
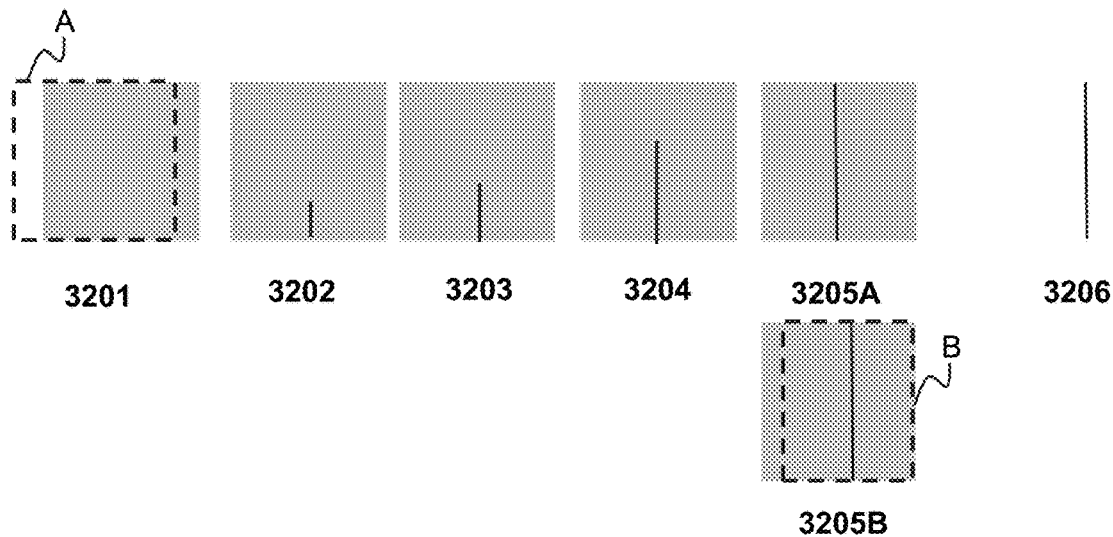
FIG. 32 illustrates a schematic diagram of an exemplary process of generating a first target image according to some embodiments of the present disclosure.

In some embodiments, the target image of the target subject may be generated by performing motion correction on the plurality of medical images (or a portion thereof) based on the detected motion of the target subject. For example, as described in connection with operation 3110, the plurality of medical images may include a first medical image acquired before a contrast agent is injected into the target subject at a first time point and a second medical image acquired after the contrast agent is injected into the target subject at a second time point. The processing device 120 may generate a corrected first medical image by correcting the first medical image based on the motion of the target subject between the first and second time points. If the target subject moves, the scan region corresponding to the second medical image may be different from the scan region corresponding to the first medical image. The processing device 120 may need to determine a mask corresponding to the scan region of the second medical image. For instance, the processing device 120 may determine a motion vector of the first medical image based on a vector indicating the motion of the target subject. Merely by way of example, the vector indicating the motion of the target subject may be denoted as (1, 1), the processing device 120 may determine the motion vector of the first medical image to be (−1, −1). The processing device 120 may move the first medical image according to the motion vector of the first medical image, and determine an overlapping region between the first medical image and the moved first medical image as the corrected first medical image. In other words, a region corresponding to the scan region of the second medical imaging device may be determined from the first medical image as the corrected first medical image. The processing device 120 may further generate a first target image indicating blood vessels of the target subject based on the corrected first medical image and the second medical image. For example, the processing device 120 may subtract the corrected first medical image from the second medical image (or a portion thereof) to generate the target image. More descriptions regarding the generation of a first target image based on a first medical image and a second medical image may be found elsewhere in the present disclosure (FIG. 32 and the description thereof).

As another example, as described in connection with operation 3110, the plurality of medical images may include a third medical image acquired before an invasive device is inserted into the target subject at a third time point and a fourth medical image acquired after the invasive device is inserted into the target subject at a fourth time point. The processing device 120 may generate a corrected third medical image by correcting the third medical image based on the motion of the target subject between the third and fourth time points. The processing device 120 may generate a second target image indicating the invasive device within the target subject based on the corrected third medical image and the fourth medical image. The generation of the second target subject based on the third and fourth medical images may be performed in a similar manner as the generation of the first target image based on the first and second medical images, and the descriptions thereof are not repeated here.

Figure 33:
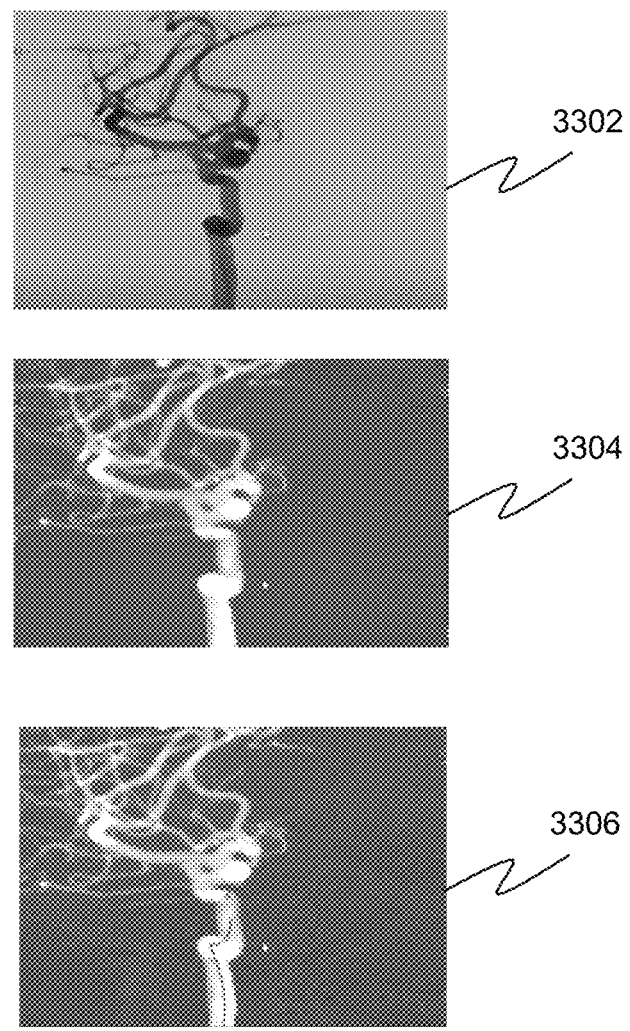
FIG. 33 illustrates a schematic diagram of an exemplary process for generating a composite image of a target subject according to some embodiments of the present disclosure.

In some embodiments, the processing device 120 may further obtain a reference image indicating blood vessels of the target subject. The reference image may be pre-generated and stored in a storage device (e.g., the storage device 130, the storage device 220, the storage 390, or an external source). Alternatively, the reference image may be generated by performing a DSA scan on the target subject. For example, the reference image may be generated in a similar manner as how a first target image 3206 is generated as shown in FIG. 32 is generated. Further, the processing device 120 may generate a composite image indicating the invasive device within the blood vessels of the target subject based on the reference image and the second target image. For instance, the processing device 120 may generate a target reference image by transforming the reference image. The transformation operation may include, for example, changing colors of the foreground and background of the reference image, e.g., reversing the colors of the foreground and background. The processing device 120 may generate the composite image by combining the target reference image and the second target image. In some embodiments, the processing device 120 may generate the composite image by combining the second target image and the original reference image. More descriptions regarding the generation of a composite image may be found elsewhere in the present disclosure (FIG. 33 and the description thereof).

As still another example, the processing device 120 may obtain a reference subject model representing an internal structure of the target subject. The processing device 120 may generate a corrected reference subject model by correcting the reference subject model based on the motion of the target subject. The processing device 120 may further generate a third target image of the target subject by combining the corrected reference subject model and at least one of the plurality of medical images of the target subject. More descriptions regarding the generation of the third target image based on the reference subject model may be found elsewhere in the present disclosure (e.g., FIGS. 34 and 35 and the descriptions thereof).

According to some embodiments of the present disclosure, during a scan (e.g., a DSA scan or a roadmap scan) performed on the target subject, a plurality of sets of image data may be captured by an image capturing device (e.g., the image capturing device 160) at a time series. The motion of the target subject may be monitored continuously or intermittently (e.g., periodically) based on the plurality of sets of image data of the target subject. Medical image(s) acquired during the scan may be motion corrected based on the motion of the target subject. Traditionally, the motion correction in the medical image(s) may be post-processed after the imaging is finalized. The motion correction cannot be adjusted promptly to compensate for the motion of the target subject. By the process 3100, the motion correction in the medical image(s) may be performed continuously or intermittently (e.g., periodically) during the imaging of the target subject, which can achieve a prompt compensation for the motion of the target subject.

FIG. 32 illustrates a schematic diagram of an exemplary process of generating a first target image according to some embodiments of the present disclosure. As shown in FIG. 32, a first medical image 3201 may be acquired before a contrast agent is injected into a target subject and second medical images 3202, 3203, 3204, and 3205A may be acquired after the contrast agent is injected into the target subject. A black line in the images represents a blood vessel of the target subject. For example, if the target subject does not move in a period between a first time point when the first medical image 3201 is acquired and a second time point when the second medical image 3205A is acquired, an image 3206 showing the blood vessel of the target subject may be generated by subtracting the first medical image 3201 from the second medical image 3205A. If the target subject moves in the period, the scan region of the target subject at the second time point may be different from that at the first time point. For example, a second medical image 3205B may be acquired if the target subject moves right for a certain distance. To reduce or eliminate the effect of the motion of the target subject, a corrected first medical image (not shown) may be generated by correcting the first medical image 3201 based on the motion of the target subject during the period. For example, the first medical image 3201 may be moved left for a certain distance as indicated by a dotted box A in FIG. 32, and an overlapping region between the first medical image 3201 and the moved first medical image may be designated as the corrected first medical image. The overlapping region may correspond to a scan region (as indicated by a dotted box B in FIG. 32) that is scanned at both the first time point and the second time point. Therefore, the overlapping region may be used as the corrected first medical image. For example, the target image 3206 may be generated by subtracting the corrected first medical image from a portion of the second medical image 3205 as indicated by the dotted box B.

FIG. 33 illustrates a schematic diagram of an exemplary process for generating a composite image of a target subject according to some embodiments of the present disclosure. As shown in FIG. 33, a reference image 3302 representing blood vessels of a target subject may be acquired. For example, the reference image 3302 may be generated in a similar manner as how the first target image 3206 is generated as described in operation FIG. 32. Then, a target reference image 3304 may be generated by transforming the reference image 3302. Blood vessels in black in the reference image 3302 may be transformed into blood vessels in white in the target reference image 3304. Further, a composite image 3306 may be generated by combing the target reference image 3304 and a second target image indicating an invasive device within the target subject. The composite image 3306 may indicate the invasive device within the blood vessels of the target subject.

Figure 34:
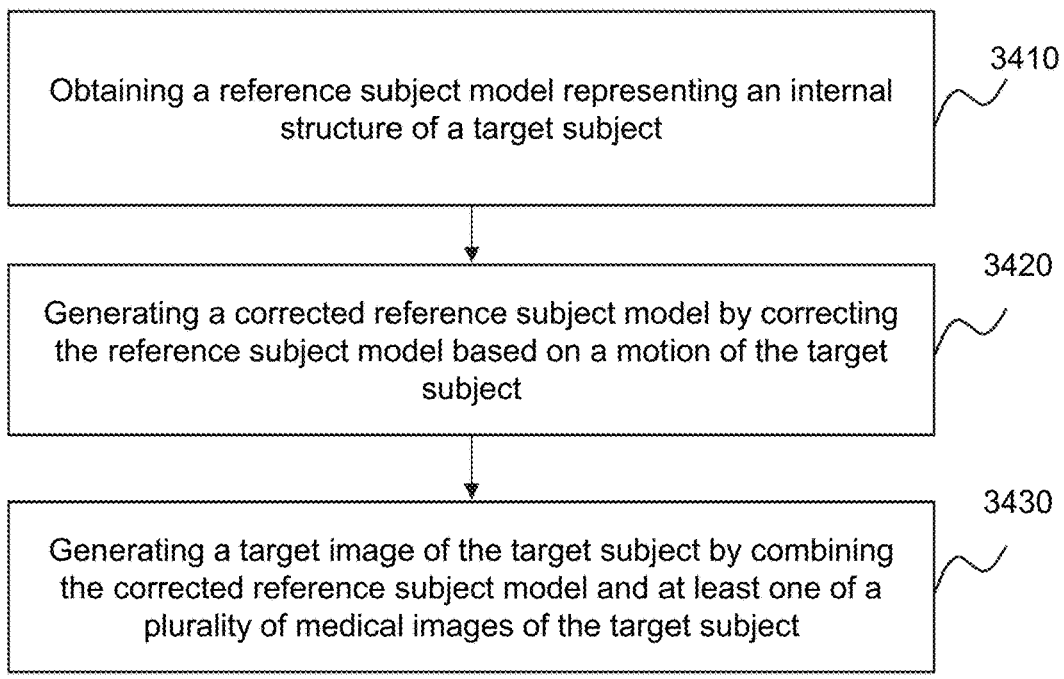
FIG. 34 is a flowchart illustrating an exemplary process for generating a target image of a target subject according to some embodiments of the present disclosure.

In some embodiments, operation 3140 in FIG. 34 may be achieved by performing one or more operations of process 3400 as shown in FIG. 34.

In 3410, the processing device 120 (e.g., the analyzing module 520) may obtain a reference subject model representing an internal structure of the target subject (e.g., a patient).

For example, the reference subject model may indicate organs, tissues, and/or blood vessels of the target subject. In some embodiments, the reference subject model may be generated and stored in a storage device (e.g., the storage device 130, the storage device 220, the storage 390, or an external source). The processing device 120 may retrieve the reference subject model from the storage device. In some embodiments, the processing device 120 may generate the reference subject model by performing operations 2110 to 2130 as described in FIG. 21.

In 3420, the processing device 120 (e.g., the analyzing module 520) may generate a corrected reference subject model by correcting the reference subject model based on the motion of the target subject.

The generation of the corrected reference subject model may be performed in a similar manner as the generation of the corrected first medical image as described in operation 3140.

In 3430, the processing device 120 (e.g., the analyzing module 520) may generate a third target image of the target subject by combining the corrected reference subject model and at least one of the plurality of medical images of the target subject.

For example, the target image may be generated by combining the corrected reference subject model and the fourth medical image captured after the invasive device is inserted into the target subject. The third target image may indicate both the internal structure of the target subject (including the blood vessels) and the position of the invasive device. In some embodiments, the processing device 120 may generate a target reference subject model by transforming the corrected reference subject model, such that the color of the blood vessels in the target reference subject model may be different from the color of the invasive device in the at least one of the plurality of medical images. For example, the blood vessels in the target reference subject model may be displayed in red, while the invasive device in the at least one of the medical images may be displayed in white. Further, the processing device 120 may generate the third target image by combining the target reference subject model and the at least one of the plurality of medical images of the target subject.

Figure 35:
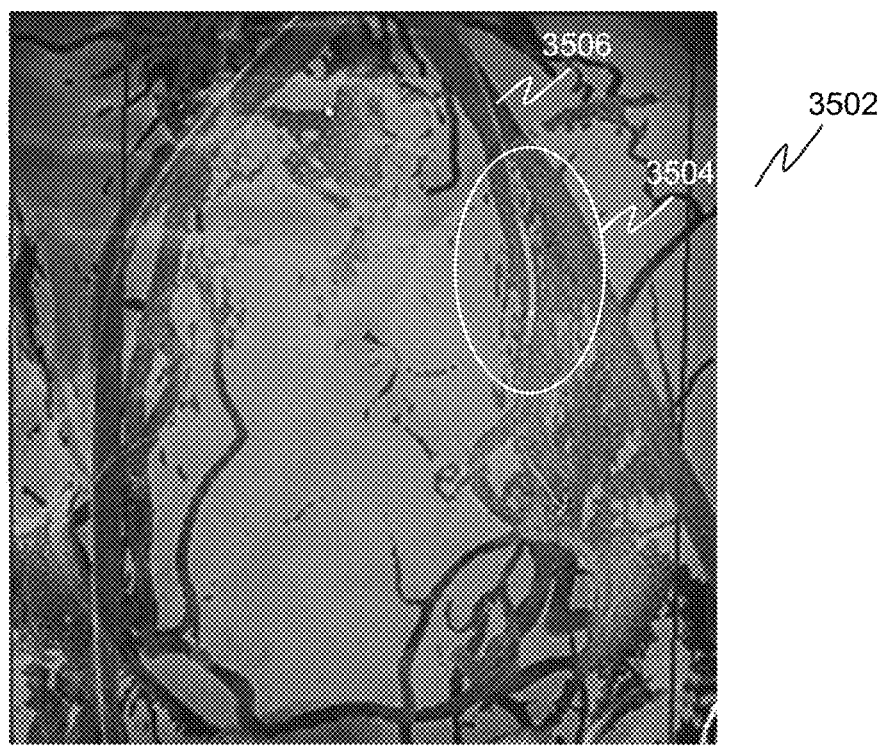
FIG. 35 illustrates a schematic diagram of an exemplary third target image of a target subject according to some embodiments of the present disclosure.

For illustration purposes, FIG. 35 illustrates a schematic diagram of an exemplary third target image of a target subject according to some embodiments of the present disclosure. As shown in FIG. 35, in the target image 3502, blood vessels (e.g., a blood vessel 3506) of the target subject is in black and an invasive device 3504 is in white, such that the target image 3502 can indicate the invasive device 3504 within the blood vessels more clearly. The third target image 3502 can be updated in real time to indicate a trajectory of the invasive device 3504 in the blood vessels.

In some embodiments, the reference subject model may be generated based on reference image data of the target subject (e.g., a CT image of the target subject or a first target image as described in operation 3140) representing internal structure (e.g., blood vessels) of the target subject and a subject model of the target subject. The reference subject model may be motion-corrected by compensating for the motion of the target subject. As a combination of the corrected reference subject model and a medical image (e.g., the fourth medical image) indicating a position of the invasive device relative to the target subject, the third target image may not only include comprehensive information of the target subject (e.g., both the appearance and the internal structure of the target subject), but also indicate the positional relationship between the invasive device and the internal structure (e.g., the blood vessels) of the target subject clearly and accurately.

In some embodiments, one or more operations may be added or omitted. For example, a process for storing or displaying the target image may be added after operation 3140. In some embodiments, two or more operations may be performed simultaneously. For example, operation 3110 and operation 3120 may be performed simultaneously.

Figure 36:
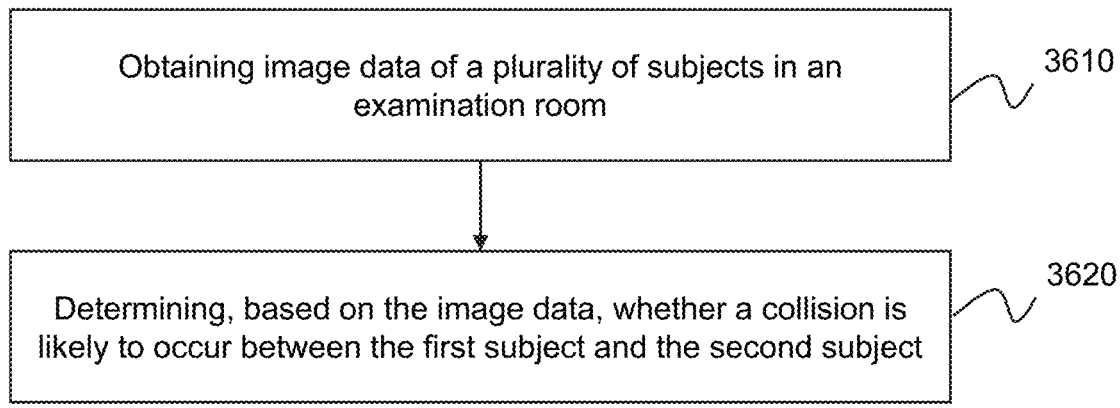
FIG. 36 is a flowchart illustrating an exemplary process for collision detection according to some embodiments of the present disclosure.

FIG. 36 is a flowchart illustrating an exemplary process for collision detection according to some embodiments of the present disclosure.

In some embodiments, a scan or a treatment may be performed on a target subject (e.g., a patient or a portion thereof) by a medical device, such as a medical imaging device, a radiotherapy device, etc. The target subject and the medical device may be located in an examination room. Process 3600 may be performed before and/or during the scan or the treatment of the target subject. For example, the process 3600 may be performed continuously or intermittently (e.g., periodically) before and/or during the scan or the treatment of the target subject to detect a possible collision between a plurality of subjects in the examination room.

In 3610, the processing device 120 (e.g., the acquisition module 510) may obtain image data of the plurality of subjects in the examination room captured by an image capturing device.

The plurality of subjects may include one or more biological subjects and/or one or more non-biological subjects in the examination room, such as the medical device, the target subject (e.g., a patient), a roof, a floor, a wall, a surgical towel, a lead curtain, a cable, or the like, or any combination thereof. In some embodiments, operation 3610 may be performed in a similar manner with operation 2810 as described in connection with FIG. 28, and the descriptions thereof are not repeated here.

In some embodiments, the image data may include a set of image data captured by the image capturing device at a specific time point. Alternatively, the image data may include a plurality of sets of image data at a series of time points. Each of the plurality of sets of image data may correspond to one of the plurality of time points. The time interval between each pair of consecutive time points of the plurality of time points may be fixed or unfixed.

In some embodiments, the plurality of subjects may include one or more pairs of subjects, wherein each pair may include a first subject and a second subject. For each pair of subjects, the processing device 120 may determine whether a collision is likely to occur between the pair of subjects. For example, each subject in the examination room may be paired with each of the remaining subject(s) in the examination room. As another example, the processing device 120 may select a pair of subjects to be monitored for collision avoidance from the plurality of subjects.

The pair of subjects may be selected according to one or more selection rules. For example, a collision between two subjects may be negligible if the collision does not have a significant effect on the treatment or the scan performed on or to be performed on the target subject. Merely by way of example, a subject may not be selected if it has a soft texture or a flexible texture, such as a surgical towel, a lead curtain, a cable, etc. As another example, at least one subject of the selected pair of subjects may be moveable. Normally, a collision may not be likely to occur between two immovable subjects. As yet another example, a subject may be omitted from collision detection if its distance to the target subject or the medial device exceeds a threshold distance.

In some embodiments, the processing device 120 (e.g., the analyzing module 520) may identify the plurality of subjects in the examination room based on the image data. For instance, the processing device 120 may identify the plurality of subjects based on the image data using an object detection algorithm. Exemplary object detection algorithms may include a Region-CNN algorithm, a single shot multi-box detector (SSD) algorithm, a you only look once (YOLO) network, etc. The processing device 120 may further obtain feature information relating to each of the plurality of subjects. Exemplary feature information of a subject may include a texture of the subject, whether the subject is movable, a label indicating whether the subject (e.g., a patient, a medical device) needs to be monitored for collision avoidance, or the like, or any combination thereof. The processing device 120 may select a pair of subjects to be monitored from the plurality of subjects based on the feature information. In conventional methods for collision avoidance (or collision detection), all subjects in the examination room may be monitored for collision avoidance. The methods for collision avoidance provided in the present application may monitor the selected subjects, which may improve the efficiency of collision avoidance (or collision detection) by reducing, e.g., the processing time, the computational complexity and/or cost, etc.

In some embodiments, for each pair of subjects from the plurality of subjects in the examination room, the processing device 120 may determine whether a collision is likely to occur between the pair of subjects by performing operation 3620. For illustration purposes, the implementation of the process 3620 for a pair of subjects that includes a first subject and a second subject is described hereinafter.

In 3620, the processing device 120 (e.g., the analyzing module 520) may determine, based on the image data, whether a collision is likely to occur between the first subject and the second subject.

In some embodiments, as described in connection with operation 3610, the image data may include a plurality of sets of image data corresponding to a plurality of time points. The processing device 120 may determine whether a collision is likely to occur between the first subject and the second subject based on a first trajectory of the first subject and a second trajectory of the second subject. More descriptions regarding the determination of whether a collision is likely to occur between the first subject and the second subject based on the first trajectory and the second trajectory may be found elsewhere in the present disclosure, e.g., in FIG. 37 and relevant descriptions thereof.

Additionally or alternatively, the processing device 120 may determine whether a collision is likely to occur between the first subject and the second subject based on a distance between the first subject and the second subject. The distance may be determined based on the image data. More descriptions regarding the determination of whether a collision is likely to occur between the first subject and the second subject based on a distance between the first subject and the second subject may be found elsewhere in the present disclosure, e.g., in FIG. 38 and relevant descriptions thereof.

In some embodiments, in response to determining that a collision is likely to occur between the first subject and the second subject, the processing device 120 (e.g., the analyzing module 520) may cause a terminal device to generate a notification to a user (e.g., an operator). The notification may be configured to notify the user that a collision is likely to occur. For example, the notification may be provided to the user in the form of a text, a voice message, an image, an animation, a video, etc.

Additionally or alternatively, in response to determining that a collision is likely to occur between the first subject and the second subject, the processing device 120 (e.g., the analyzing module 520) may generate an instruction to decelerate or stop at least one of the first subject or the second subject so as to avoid a collision.

In some embodiments, the imaging system 100 may operate in an automatic collision detection mode during the scan of the target subject. In the automatic collision detection mode, the one or more components of the medical imaging device may move automatically, and a user (e.g., an operator) of the imaging system 100 cannot control the movement of the one or more components of the medical imaging device. In response to a determination that a collision is likely to occur between the first subject and the second subject, the automatic collision detection mode may be closed and the imaging system 100 may operate in a manual control mode. In the manual control mode, the user may be able to control the movement of the one or more components of the medical imaging device 110. For example, the user may decelerate or stop at least one of the first subject or the second subject so as to avoid a collision, or move the first subject and/or the second subject after a collision is occurred between the two subjects.

Conventionally, a process of collision detection includes determining the position information of a specific component of the medical device based on an original position of the specific component, a position or position change of the specific component detected by a position sensor of the medical device, etc. Whether a collision is likely to occur between the specific component and another designated component of the medical device (e.g., the gantry or the couch) may be estimated. However, it may be difficult to determine whether a collision is likely to happen between the specific component and any other non-designated subject in the examination room (e.g., a terminal device, a trolley, a target subject to be scanned or treated, an operator). The method for collision detection provided in the present disclosure may include determining the position information of a plurality of subjects in the examination room based on image data acquired by one or more image capturing devices. As compared to the conventional approach, the method for collision detection provided in the present disclosure may improve the accuracy of determining whether a collision is likely to happen since the position information of all the plurality of subjects in the examination room may be monitored in real time. Thus, the method for collision detection provided in the present disclosure may effectively avoid collisions between any pair of subjects in real time, thereby avoiding causing damage to the target subject, the operator, the medical device, or other devices.

Figure 37:
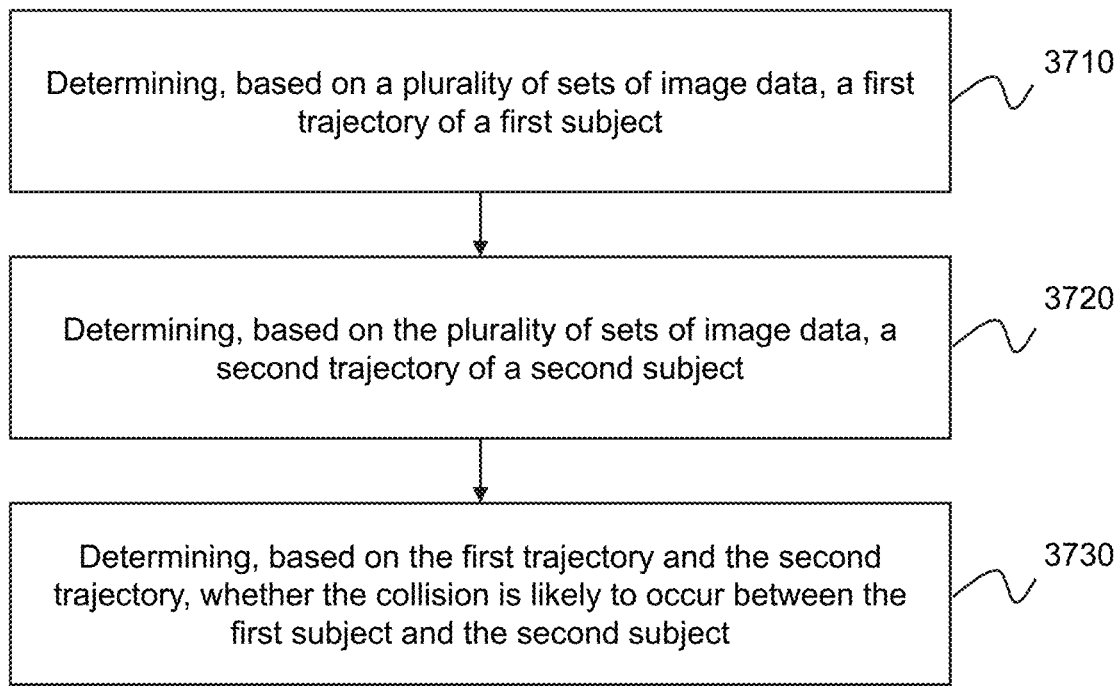
FIG. 37 is a flowchart illustrating an exemplary process for collision detection according to some embodiments of the present disclosure.

In some embodiments, the image data acquired in operation 3610 may include a plurality of sets of image data corresponding to a plurality of time points. Operation 3620 may be performed by one or more operations of process 3700 as shown in FIG. 37.

In 3710, the processing device 120 (e.g., the analyzing module 520) may determine, based on the plurality of sets of image data, a first trajectory of the first subject.

The first trajectory of the first subject may include a first travel path that the first subject has gone through at the plurality of time points. For example, for each of the plurality of sets of image data, the processing device 120 may determine a position of the first subject at the time point corresponding to the set of image data. The processing device 120 may further determine the first travel path that the first subject has gone through based on the positions of the first subject at the plurality of time points. Additionally or alternatively, the first trajectory of the first subject may include a first predicted travel path that the first subject will go through at one or more future time points. For example, the processing device 120 may determine one or more first predicted positions of the first subject at one or more future time points. Merely by way of example, the one or more first predicted positions of the first subject may be determined based on one or more moving parameters of the first subject at the plurality of time points (or a portion thereof). The one or more moving parameters may include a velocity, an angular velocity, an accelerated velocity, or the like, or a combination thereof. As another example, the processing device 120 may determine the first predicted travel path of the first subject by extending the first travel path that the first subject has gone through. In some embodiments, the processing device 120 (e.g., the analyzing module 520) may determine the first travel path that the first subject has gone through and/or the first predicted travel path of the first subject using a machine learning model, a fitting algorithm, an interpolation algorithm, or the like.

In 3720, the processing device 120 (e.g., the analyzing module 520) may determine, based on the plurality of sets of image data, a second trajectory of the second subject.

The determination of the second trajectory of the second subject may be performed in a similar manner as that of the first trajectory of the first subject. For example, the second trajectory of the second subject may include a second travel path that the second subject has gone through at the plurality of time point and/or a second predicted travel path that the second subject will go through at the one or more future time points.

In 3730, the processing device 120 (e.g., the analyzing module 520) may determine, based on the first trajectory and the second trajectory, whether a collision is likely to occur between the first subject and the second subject.

For example, the processing device 120 may determine that a collision is likely to occur between the first subject and the second subject if the first trajectory and the second trajectory intersect or a distance between a position in the first trajectory at a time point and a position in the second trajectory at the time point is below a threshold distance.

In some embodiments, the processing device 120 may determine whether a collision is likely to occur between the first subject and the second subject based on the first trajectory, the second trajectory, and feature information (e.g., the size, the shape) of the first subject and the second subject. For instance, based on the first trajectory and feature information of the first subject, the processing device 120 may determine a space occupied by the first subject at each of the one or more future time points. Based on the second trajectory and feature information of the second subject, the processing device 120 may determine a space occupied by the second subject at each of the one or more future time points. The processing device 120 may further determine whether the space occupied by the first subject at a specific future time point overlaps the space occupied by the second subject at the specific future time point. If the space occupied by the first subject at a specific future time point overlaps the space occupied by the second subject at the specific future time point, the processing device 120 may determine that a collision is likely to occur between the first subject and the second subject. If the space occupied by the first subject at each future time point does not overlap the space occupied by the second subject at the future time point, the processing device 120 may determine that a collision is unlikely to occur between the first subject and the second subject.

Figure 38:
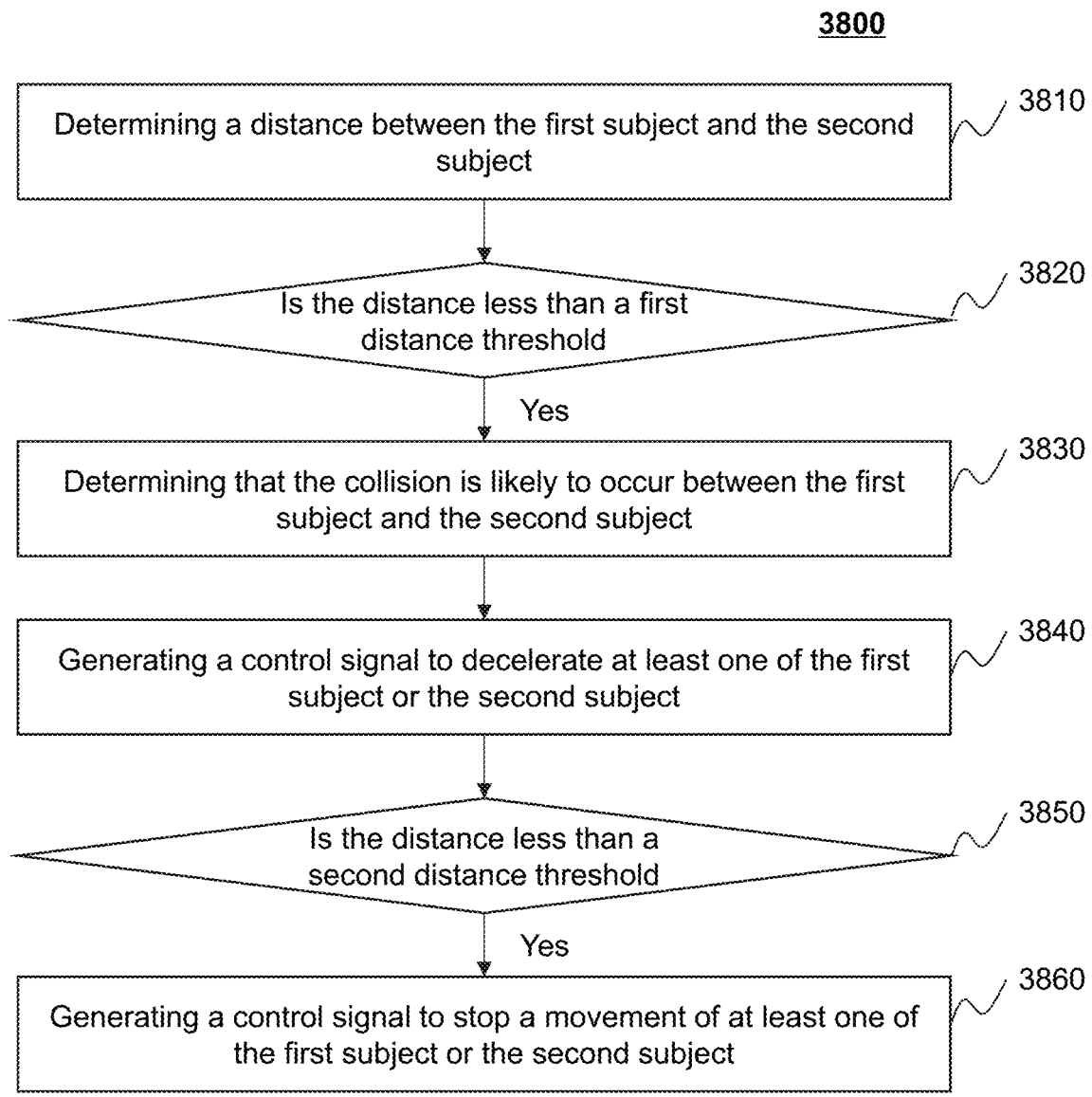
FIG. 38 is a flowchart illustrating an exemplary process for collision detection according to some embodiments of the present disclosure.

In some embodiments, the image data acquired in operation 3610 may include one or more sets of image data corresponding to one or more time points. For each set of image data, one or more operations of process 3800 as shown in FIG. 38 may be performed. For illustration purposes, the implementation of the process 3800 for a set of image data corresponding to a first time point is described hereinafter.

In 3810, the processing device 120 (e.g., the analyzing module 520) may determine, based on the set of image data, a distance between the first subject and the second subject.

The distance between the first subject and the second subject may include a pixel distance in image domain or a physical distance in physical space between the first and second subject at the first time point. In some embodiments, the processing device 120 may determine a position of the first subject and a position of the second subject based on the image data. The processing device 120 may determine the distance between the first subject and the second subject based on the position of the first subject and the position of the second subject.

In 3820, the processing device 120 (e.g., the analyzing module 520) may determine whether the distance between the first subject and the second subject is less than a first distance threshold.

In some embodiments, the first distance threshold may have a preset value stored in a storage device (e.g., the storage device 130) or be manually set by a user (e.g., an operator).

For example, the first distance threshold may be 10 cm, 12 cm, 8 cm, etc. In some embodiments, the value of the first distance threshold may be determined based on the image data. For instance, the processing device 120 may obtain a preset value of the first distance threshold from the storage device and determine whether the preset value needs to be adjusted based on the image data. For example, the first subject may be a scanning table and the second subject may be a C-shaped arm. The target subject may lie on the scanning table. If the distance between the C-shaped arm and the target subject is below a threshold distance (e.g., a portion (e.g., the head) of the target subject reaches beyond the scanning table and is close to the C-shaped arm), the first distance threshold may be increased (e.g., from 8 cm to 10 cm) to decrease the possibility of a collision between the target subject and the C-shaped arm. In some embodiments, the first distance threshold may be determined based on feature information (e.g., a body size, a height, a width, a thickness) of the target subject. For example, if the body size of the target subject is relatively small, the first distance threshold may be relatively large.

In response to determining that the distance between the first subject and the second subject is less than the first distance threshold, the process 3800 may proceed to operations 3830 to 3860.

In 3830, the processing device 120 (e.g., the analyzing module 520) may determine that a collision is likely to occur between the first subject and the second subject.

In 3840, the processing device 120 (e.g., the control module 530) may generate a control signal to decelerate at least one of the first subject or the second subject.

For example, the first subject may be the target subject, and the second subject may be a component of the medical device, such as a C-shaped arm. The processing device 120 may decelerate the second subject. As another example, the first subject may be the C-shaped arm, and the second subject may be a scanning table. The processing device 120 may decelerate the first subject or the second subject, or both the first subject and the second subject.

In 3850, the processing device 120 (e.g., analyzing module 520) may determine whether the distance between the first subject and the second subject is less than a second distance threshold.

The second distance threshold may be smaller than the first distance threshold. In some embodiments, the first distance threshold may also be referred to as a deceleration threshold, and the second distance threshold may also be referred to as a stopping threshold. In some embodiments, the second distance threshold may be predetermined. For example, the second distance threshold may be predetermined as 5 cm, 3 cm, etc. In some embodiments, the value of the second distance threshold may be determined based on the image data. For instance, the processing device 120 (e.g., the analyzing module 520) may obtain a preset value of the second distance threshold from the storage device and determine whether the preset value needs to be adjusted based on the image data. The determination of the second distance threshold may be performed in a similar manner as that of the first distance threshold as described in connection with operation 3820.

In 3860, in response to determining that the distance between the first subject and the second subject is less than the second distance threshold, the processing device 120 (e.g., the analyzing module 520) may generate a control signal to stop the movement of at least one of the first subject or the second subject.

In some embodiments, after the first subject and/or the second subject is decelerated as described in operation 3840, the collision between the first subject and the second subject may be less likely to occur. Such a deceleration process may achieve the purpose of avoiding the collision without causing a significant effect on the scan or the treatment on the target subject. However, in some cases, even if the first subject and/or the second subject is decelerated, in response to determining that the distance between the first subject and the second subject is less than the second distance threshold, the processing device 120 may determine that there is still a possibility that the collision may occur. The first subject and/or the second subject may be stopped in order to further avoid the collision. In this way, the collision between the first subject and the second subject may be effectively avoided.

For example, the first subject may be the target subject, and the second subject may be a component of the medical device, such as a C-shaped arm. The processing device 120 may stop the movement of the second subject. As another example, the first subject may be the C-shaped arm, and the second subject may be a scanning table. The processing device 120 may stop the movement of the first subject or the second subject, or both the first subject and the second subject.

In some embodiments, the processing device 120 (e.g., the analyzing module 520) may cause an instruction to be generated based on the image data. The instruction may be configured to guide a user to control the movement of at least one of the first subject or the second subject. For example, the instruction may guide the user to move the first subject and/or the second subject in a certain direction for a certain distance. The instruction may be provided to the user in the form of an image, a text, video, a voice message, etc. For example, a terminal device of the user may display an image including the first subject and/or the second subject, and the image may be annotated with an arrow indicating a recommended moving direction of the first subject and/or the second subject.

Conventionally, after a collision between a first subject and a second subject occurs, the user may manually control the movement of the first subject and/or the second subject. In some cases, it may be difficult to determine a moving direction and/or a moving distance of the movement of the first subject and/or the second subject. If the user controls the first subject and/or the second subject to move in a wrong direction, extra damage may be caused to the first subject and/or the second subject. By automatically determining the moving direction and/or the moving distance of the movement, and providing a corresponding instruction for the user, such situations may be reduced or avoided. The instruction may be provided to the user via the terminal device in an intuitive and efficient way.

In some embodiments, one or more additional operations not described may be added and/or one or more of the operations discussed may be omitted. Additionally, the order of the operations illustrated in FIGS. 36-38 and described below is not intended to be limiting. For example, the process 3700 may include an additional operation to generate a control signal for decelerating or stopping the movement of at least one of the first subject or the second subject in response to determining that a collision is likely to occur. As another example, operations 3820 to 3840 may be omitted, and the processing device 120 may directly determine whether the distance is less than the second distance threshold.

In some embodiments, in operation 3850, a second set of image data of the subjects in the examination room may be acquired, wherein the second set of image data may correspond to a second time point after the first time point. The second set of image data may indicate an updated state of the first and second subjects after at least one of the first and second subjects is decelerated. The processing device 120 may determine a second distance between the first and second subjects at the second time point based on the second set of image data. The processing device 120 may further determine whether the second distance is less than (or equal to) the second distance threshold. In 3860, in response to determining that the second distance between the first subject and the second subject is less than (or equal to) the second distance threshold, the processing device 120 (e.g., the analyzing module 520) may generate the control signal to stop the movement of at least one of the first subject or the second subject.

In some embodiments, a process described in the present disclosure may be implemented in the imaging system 100 illustrated in FIG. 1. For example, the process may be stored in a storage device (e.g., the storage device 130, the storage device 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3, one or more modules as shown in FIG. 5). In some embodiments, operations of different processes may be combined in any suitable manner.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer-readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the users computer, partly on the users computer, as a stand-alone software package, partly on the users computer and partly on a remote computer or entirely on the remote computer or server. In the latter scenario, the remote computer may be connected to the users computer through any type of network, including a local area network (LAN) or a wide area network (VVAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations thereof, are not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A method for medical imaging implemented on a computing device having one or more processors and one or more storage devices, the method comprising:
  acquiring a plurality of medical images of a target subject by performing a scan on the target subject using a medical imaging device;
  obtaining image data of the target subject, wherein the image data includes a plurality of sets of image data of the target subject captured by an image capturing device during the scan at a series of time points, each of the plurality of sets of image data corresponds to one of the series of time points;
  detecting, based on the plurality of sets of image data, a motion of the target subject; and
  generating, based on the plurality of medical images, a target image of the target subject, wherein motion correction is performed based on the detected motion of the target subject during the generation of the target image.

2. The method of claim 1, wherein the plurality of medical images comprise a first medical image acquired before a contrast agent is injected into the target subject and a second medical image acquired after the contrast agent is injected into the target subject.

3. The method of claim 2, wherein the generating, based on the plurality of medical images, a target image of the target subject comprises:

generating a corrected first medical image by correcting the first medical image based on the motion of the target subject; and generating, based on the corrected first medical image and the second medical image, the target image representing blood vessels of the target subject.

4. The method of claim 1, wherein the plurality of medical images comprise a third medical image captured before an invasive device is inserted into the target subject and a fourth medical image acquired after the invasive device is inserted into the target subject.

5. The method of claim 4, wherein the generating, based on the plurality of medical images, a target image of the target subject comprises:

generating a corrected third medical image by correcting the third medical image based on the motion of the target subject; and generating, based on the corrected third medical image and the fourth medical image, the target image representing the invasive device within the target subject.

6. The method of claim 5, further comprising:

obtaining a reference image representing blood vessels of the target subject; and generating a composite image representing the invasive device within the blood vessels of the target subject based on the reference image and the target image.

7. The method of claim 6, wherein the generating a composite image representing the invasive device within the blood vessels of the target subject based on the reference image and the target image comprises:

generating a target reference image by transforming the reference image; and generating the composite image by combining the target reference image and the target image.

8. A method for monitoring a target subject during a scan of the target subject, implemented on a computing device having at least one processor and at least one storage device, the method comprising:

obtaining a plurality of sets of image data of the target subject, the target subject being scanned by a medical imaging device, the plurality of sets of image data being captured by an image capturing device during the scan of the target subject at a series of time points, each of the plurality of sets of image data corresponding to one of the series of time points;

determining, based on the plurality of sets of image data, whether the target subject moves over the series of time points; and in response to determining that the target subject moves over the series of time points, generating control information for adjusting the scan of the target subject.

9. The method of claim 8, wherein the determining, based on the plurality of sets of image data, whether the target subject moves over the series of time points comprises:

for each of the plurality of sets of image data, identifying at least one feature point representing at least one body landmark of the target subject from the set of image data;

determining, based on the at least one feature point identified in each of the plurality of sets of image data, a motion of the at least one body landmark over the series of time points; and determining, based on the motion of the at least one body landmark, whether the target subject moves over the series of time points.

10. The method of claim 9, wherein for each of the plurality of sets of image data, the identifying at least one feature point representing at least one body landmark of the target subject from the set of image data comprises:

generating a first subject model representing the target subject based on the set of image data; and identifying, from the first subject model, the at least one feature point representing the at least one body landmark of the target subject.

11. The method of claim 8, wherein the determining, based on the plurality of sets of image data, whether the target subject moves over the series of time points comprises:

for each of the plurality of sets of image data, determining one or more parameter values of one or more posture parameters of the target subject based on the set of image data; and determining, based on the one or more parameter values of the one or more posture parameters of the target subject corresponding to each of the set of image data, whether the target subject moves over the series of time points.

12. The method of claim 11, wherein for each of the plurality of sets of image data, the determining one or more parameter values of one or more posture parameters of the target subject based on the set of image data comprises:

generating a second subject model representing the target subject based on the set of image data; and determining the one or more parameter values of the one or more posture parameters of the target subject based on the second subject model.

13. A method for positioning a target subject to be scanned by a medical imaging device, implemented on a computing device having one or more processors and one or more storage devices, the method comprising:

obtaining image data indicative of a position of the target subject relative to one or more components of the medical imaging device, the image data being captured by an image capturing device;

obtaining position information relating to the one or more components of the medical imaging device;

determining a plurality of regions of the target subject based on the image data and the position information, different regions of the plurality of regions corresponding to different positioning procedures of the target subject;

causing a terminal device to display a target image of the target subject with a plurality of annotations of the plurality of regions.

14. The method of claim 13, wherein the one or more components of the medical imaging device include a scanning table that supports the target subject, and the plurality of regions include at least two of:

a first region that can be imaged by the medical imaging device without moving the scanning table, a second region that can be imaged by the medical imaging device by moving the scanning table;

a third region that cannot be imaged by the medical imaging device even if the target subject is moved via the scanning table.

15. The method of claim 13, wherein the one or more components of the medical imaging device include a scanning table that supports the target subject, the plurality of regions include a first region that can be imaged by the medical imaging device without moving the scanning table, and the method further comprises:

obtaining, via the terminal device, a first input associated with a first scan region of the target subject, wherein the first scan region is within the first region; and causing the medical imaging device to scan the first scan region based on the first input.

16. The method of claim 13, wherein the one or more components of the medical imaging device include a scanning table that supports the target subject, the plurality of regions include a second region that can be imaged by the medical imaging device by moving the scanning table, and the method further comprises:
- obtaining, via the terminal device, a second input associated with a second scan region of the target subject, wherein at least part of the second scan region is within the second region;
- determining a target position of the target subject based on the second input, the image data, and the position information;
- causing the scanning table to move the target subject to the target position; and
- causing the medical imaging device to scan the target subject when the target subject is at the target position.

17. The method of claim 13, wherein the one or more components of the medical imaging device include a scanning table that supports the target subject, the plurality of regions include a third region that cannot be imaged by the medical imaging device even if the target subject is moved via the scanning table, and the method further comprises:
- obtaining, via the terminal device, a third input associated with a third scan region of the target subject, wherein at least part of the third scan region is within the third region; and
- generating a notification indicating that the third scan region cannot be imaged by the medical imaging device.

18. The method of claim 13, wherein the plurality of annotations of the plurality of regions are displayed in the target image in different colors or different textures.

19. The method of claim 13, further comprising:
- obtaining an input associated with a scan region of the target subject from the terminal device;
- generating a second target image representing an internal structure of the scan region of the target subject, and causing the terminal device to display the second target image.

20. The method of claim 19, wherein the generating a second target image representing an internal structure of the scan region of the target subject comprises:
- obtaining reference image data representing an internal structure of the target subject;
- obtaining one or more parameter values of one or more scan parameters of the medical imaging device relating to a scan to be performed on the target subject; and
- generating the second target image representing the internal structure of the scan region to be scanned by the medical imaging device under the one or more parameter values based on the image data, the reference image data, and the one or more parameter values.

* * * * *